(12) United States Patent
Cohen et al.

(10) Patent No.: US 10,434,109 B2
(45) Date of Patent: Oct. 8, 2019

(54) COMPOSITIONS FOR TREATING NEUROLOGICAL DISORDERS

(71) Applicant: PHARNEXT, Issy Les Moulineaux (FR)

(72) Inventors: Daniel Cohen, Saint Cloud (FR); Ilya Chumakov, Vaux-Le-Penil (FR); Serguei Nabirochkin, Chatenay-Malabry (FR); Emmanuel Vial, Nice (FR); Mickael Guedj, Paris (FR)

(73) Assignee: PHARNEXT, Issy Les Moulineaux (FR)

( * ) Notice: Subject to any disclaimer, the term of this patent is extended or adjusted under 35 U.S.C. 154(b) by 0 days.

(21) Appl. No.: 16/025,461

(22) Filed: Jul. 2, 2018

(65) Prior Publication Data

US 2018/0338988 A1    Nov. 29, 2018

Related U.S. Application Data

(60) Division of application No. 15/848,230, filed on Dec. 20, 2017, which is a division of application No. 14/014,650, filed on Aug. 30, 2013, now Pat. No. 9,867,837, which is a continuation-in-part of application No. PCT/EP2012/053565, filed on Mar. 1, 2012.

(60) Provisional application No. 61/468,658, filed on Mar. 29, 2011.

(30) Foreign Application Priority Data

Mar. 1, 2011 (EP) ..................................... 11305217

(51) Int. Cl.

| | |
|---|---|
| *A61K 31/137* | (2006.01) |
| *A61K 31/155* | (2006.01) |
| *A61K 31/64* | (2006.01) |
| *A61K 31/185* | (2006.01) |
| *A61K 31/44* | (2006.01) |
| *A61K 45/06* | (2006.01) |
| *A61K 31/585* | (2006.01) |
| *A61K 31/138* | (2006.01) |
| *A61K 31/197* | (2006.01) |
| *A61K 31/28* | (2006.01) |
| *A61K 31/42* | (2006.01) |
| *A61K 31/423* | (2006.01) |
| *A61K 31/445* | (2006.01) |
| *A61K 31/4709* | (2006.01) |
| *A61K 31/48* | (2006.01) |
| *A61K 31/495* | (2006.01) |
| *A61K 31/496* | (2006.01) |
| *A61K 31/4985* | (2006.01) |
| *A61K 31/50* | (2006.01) |
| *A61K 31/167* | (2006.01) |
| *A61K 31/4164* | (2006.01) |

(52) U.S. Cl.
CPC .......... *A61K 31/585* (2013.01); *A61K 31/137* (2013.01); *A61K 31/138* (2013.01); *A61K 31/155* (2013.01); *A61K 31/167* (2013.01); *A61K 31/185* (2013.01); *A61K 31/197* (2013.01); *A61K 31/28* (2013.01); *A61K 31/4164* (2013.01); *A61K 31/42* (2013.01); *A61K 31/423* (2013.01); *A61K 31/44* (2013.01); *A61K 31/445* (2013.01); *A61K 31/4709* (2013.01); *A61K 31/48* (2013.01); *A61K 31/495* (2013.01); *A61K 31/496* (2013.01); *A61K 31/4985* (2013.01); *A61K 31/50* (2013.01); *A61K 31/64* (2013.01); *A61K 45/06* (2013.01)

(58) Field of Classification Search
CPC .... A61K 31/137; A61K 31/155; A61K 31/64; A61K 31/185; A61K 31/144; A61K 45/06
See application file for complete search history.

(56) References Cited

U.S. PATENT DOCUMENTS

| | | | |
|---|---|---|---|
| 5,677,344 A | 10/1997 | Greenfield et al. | |
| 8,741,886 B2 | 6/2014 | Cohen et al. | |
| 8,865,769 B2 | 10/2014 | Cohen et al. | |
| 9,144,558 B2 | 9/2015 | Cohen et al. | |

(Continued)

FOREIGN PATENT DOCUMENTS

| | | |
|---|---|---|
| CN | 101365451 A | 2/2009 |
| WO | 199219245 A1 | 11/1992 |

(Continued)

OTHER PUBLICATIONS

Tansey et al. "Neuroinflammation in Parkinson's disease: its role in neuronal death and implications for therapeutic intervention"; Neurobiol Dis., 2010, vol. 37, No. 3, pp. 510-518. (Year: 2010).*

Faroni et al. "Baclofen Modulates the Expression and Release of Neurotrophins in Schwann-Like Adipose Stem Cells", Journal of Molecular Neuroscience, May 31, 2012, vol. 49, pp. 233-243. (Year: 2012).*

Carter, M. D. et al. "The Development of New Therapeutics for Alzheimer's Disease", Clinical Pharmacology & Therapeutics, Jan. 1, 2010, pp. 47 5 486, vol. 88, No. 4.

(Continued)

*Primary Examiner* — Kendra D Carter

(74) *Attorney, Agent, or Firm* — Browdy and Neimark, PLLC

(57) ABSTRACT

The present invention relates to compositions and methods for the treatment of neurological disorders related to glutamate excitotoxicity and Amyloid β toxicity. More specifically, the present invention relates to novel combinatorial therapies of Multiple Sclerosis, Alzheimer's disease, Alzheimer's disease related disorders, Amyotrophic Lateral Sclerosis, Parkinson's disease, Huntington's disease, neuropathic pain, alcoholic neuropathy, alcoholism or alcohol withdrawal, or spinal cord injury.

7 Claims, 29 Drawing Sheets

Specification includes a Sequence Listing.

(56) References Cited

U.S. PATENT DOCUMENTS

| | | |
|---|---|---|
| 9,241,933 B2 | 1/2016 | Cohen et al. |
| 9,248,111 B2 | 2/2016 | Cohen et al. |
| 9,636,316 B2 | 5/2017 | Cohen et al. |
| 9,700,036 B1 | 7/2017 | Chatelain et al. |
| 9,700,037 B1 | 7/2017 | Chatelain et al. |
| 9,820,978 B2 | 11/2017 | Cohen et al. |
| 9,867,837 B2 | 1/2018 | Cohen et al. |
| 9,931,326 B2 | 4/2018 | Cohen et al. |
| 10,010,515 B2 | 7/2018 | Cohen et al. |
| 10,045,971 B2 | 8/2018 | Cohen et al. |
| 2006/0276411 A1 | 12/2006 | Simard et al. |
| 2009/0069419 A1 | 3/2009 | Jandeleit et al. |
| 2012/0115919 A1 | 5/2012 | Mueller et al. |
| 2017/0231958 A1 | 8/2017 | Cohen et al. |
| 2017/0273919 A1 | 9/2017 | Cohen et al. |
| 2018/0125867 A1 | 5/2018 | Cohen et al. |
| 2018/0263989 A1 | 9/2018 | Cohen et al. |
| 2018/0344711 A1 | 12/2018 | Cohen et al. |

FOREIGN PATENT DOCUMENTS

| | | |
|---|---|---|
| WO | 2008046014 A1 | 4/2008 |
| WO | 2009000406 A1 | 12/2008 |
| WO | 2009133128 A1 | 11/2009 |
| WO | 2009133142 A1 | 11/2009 |
| WO | 20090133141 A2 | 11/2009 |
| WO | 2010085352 A2 | 7/2010 |
| WO | 2012117075 A2 | 9/2012 |
| WO | 2014037416 A2 | 3/2014 |
| WO | 2015028659 A1 | 3/2015 |
| WO | 2016030522 A1 | 3/2016 |

OTHER PUBLICATIONS

Sawyer, G. T. "Treatment of Multiple Sclerosis with Tolbutamide" JAMA, Oct. 1, 1960, pp. 470-473, vol. 174, No. 5.

Yoshitake, I. et at. "First Clinical Application of the DuraHeart Centrifugal Ventricular Assist Device for a Japanese Patient" Artifical Organs, Sep. 1, 2009, pp. 763-766, vol. 33, No. 9.

Unger, R. H. et al., "Tolbutamide-Phenformin in Ketoacdosis-Resistant Patients", JAMA, Dec. 24, 1960, pp. 2132-2136, vol. 174, No. 17.

Satyanarayana, S. et al. "Pharmacodynamic and Pharmacokinetic Drug Interaction of Mexiletine with Tolbutamide in Rabbits" Indian Journal of Pharmaceutical Education and Research, Jan. 1, 2011, pp. 40-45, vol. 45, No. 1.

Wing, L. M. H. et al. "Cotrimoxazole as an inhibitor of oxidative drug metabolism: effects of trimethoprim and sulphamethoxazole separately and combined on tolbutamide disposition" Br. J. Clin. Pharmac. Nov. 1, 1985, pp. 482-485, vol. 20, No. 5.

Nistico, R. et al. "The blockade of K+-ATP channels has neuroprotective effects in an in vitro model of brainischemia" International Review of Neurobiology, 2007, pp. 383-395, vol. 82.

Zhao W. et al. "Identification of Antihypertnsive Drugs Which Inhibit Amyloid-beta-Protein Oligomerization" Journal of Alzheimer's Disease, 2009, pp. 49-57, vol. 16, No. 1.

Database WPI, Thomason Scientific, Accession No. 2007-663193, Feb. 11, 2009, XPQ02661053, pp. 1-10.

Egashira, N. et al. "Mexiletine Reverses Oxaliplatin-Induced Neuropathic Pain in Rats" J Pharmacol Sci, Jan. 1, 2010, pp. 473-476, vol. 112, No. 4.

Lee, K. H. et al. "Neuroprotective effects of mexiletine on motor evoked potentials in demyelinated rat spinal cords" Neuroscience Research, May 1, 2010, pp. 59-64, vol. 67, No. 1.

Ates, O. et al. "Neuroprotective effect of mexiletine in the central nervous system of diabetic rats" Molecular and Cellular Biochemistry, Mar. 16, 2006, pp. 125-31, vol. 286, No. 1-2.

Hewitt, K. E. et al. "The use-dependent sodium channel blocker mexiletine is neuroprotective against global schemic injury" Brain Research, Apr. 20, 2001, pp. 281-287, vol. 898, No. 2.

Kaptanoglu, E. et al. "Mexiletine treatment-induced inhibition of caspase-3 activation and improvement of behavioral recovery after spinal cord injury" J Neurosurg: Spine, Jul. 1, 2005, pp. 53-56, vol. 3.

Nishiyama, K. et al. "Mexiletine for Painful Alcoholic Neuropathy" Internal Medicine, Jun. 1, 1995, pp. 577-579, vol. 34, No. 6.

Kapural, L. et al."Intrathecal Ziconotide for Complex Regional Pain Syndrome: Seven Case Reports" Pain Practice, Jun. 4, 2009, pp. 296-303, vol. 9, No. 4.

Kuyumcu, M.E. et al. "Alzheimer's Disease Is Associated with a Low Prevalence of Hypertension" Dementia and Geriatric Cognitive Disorders, 2012, pp. 6-10, vol. 33.

Lieberman, A."Shaking Up Parkinson Disease: Fighting Like a Tiger, Thinking Like a Fox: a Book for the Puzzled, the Hopeful, the Willing, and the Prepared" 2002, p. 15, Ch. 1.

Larner, A.J. "A Dictionary of Neurological Sign" 2006, pp. 1-348 (see, pp. 239-241, definition of Parkinsonism, and pp. 291-292, definition of Spasticity),2nd Edition.

Marco, E. et al. "Is botulinum toxin type A effective in the treatment of spastic shoulder pain in patients after stroke? A double-blind randomized clinical trial" Journal of Rehabilitation Medicine, 2007, pp. 440-447, vol. 39.

Jack Jr., C. R. et al. "Medial temporal atrophy on MRI in normal aging and very mild Alzheimer's disease" Neurology, Sep. 1997, pp. 1-18, vol. 49, No. 3.

Montastruc, J. L. et al. "Parkinson's disease and hypertension: chronic bromocriptine treatment" Neurology, Nov. 1985, p. 1, vol. 35, No. 11, Abstract only.

"Review: could Torasemide cause Seizure disorder (Epilepsy)?" http://www.ehealthme.com/ds/torasemide/seizure+disorder. retrieved from the Internet Dec. 31, 2015, pp. 1-5.

Bliss, C. I."The Toxicity of Poisons Applied Jointly" Annals of Applied Biology, Aug. 1939, pp. 585-615, vol. 26, No. 3.

Foucquier, J. et al. "Analysis of drug combinations: current methodological landscape" Pharmacology Research & Perspectives, 2015, pp. 1-11, vol. 3, No. 3.

Dey, N. S. et al. "Multiparticulate Drug Delivery Systems for Controlled Release" Tropical Journal of Pharmaceutical Research, Sep. 2008, pp. 1067-1075, vol. 7, No. 3.

Yin, N. et al. "Synergistic and Antagonistic Drug Combinations Depend on Network Topology" Plos One, Apr. 2014, pp. 1-7, vol. 9, No. 4.

Larner, A. J. "A Dictionary of Neurological Signs" Second Edition, 2006, pp. 1-348.

Fisher, R. S. "Medications That Can Provoke Seizures" Epilepsy Therapy Project, Jul. 1, 2009, pp. 1-6.

\* cited by examiner

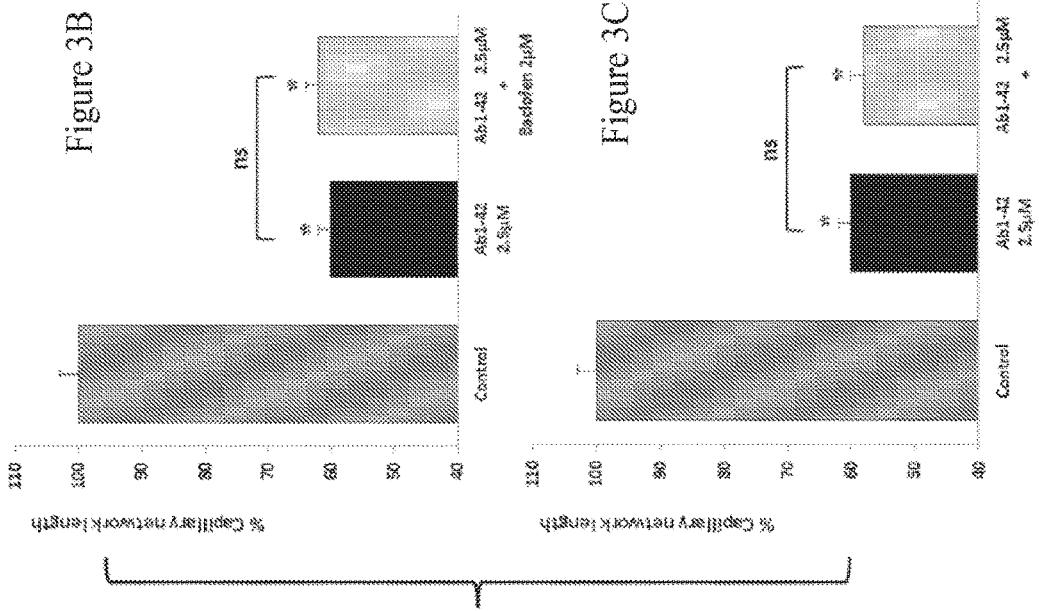
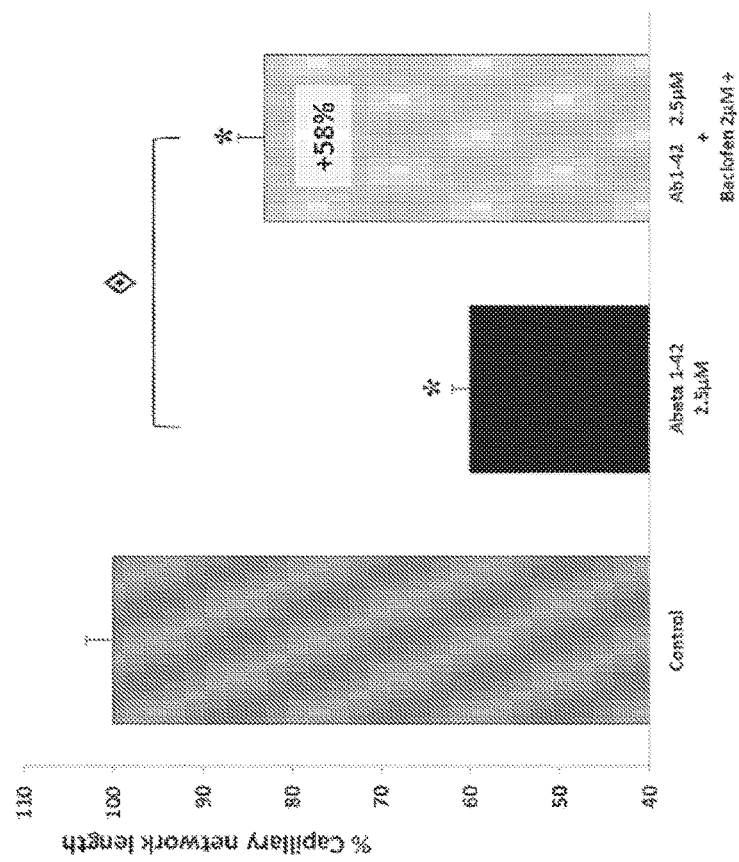
Figure 3A
Figure 3B
Figure 3C

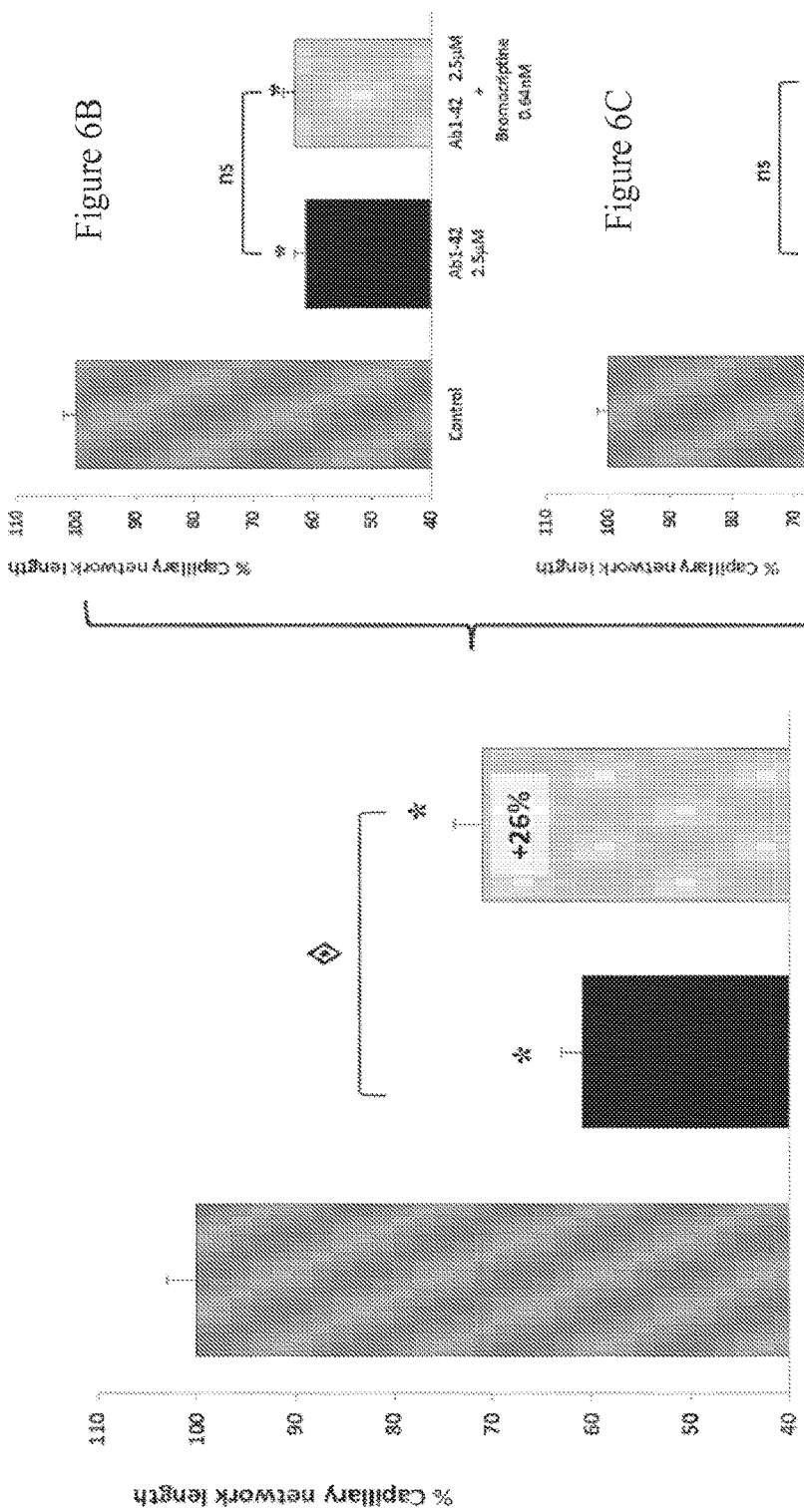
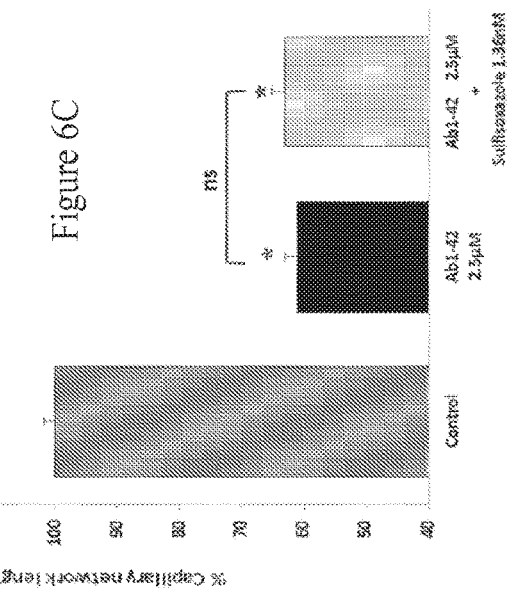
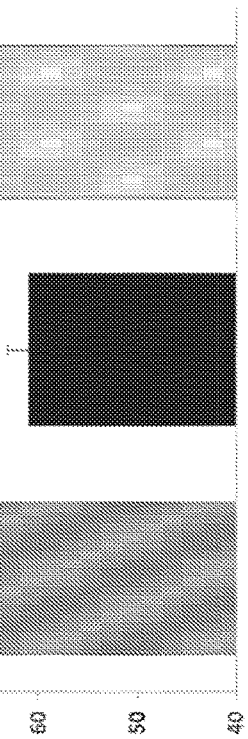

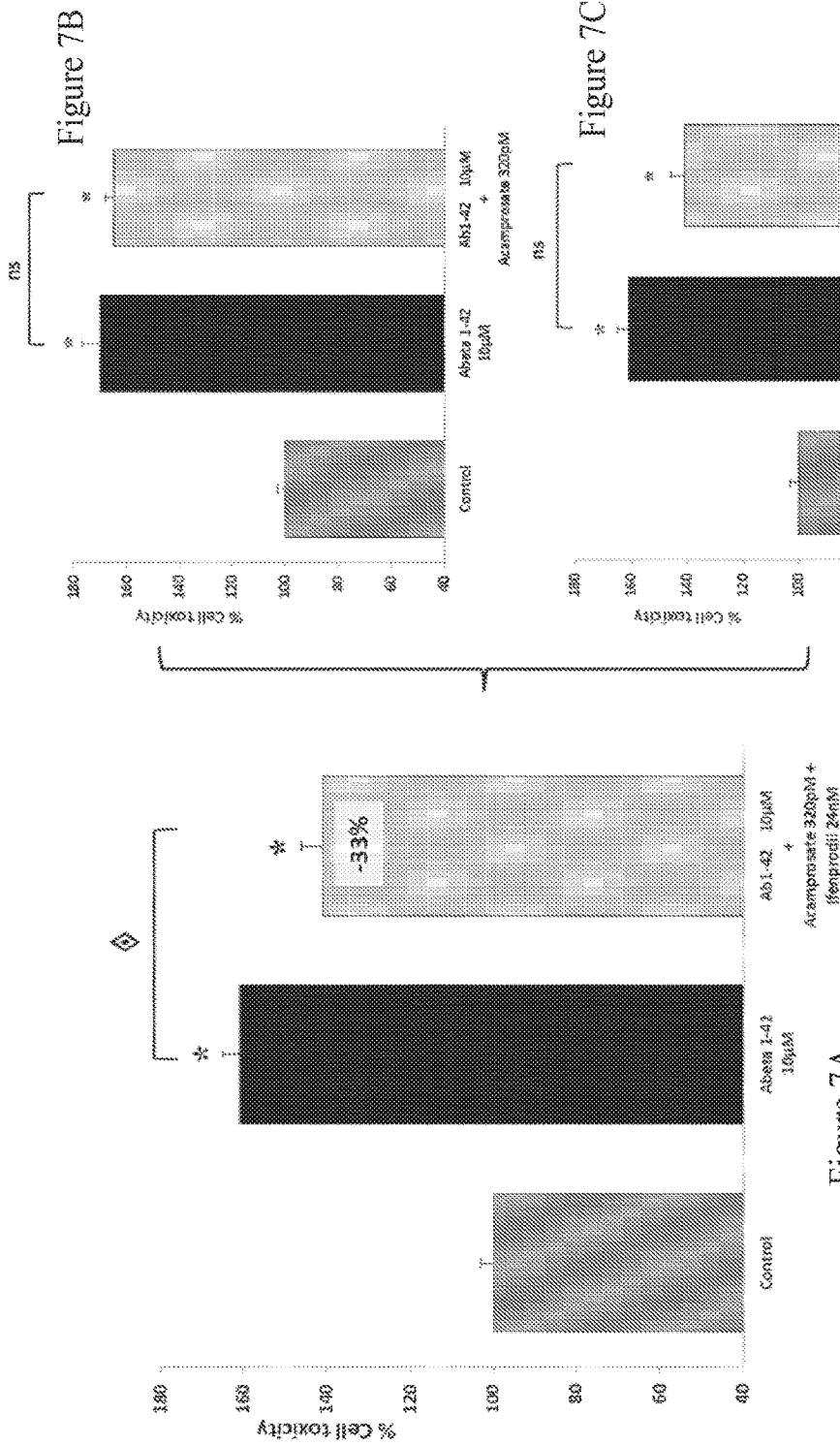

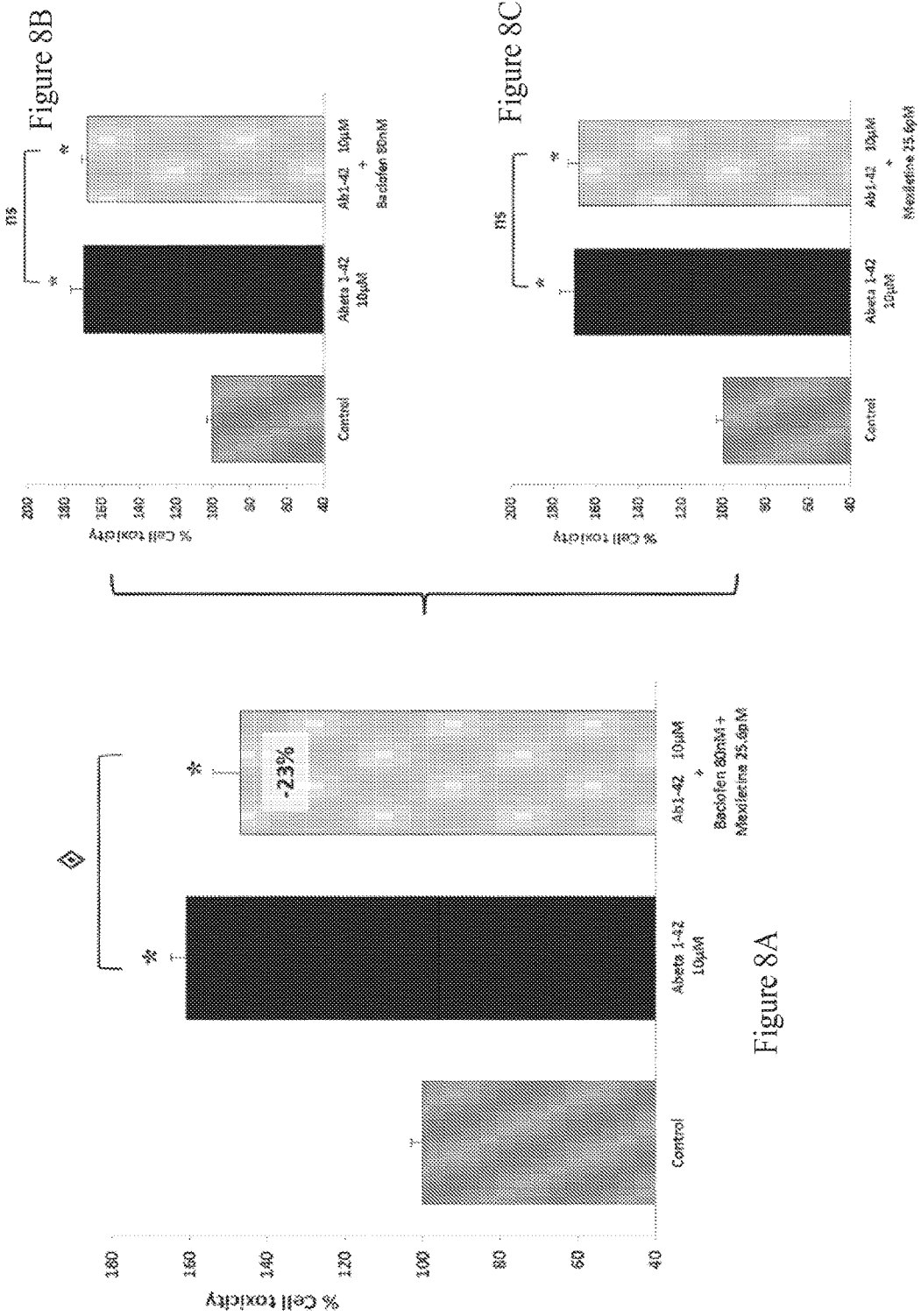

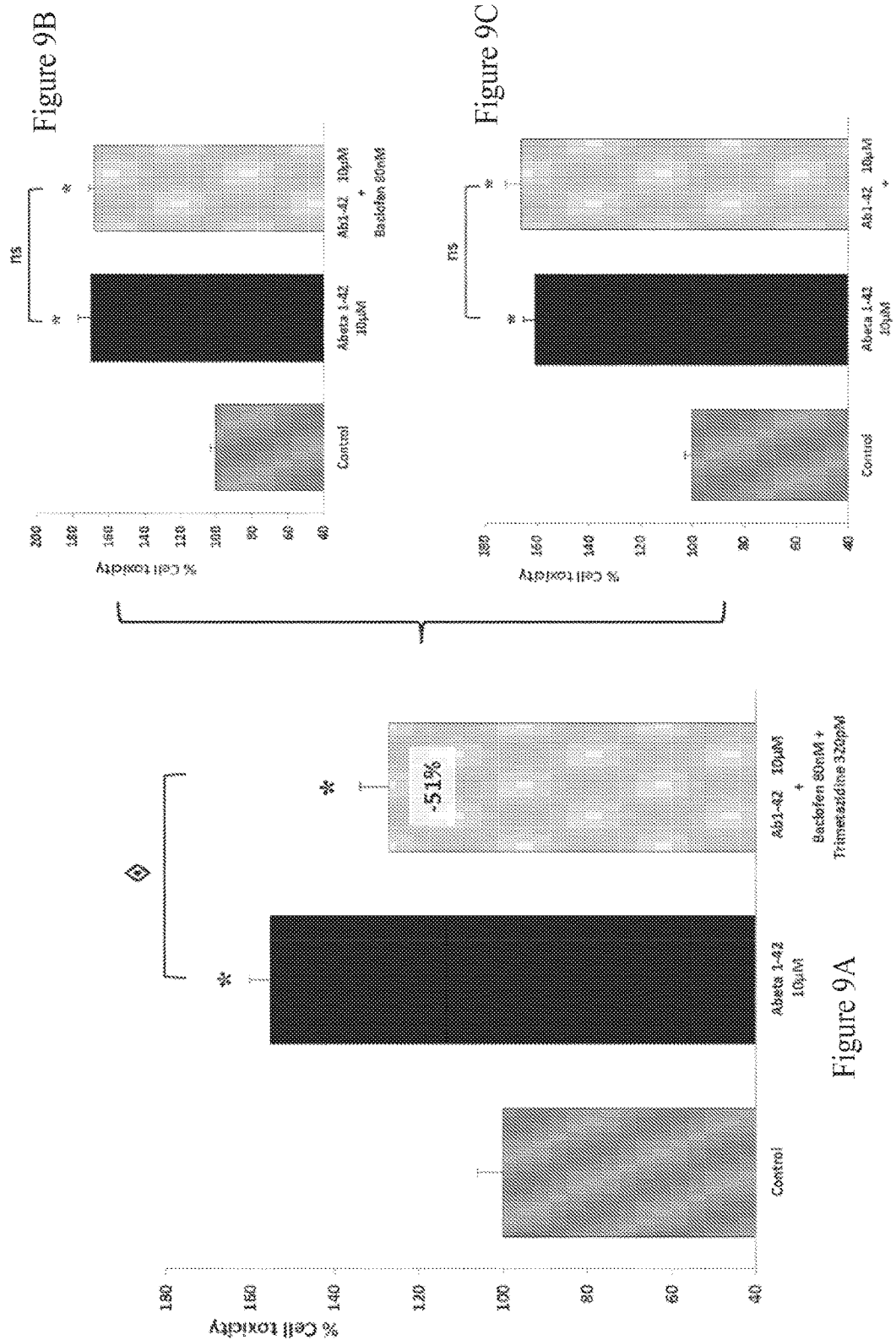

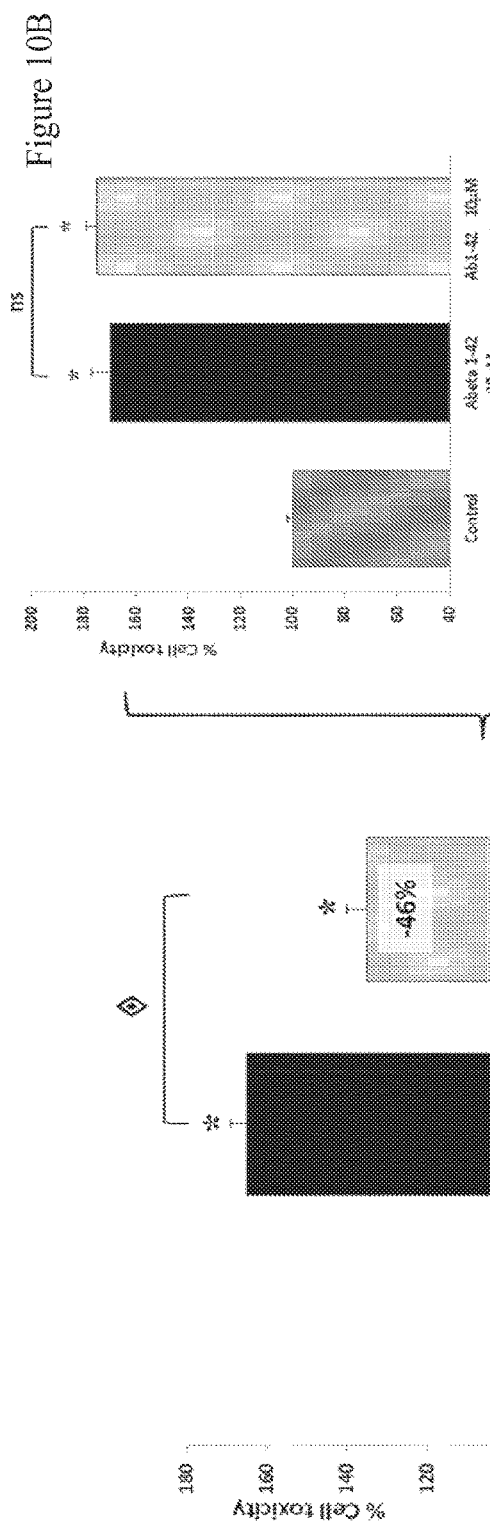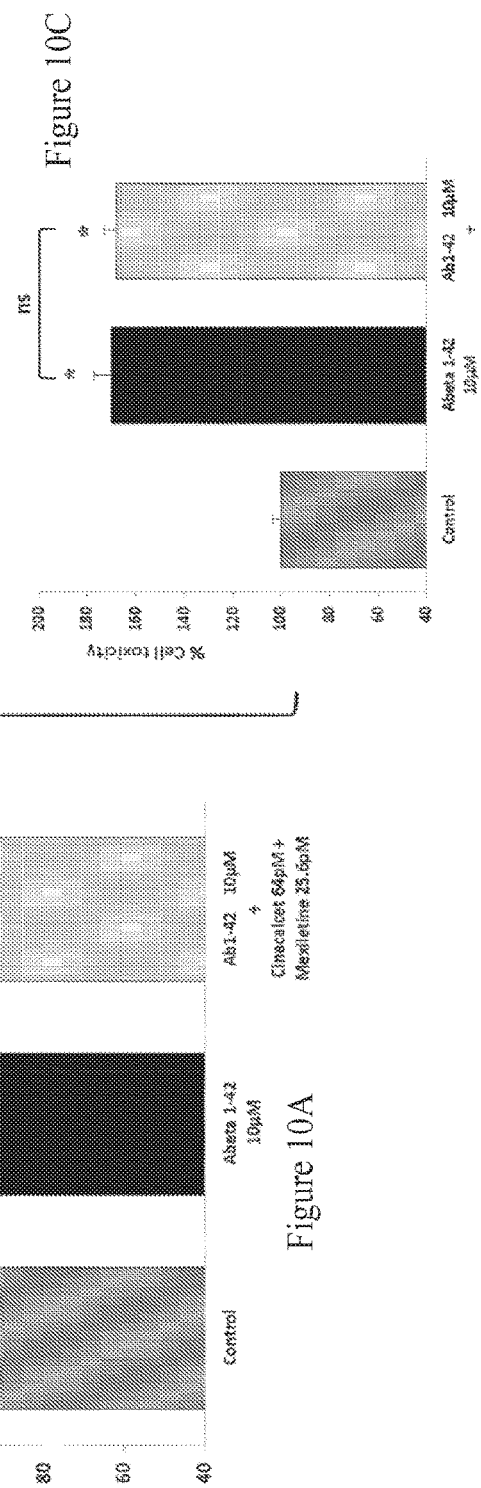

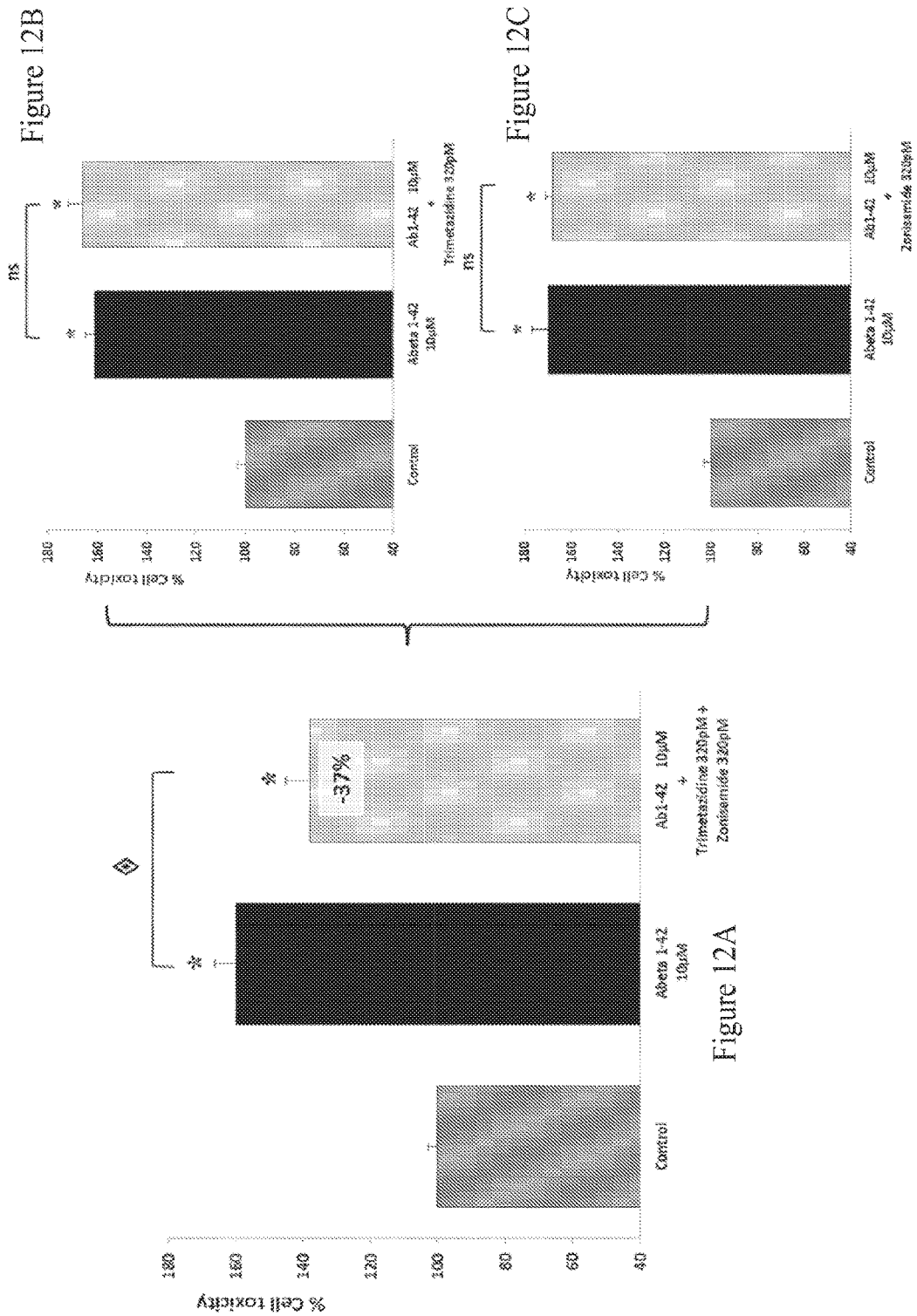

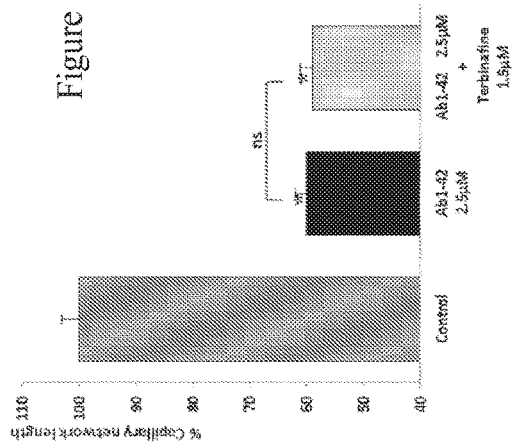
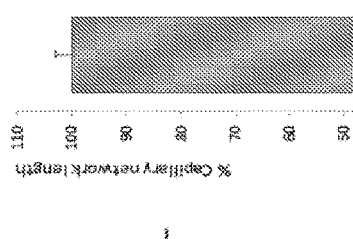
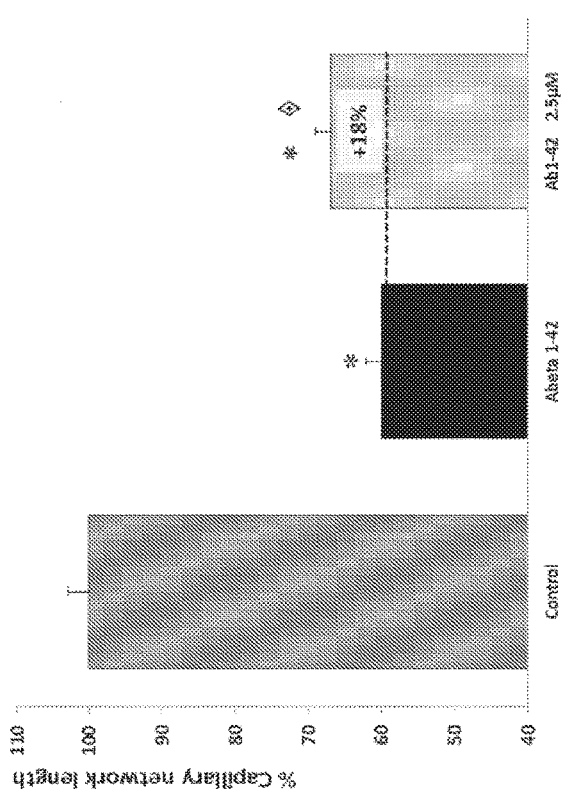
Figure 13A
Figure 13B
Figure 13C

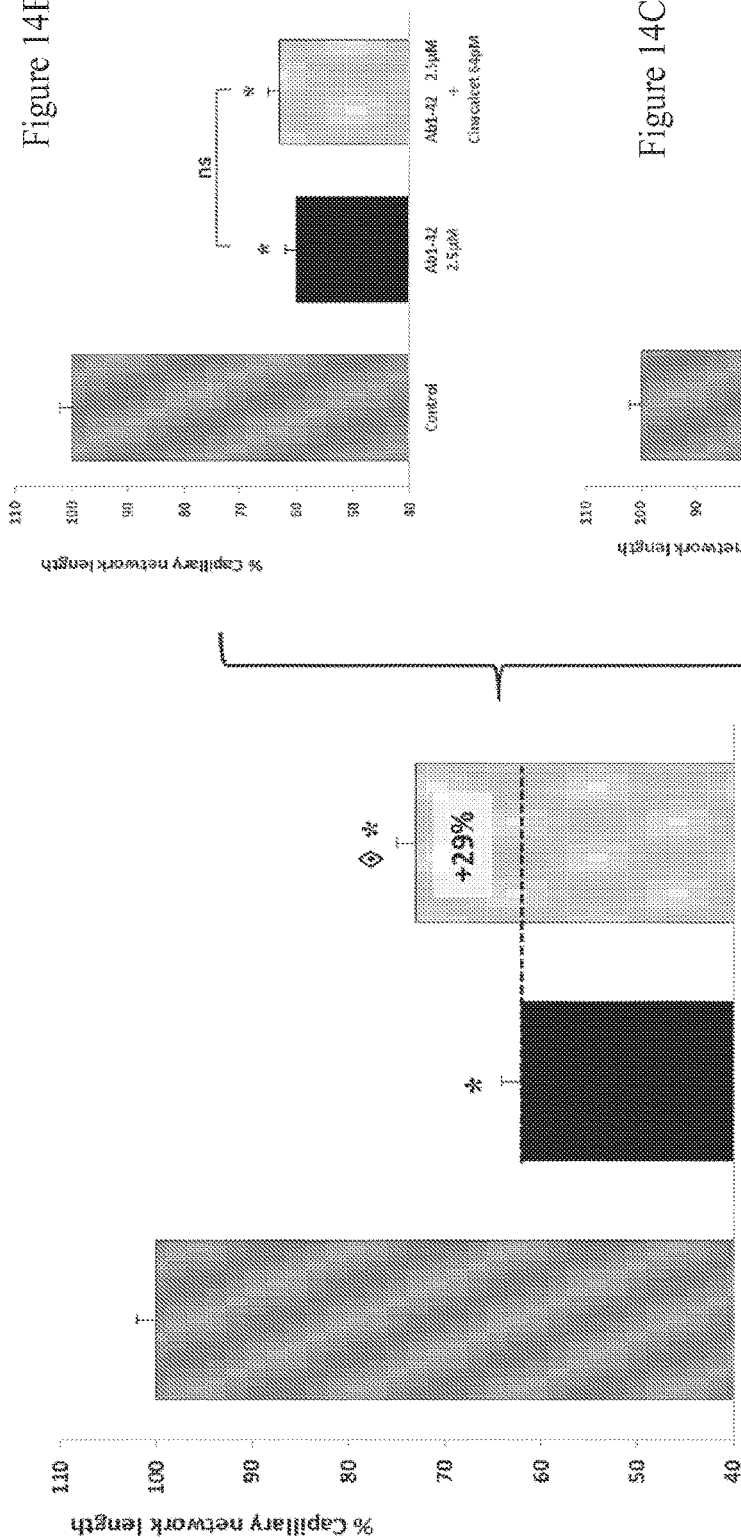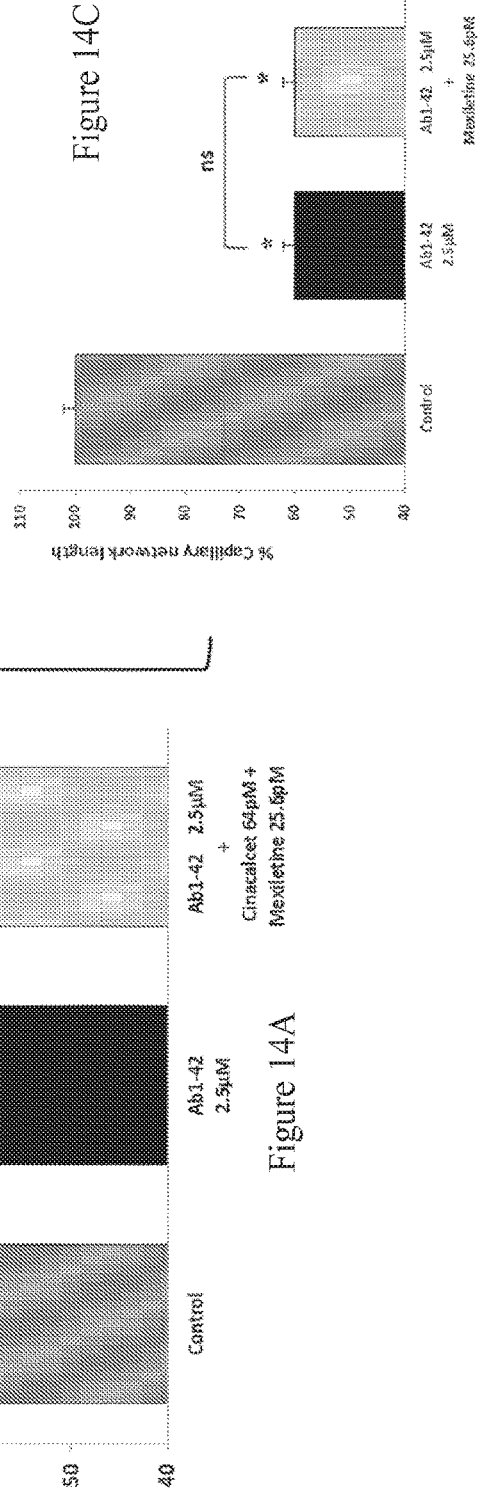
Figure 14A
Figure 14B
Figure 14C

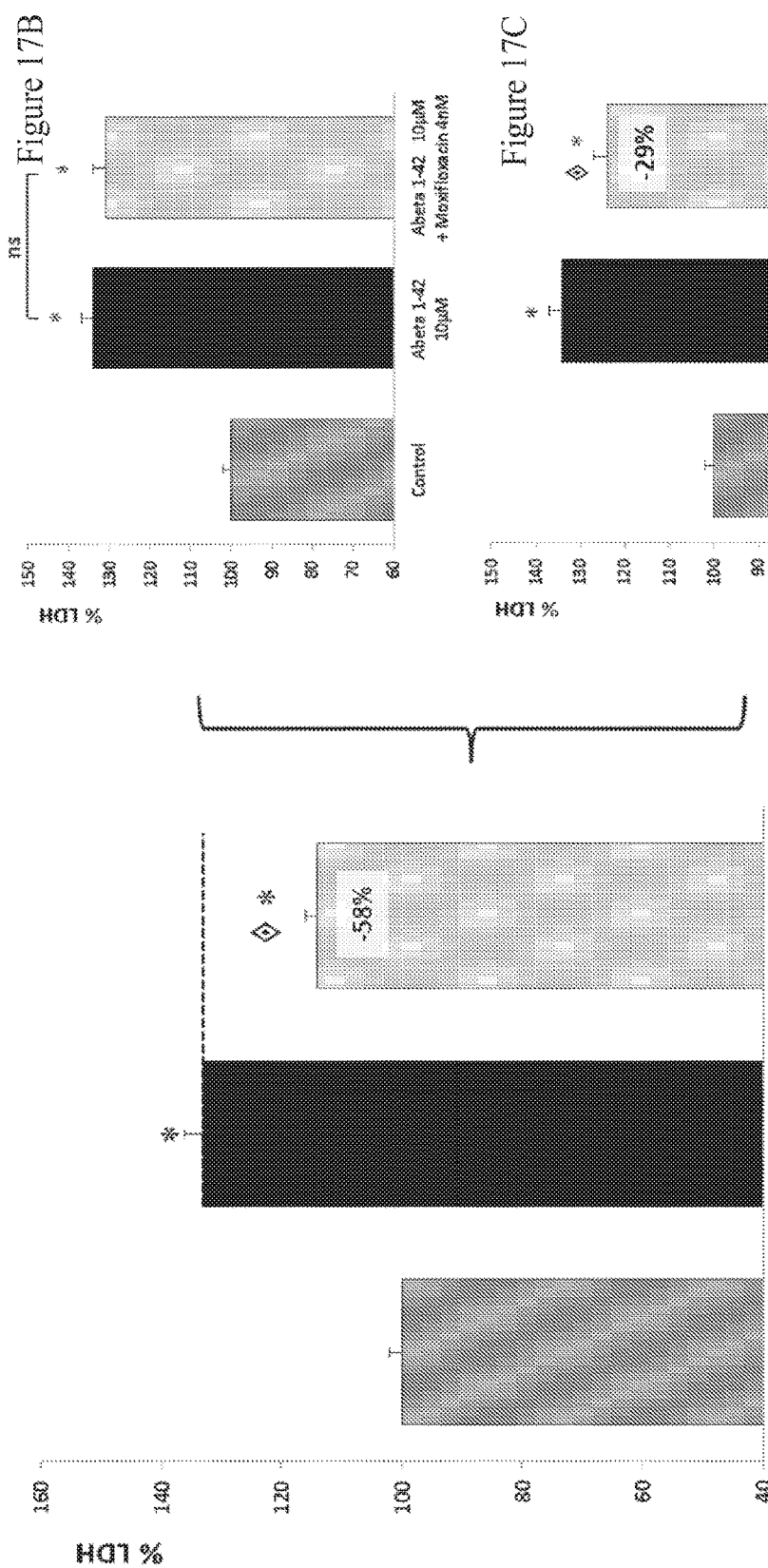

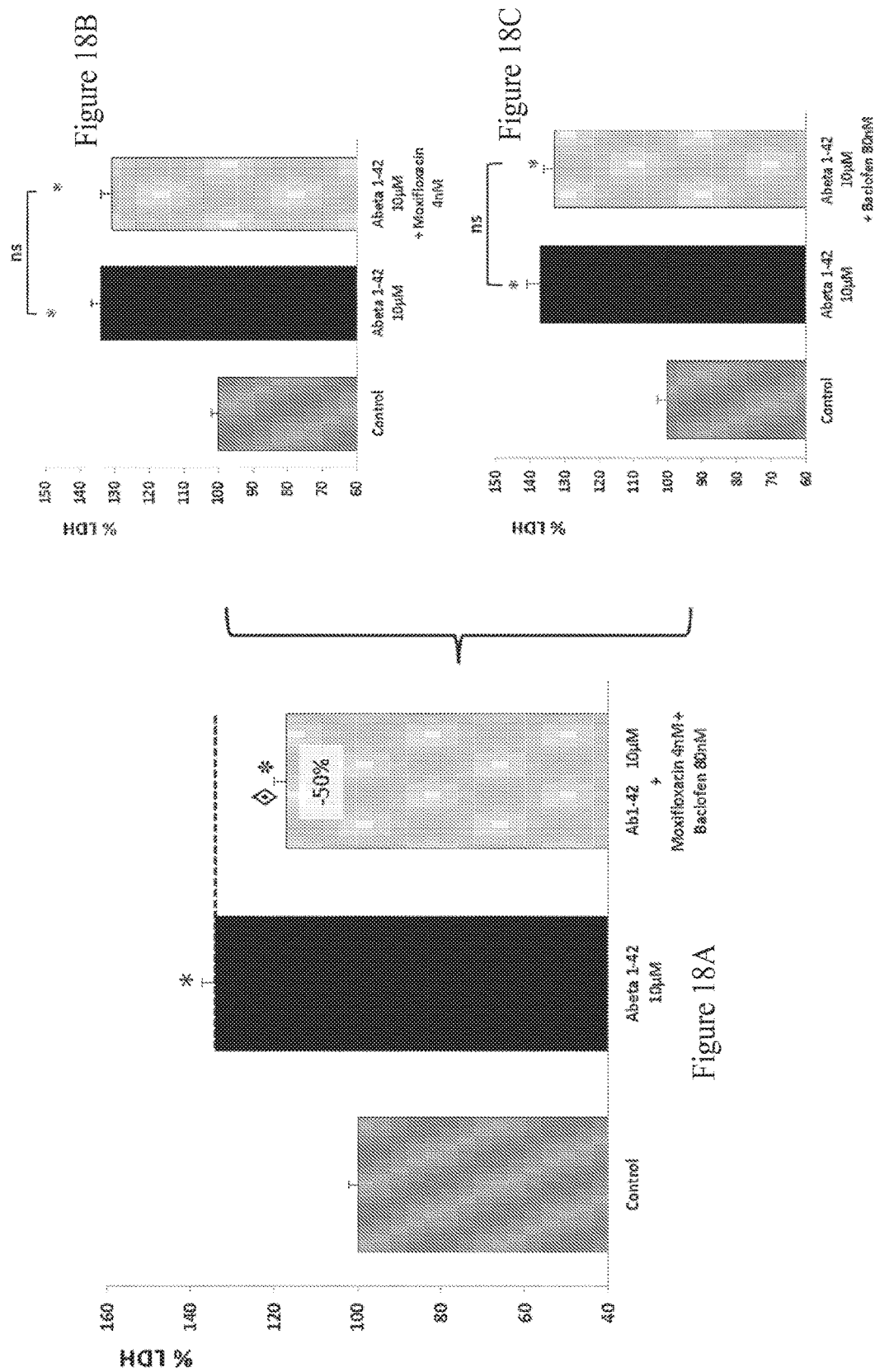

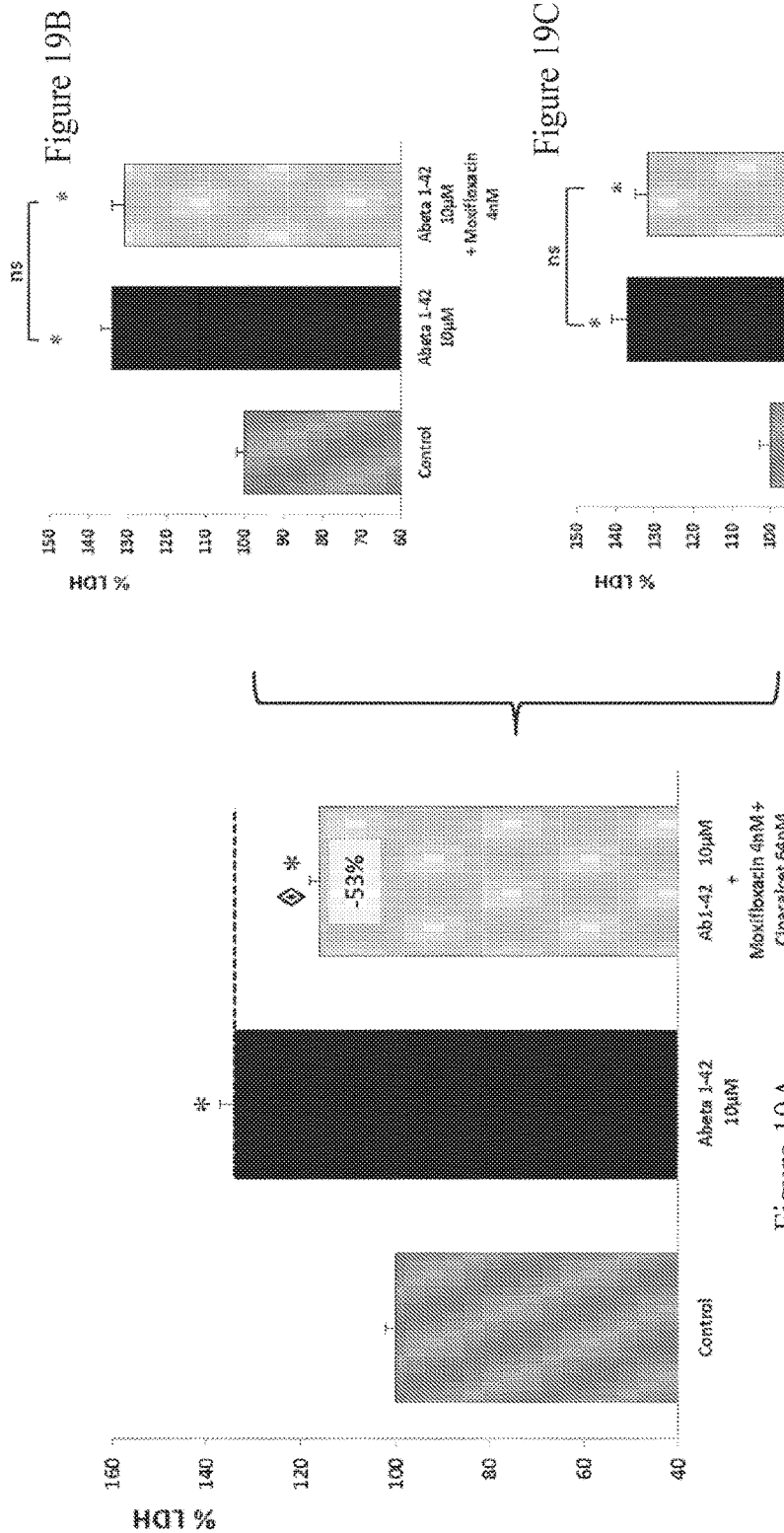

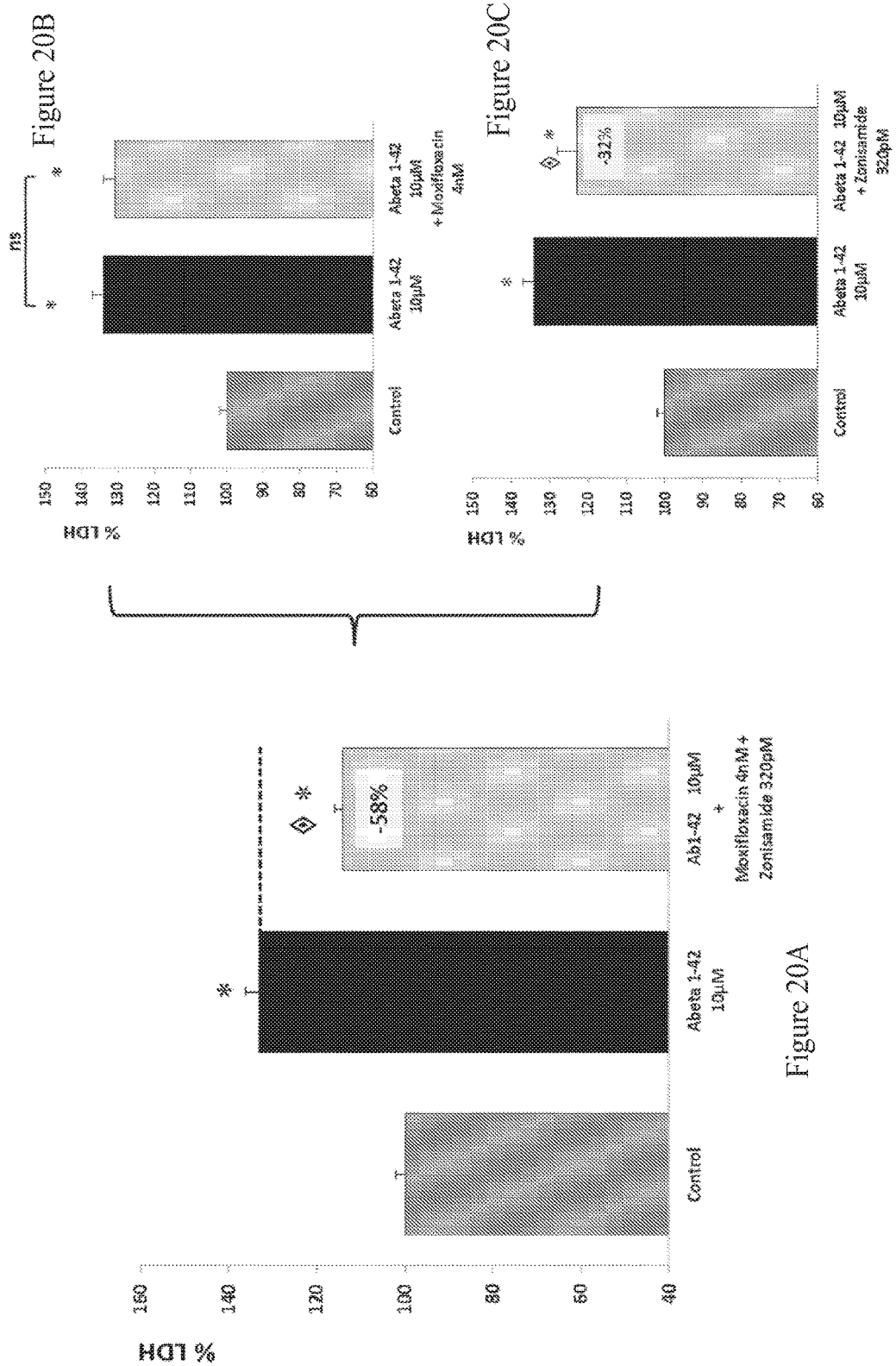

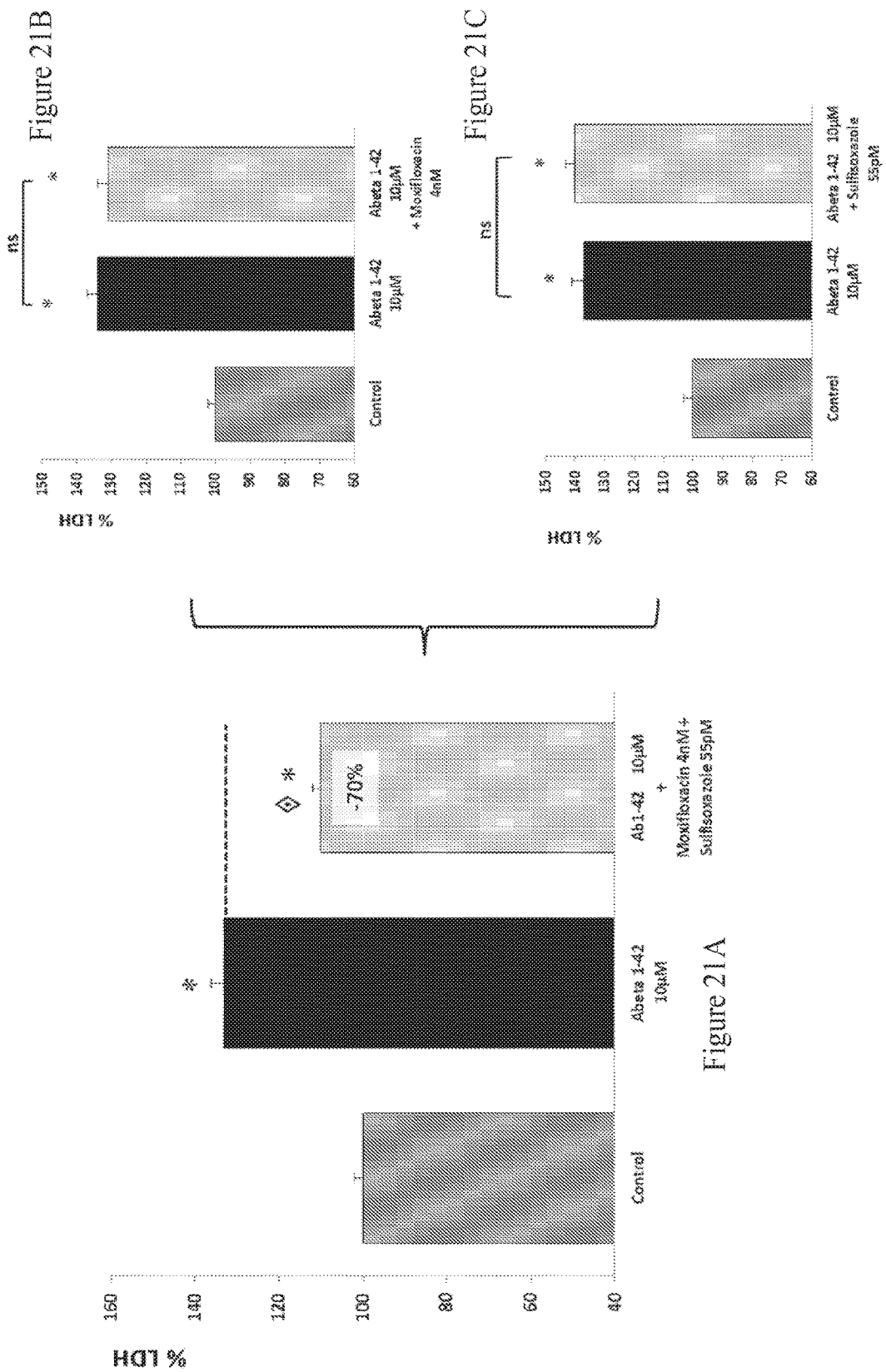

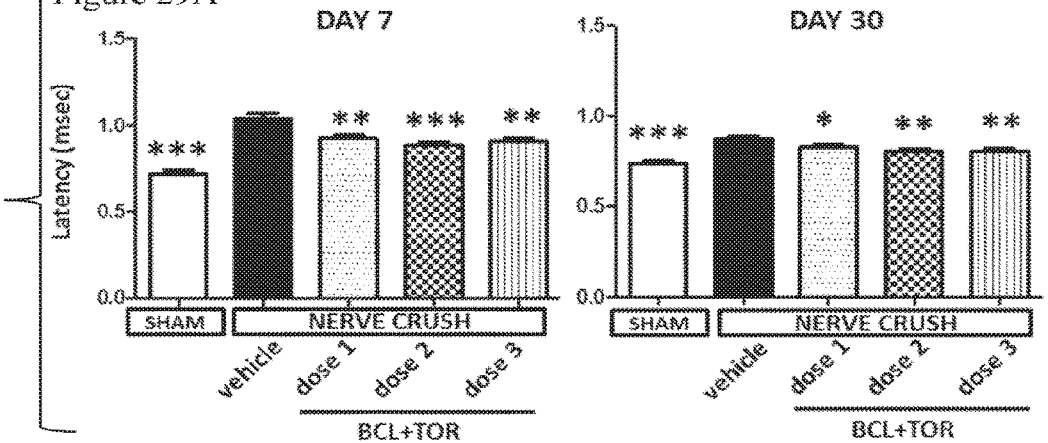
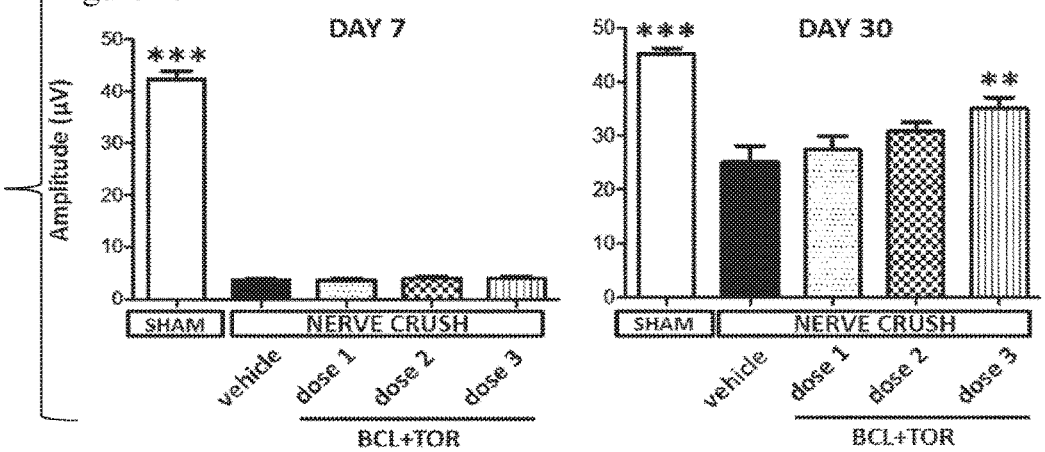

US 10,434,109 B2

SEQUENCE LISTING

<160> NUMBER OF SEQ ID NOS: 1

<210> SEQ ID NO 1
<211> LENGTH: 21
<212> TYPE: PRT
<213> ORGANISM: Mus musculus

<400> SEQUENCE: 1

```
Met Glu Val Gly Trp Tyr Arg Ser Pro Phe Ser Arg Val Val His Leu
1               5                   10                  15

Tyr Arg Asn Gly Lys
            20
```

COMPOSITIONS FOR TREATING NEUROLOGICAL DISORDERS

FIELD OF THE INVENTION

The present invention relates to compositions and methods for the treatment of neurological diseases and disorders. More particularly, this invention relates to novel combinatorial therapies for such diseases, including Alzheimer's and related diseases, Multiple Sclerosis, Amyotrophic Lateral Sclerosis, Parkinson's disease, neuropathies, alcoholism, alcohol withdrawal, Huntington's disease and spinal cord injury.

BACKGROUND OF THE INVENTION

Alzheimer's disease (AD) is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (ability to recognize objects, persons, sounds, shapes, or smells) attributable to involvement of the cortical association areas (1-4).

AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis (5).

The incidence rate of AD increases dramatically with age. United Nation population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources (6). Memory impairment is the early feature of the disease and involves episodic memory (memory for day-today events). Semantic memory (memory for verbal and visual meaning) is involved later in the disease. The pathological hallmark of AD includes amyloid plaques containing beta-amyloid (Abeta), neurofibrillary tangles (NFT) containing Tau and neuronal and synaptic dysfunction and loss (7-9). For the last decade, two major hypotheses on the cause of AD have been proposed: the "amyloid cascade hypothesis", which states that the neurodegenerative process is a series of events triggered by the abnormal processing of the Amyloid Precursor Protein (APP) (10), and the "neuronal cytoskeletal degeneration hypothesis" (11), which proposes that cytoskeletal changes are the triggering events. The most widely accepted theory explaining AD progression remains the amyloid cascade hypothesis (12-14) and AD researchers have mainly focused on determining the mechanisms underlying the toxicity associated with Abeta proteins. Microvascular permeability and remodeling, aberrant angiogenesis and blood brain barrier breakdown have been identified as key events contributing to the APP toxicity in the amyloid cascade (15). On contrary, Tau protein has received much less attention from the pharmaceutical industry than amyloid, because of both fundamental and practical concerns. Moreover, synaptic density change is the pathological lesion that best correlates with cognitive impairment than the two others.

Studies have revealed that the amyloid pathology appears to progress in a neurotransmitter-specific manner where the cholinergic terminals appear most vulnerable, followed by the glutamatergic terminals and finally by the GABAergic terminals (9). Glutamate is the most abundant excitatory neurotransmitter in the mammalian nervous system. Under pathological conditions, its abnormal accumulation in the synaptic cleft leads to glutamate receptors overactivation (16). Abnormal accumulation of glutamate in synaptic cleft leads to the overactivation of glutamate receptors that results in pathological processes and finally in neuronal cell death. This process, named excitotoxicity, is commonly observed in neuronal tissues during acute and chronic neurological disorders.

It is becoming evident that excitotoxicity is involved in the pathogenesis of multiple disorders of various etiology such as: spinal cord injury, stroke, traumatic brain injury, hearing loss, alcoholism and alcohol withdrawal, alcoholic neuropathy, or neuropathic pain as well as neurodegenerative diseases such as multiple sclerosis, Alzheimer's disease, Amyotrophic Lateral Sclerosis, Parkinson's disease, and Huntington's disease (17-19). The development of efficient treatment for these diseases remains major public health issues due to their incidence as well as lack of curative treatments.

NMDAR antagonists that target various sites of this receptor have been tested to counteract excitotoxicity. Uncompetitive NMDAR antagonists target the ion channel pore thus reducing the calcium entry into postsynaptic neurons. Some of them reached the approval status. As an example, Memantine is currently approved in moderate to severe Alzheimer's disease. It is clinically tested in other indications that include a component of excitotoxicity such as alcohol dependence (phase II), amyotrophic lateral sclerosis (phase III), dementia associated with Parkinson (Phase II), epilepsy, Huntington's disease (phase IV), multiple sclerosis (phase IV), Parkinson's disease (phase IV) and traumatic brain injury (phase IV). This molecule is however of limited benefit to most Alzheimer's disease patients, because it has only modest symptomatic effects. Another approach in limiting excitotoxicity consists in inhibiting the presynaptic release of glutamate. Riluzole, currently approved in amyotrophic lateral sclerosis, showed encouraging results in ischemia and traumatic brain injury models (20-23). It is at present tested in phase II trials in early multiple sclerosis, Parkinson's disease (does not show any better results than placebo) as welt as spinal cord injury. In 1995, the drug reached orphan drug status for the treatment of amyotrophic lateral sclerosis and in 1996 for the treatment of Huntington's disease.

WO2009/133128, WO2009/133141, WO2009/133142, and WO2011/054759, disclose molecules which can be used in compositions for treating neurological disorders.

Despite active research in this area, there is still a need for alternative or improved efficient therapies for neurological disorders, and, in particular, neurological disorders which are related to glutamate and/or amyloid beta toxicity. The present invention provides new treatments for such neurological diseases of the central nervous system (CNS) and the peripheral nervous system (PNS).

SUMMARY OF INVENTION

An object of the present invention is to provide new therapeutic approaches for treating neurological disorders.

The invention stems, inter alia, from the unexpected discovery by the inventors that Torasemide, Trimetazidine, Mexiletine, Bromocriptine, Ifenprodil and Moxifloxacin, alone or in combinations, represent new and effective therapies for the treatment of neurological disorders.

The invention therefore provides novel compositions and methods for treating neurological disorders, particularly AD and related disorders, Multiple Sclerosis (MS), Amyotrophic Lateral Sclerosis (ALS), Parkinson's disease (PD), neuropathies (for instance neuropathic pain or alcoholic neuropathy), alcoholism or alcohol withdrawal, damages to the peripheral nervous system, Huntington's disease (HD) and spinal cord injury.

More particularly, the invention relates to a composition, for use in the treatment of a neurological disorder, comprising at least Torasemide, Trimetazidine, Mexiletine, Ifenprodil, Moxifloxacin or Bromocriptine, or a salt, prodrug, derivative, or sustained release formulation thereof.

A further object of the present invention relates to a composition comprising at least one first compound selected from the group consisting of Torasemide, Trimetazidine, Mexiletine, Ifenprodil, Moxifloxacin, and Bromocriptine, or a salt, prodrug, derivative of any chemical purity, or sustained release formulation thereof, in combination with at least one second compound distinct from said first compound, selected from Sulfisoxazole, Methimazole, Prilocaine, Dyphylline, Quinacrine, Carbenoxolone, Acamprosate, Aminocaproic acid, Baclofen, Cabergoline, Diethylcarbamazine, Cinacalcet, Cinnarizine, Eplerenone, Fenoldopam, Leflunomide, Levosimendan, Sulodexide, Terbinafine, Zonisamide, Etomidate, Phenformin, Trimetazidine, Mexiletine, Bromocriptine, Ifenprodil, Torasemide, and Moxifloxacin salts, prodrugs, derivatives of any chemical purity, or sustained release formulation thereof, for simultaneous, separate or sequential administration.

A further object of the present invention relates to a composition, for use in the treatment of a neurological disorder, comprising at least one first compound selected from the group consisting of Torasemide, Trimetazidine, Mexiletine, Ifenprodil, Moxifloxacin, and Bromocriptine, salts, prodrugs, derivatives of any chemical purity, or sustained release formulation thereof, in combination with at least one second compound distinct from said first compound, selected from Sulfisoxazole, Methimazole, Prilocaine, Dyphylline, Quinacrine, Carbenoxolone, Acamprosate, Aminocaproic acid, Baclofen, Cabergoline, Diethylcarbamazine, Cinacalcet, Cinnarizine, Eplerenone, Fenoldopam, Leflunomide, Levosimendan, Sulodexide, Terbinafine, Zonisamide, Etomidate, Phenformin, Trimetazidine, Mexiletine, Bromocriptine, Ifenprodil, Torasemide, and Moxifloxacin, salts, prodrugs, derivatives of any chemical purity, or sustained release formulation thereof, for simultaneous, separate or sequential administration.

The present invention also relates to a composition comprising at least one first compound selected from the group consisting of Torasemide, Trimetazidine, Mexiletine, Ifenprodil, Moxifloxacin and Bromocriptine, salt(s), prodrug(s), derivative(s) of any chemical purity, or sustained release formulation(s) thereof, in combination with at least one second compound distinct from said first compound, selected from Sulfisoxazole, Methimazole, Prilocaine, Dyphylline, Quinacrine, Carbenoxolone, Acamprosate, Aminocaproic acid, Baclofen, Cabergoline, Diethylcarbamazine, Cinacalcet Cinnarizine, Eplerenone, Fenoldopam, Leflunomide, Levosimendan, Sulodexide, Terbinafine, Zonisamide, Etomidate, Phenformin, Trimetazidine, Mexiletine, Bromocriptine, Ifenprodil, Torasemide, and Moxifloxacin salt(s), prodrug(s), derivative(s) of any chemical purity, or sustained release formulation(s) thereof, and a pharmaceutically acceptable excipient, for simultaneous, separate or sequential administration.

Most preferred drug compositions comprise 1, 2, 3, 4 or 5 distinct drugs, even more preferably 2, 3 or 4. Furthermore, the above drug compositions may also be used in further combination with one or several additional drugs or treatments beneficial to subjects with a neurological disorder.

The invention also relates to a method of treating a neurological disorder, the method comprising administering to a subject in need thereof a drug or composition as disclosed above.

A further object of this invention relates to a method of treating a neurological disorder, the method comprising simultaneously, separately or sequentially administering to a subject in need thereof a drug combination as disclosed above.

A further object of this invention relates to the use of at least one compound selected from the group consisting of Torasemide, Trimetazidine, Mexiletine, Ifenprodil, Bromocriptine and Moxifloxacin, or salt(s), prodrug(s), derivative(s) of any chemical purity, or sustained release formulation(s) thereof, for the manufacture of a medicament for the treatment of a neurological disorder.

A further object of this invention relates to the use of drug combinations disclosed above, for the manufacture of a medicament for the treatment of a neurological disorder.

The invention may be used in any mammalian subject, particularly human subject, at any stage of the disease.

BRIEF DESCRIPTION OF THE FIGURES

For FIGS. 1 to 27, *: $p<0.05$: significantly different from control (no intoxication); "ns": no significant effect (ANOVA+Dunnett's Post-Hoc test).

FIGS. 3A-3C: Effect of Baclofen and Torasemide combination therapy on the total length of capillary network in beta-amyloid intoxicated HBMEC cultures. The aggregated human amyloid peptide ($A\beta_{1-42}$ 2.5 μM) produces a significant intoxication, above 40%, compared to vehicle-treated cells. This intoxication is significantly prevented by the combination of Baclofen and Torasemide (A) whereas, at those concentrations, Baclofen (B) and Torasemide (C) alone have no significant effect on intoxication. ◆: $p<0.05$, significantly different from $A\beta_{1-42}$ intoxication.

FIGS. 6A-6C: Effect of Bromocriptine and Sulfisoxazole combination therapy on the total length of capillary network in beta-amyloid intoxicated HBMEC cultures. The aggregated human amyloid peptide ($A\beta_{1-42}$ 2.5 μM) produces a significant intoxication, above 40%, compared to vehicle-treated cells. This intoxication is significantly prevented by the combination of Bromocriptine and Sulfisoxazole (A) whereas, at those concentrations, Bromocriptine (B) and Sulfisoxazole (C) alone have no significant effect on intoxication. ◆: $p<0.05$, significantly different from $A\beta_{1-42}$ intoxication.

FIGS. 7A-7C: Effect of Acamprosate and Ifenprodil combination therapy on LDH release in human $A\beta_{1-42}$ toxicity on rat primary cortical cells. The aggregated human amyloid peptide ($A\beta_{1-42}$ 10 μM) produces a significant intoxication compared to vehicle-treated neurons. This intoxication is significantly prevented by the combination of Acamprosate and Ifenprodil (A) whereas, at those concentrations, Acamprosate (B) and Ifenprodil (C) alone have no significant effect on intoxication, ◆: $p<0.05$, significantly different from $A\beta_{1-42}$ intoxication.

FIGS. 8A-8C: Effect of Baclofen and Mexiletine combination therapy on LDH release in human $A\beta_{1-42}$ toxicity on rat primary cortical cells. The aggregated human amyloid peptide ($A\beta_{1-42}$ 10 μM) produces a significant intoxication compared to vehicle-treated neurons. This intoxication is significantly prevented by the combination of Baclofen and Mexiletine (A) whereas, at those concentrations, Baclofen (B) and Mexiletine (C) alone have no significant effect on intoxication, ◆: $p=0.051$, different from $A\beta_{1-42}$, intoxication.

FIGS. 9A-9C: Effect of Baclofen and Trimetazidine combination therapy on LDH release in human $A\beta_{1-42}$ toxicity on rat primary cortical cells. The aggregated human amyloid peptide ($A\beta_{1-42}$ 10 μM) produces a significant intoxication compared to vehicle-treated neurons. This intoxication is significantly prevented by the combination of Baclofen and Trimetazidine (A) whereas, at those concentrations, Baclofen (B) and Trimetazidine (C) alone have no significant effect on intoxication. ◆: $p<0.05$, significantly different from $A\beta_{1-42}$ intoxication.

FIGS. 10A-10C: Effect of Cinacalcet and Mexiletine combination therapy on LDH release in human $A\beta_{1-42}$ toxicity on rat primary cortical cells. The aggregated human amyloid peptide ($A\beta_{1-42}$ 10 μM) produces a significant intoxication compared to vehicle-treated neurons. This intoxication is significantly prevented by the combination of Cinacalcet and Mexiletine (A) whereas, at those concentrations, Cinacalcet (B) and Mexiletine (C) alone have no significant effect on intoxication. ◆: $p<0.05$, significantly different from $A\beta_{1-42}$ intoxication.

FIGS. 12A-12C: Effect of Trimetazidine and Zonisamide combination therapy on LDH release in human $A\beta_{1-42}$ toxicity on rat primary cortical cells. The aggregated human amyloid peptide ($A\beta_{1-42}$ 10 μM) produces a significant intoxication compared to vehicle-treated neurons. This intoxication is significantly prevented by the combination of Trimetazidine and Zonisamide (A) whereas, at those concentrations, Trimetazidine (B) and Zonisamide (C) alone have no significant effect on intoxication. ◆: $p<0.05$, significantly different from $A\beta_{1-42}$ intoxication.

FIGS. 13A-13C: Effect of Terbinafine and Torasemide combination therapy on the total length of capillary network in beta-amyloid intoxicated HBMEC cultures. The aggregated human amyloid peptide ($A\beta_{1-42}$ 2.5 μM) produces a significant intoxication, above 40%, compared to vehicle-treated cells. This intoxication is significantly prevented by the combination of Terbinafine and Torasemide (A) whereas, at those concentrations, Terbinafine (B) and Torasemide (C) alone have no significant effect on intoxication. ◆: $p<0.05$, significantly different from $A\beta_{1-42}$ intoxication.

FIGS. 14A-14C: Effect of Cinacalcet and Mexiletine combination therapy on the total length of capillary network in beta-amyloid intoxicated HBMEC cultures. The aggregated human amyloid peptide ($A\beta_{1-42}$ 2.5 μM) produces a significant intoxication, above 40%, compared to vehicle-treated cells. This intoxication is significantly prevented by the combination of Cinacalcet and Mexiletine (A) whereas, at those concentrations, Cinacalcet (B) and Mexiletine (C) alone have no significant effect on intoxication. ◆: $p<0.05$, significantly different from $A\beta_{1-42}$ intoxication.

FIGS. 17A-17C: Effect of Moxifloxacin and Trimetazidine combination therapy on LDH release in human A$\beta_{1-42}$ toxicity on rat primary cortical cells. The aggregated human amyloid peptide (A$\beta_{1-42}$ 10 µM) produces a significant intoxication compared to vehicle-treated neurons. This intoxication is significantly prevented by the combination of Moxifloxacin and Trimetazidine (A). Adjunction of Moxifloxacin allows an increase of 100% of the effect observed for Trimetazidine (C) alone, whereas, at the same concentration, Moxifloxacin (9) alone has no significant effect on intoxication. ◇: $p<0.05$, significantly different from A$\beta_{1-42}$ intoxication.

FIGS. 18A-18C: Effect of Moxifloxacin and Baclofen combination therapy on LDH release in human A$\beta_{1-42}$ toxicity on rat primary cortical cells. The aggregated human amyloid peptide (A$\beta_{1-42}$ 10 µM) produces a significant intoxication compared to vehicle-treated neurons. This intoxication is significantly prevented by the combination of Moxifloxacin and Baclofen (A) whereas, at those concentrations, Moxifloxacin (B) and Baclofen (C) alone have no significant effect on intoxication. ◇: $p<0.05$, significantly different from A$\beta_{1-42}$ intoxication.

FIGS. 19A-19C: Effect of Moxifloxacin and Cinacalcet combination therapy on LDH release in human A$\beta_{1-42}$ toxicity on rat primary cortical cells. The aggregated human amyloid peptide (A$\beta_{1-42}$ 10 µM) produces a significant intoxication compared to vehicle-treated neurons. This intoxication is significantly prevented by the combination of Moxifloxacin and Cinacalcet (A) whereas, at those concentrations, Moxifloxacin (B) and Cinacalcet (C) alone have no significant effect on intoxication. ◇: $p<0.05$, significantly different from A$\beta_{1-42}$ intoxication.

FIGS. 29A-20C: Effect of Moxifloxacin and Zonisamide combination therapy on LDH release in human A$\beta_{1-42}$ toxicity on rat primary cortical cells. The aggregated human amyloid peptide (A$\beta_{1-42}$ 10 µM) produces a significant intoxication compared to vehicle-treated neurons. This intoxication is significantly prevented by the combination of Moxifloxacin and Zonisamide (A). Adjunction of Moxifloxacin allows an increase of 81% of the effect observed for Zonisamide (C) alone, whereas, at the same concentration, Moxifloxacin (B) alone has no significant effect on intoxication. ◇: $p<0.05$, significantly different from A$\beta_{1-42}$ intoxication.

FIGS. 21A-21C: Effect of Moxifloxacin and Sulfisoxazole combination therapy on LDH release in human A$\beta_{1-42}$ toxicity on rat primary cortical cells. The aggregated human amyloid peptide (A$\beta_{1-42}$ 10 µM) produces a significant intoxication compared to vehicle-treated neurons. This intoxication is significantly prevented by the combination of Moxifloxacin and Sulfisoxazole (A) whereas, at those concentrations, Moxifloxacin (B) and Sulfisoxazole (C) alone have no significant effect on intoxication. ◇: $p<0.05$, significantly different from A$\beta_{1-42}$ intoxication.

FIGS. 29A-29B: Effect of Baclofen (BCL) and Torasemide (TOR) combination in promoting nerve regeneration after nerve crush. A—Animals experiencing nerve injury (nerve crush) treated with baclofen-torasemide combination show a significantly lower latency of CMAP upon stimulation of the injured sciatic nerve at day 7 and day 30 from nerve crush when compared to the sham operated animals (white bar) or to the vehicle treated animals. B—Amplitudes of the signal of muscular evoked potentials upon sciatic nerve stimulation are significantly lower in animals experiencing nerve injury when compared to the sham operated animals at both day 7 or day 30 from nerve crush. A significant increase in CMAP amplitude is observed at day 30 from nerve crush for the animals treated with baclofen (3 mg/kg)-torasemide (400 μg/kg) (dose 3) bid. *p<0.05; p<0.001; *p<0.0001, significantly different from vehicle treated animals (black bar).

DETAILED DESCRIPTION OF THE INVENTION

Figure 1A:
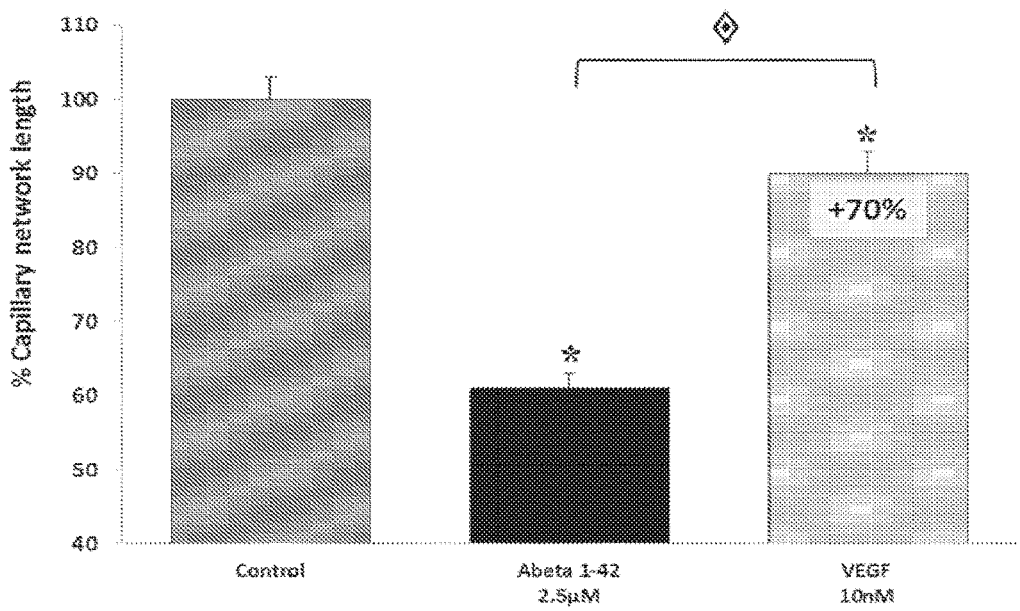
FIGS. 1A-1C: Effect of selected drugs pre-treatment against human $A\beta_{1-42}$ injury in HBMEC. A) Validation of the experimental model used for drug screening: 1 hr of VEGF pre-treatment at 10 nM significantly protected the capillary network from this amyloid injury (+70% of capillary network compared to amyloid intoxication). The intoxication is significantly prevented by Torasemide (B) and Bromocriptine (C) at doses as low as of 400 nM and 3.2 nM respectively, whereas no or a weaker effect is noticed for upper and lower doses. ◊: $p<0.05$: significantly different from Amyloid intoxication.

The present invention provides new compositions for treating neurological disorders. The invention discloses novel use of drugs or novel drug combinations which allow an effective correction of such diseases and may be used for patient treatment.

The invention is suited for treating any neurological disorder, whether central or peripheral, particularly disorders wherein amyloid or glutamate excitotoxicity are involved. Specific examples of such disorders include neurodegenerative diseases such as Alzheimer's and related disorders, Multiple Sclerosis (MS), Amyotrophic Lateral Sclerosis (ALS), Parkinson's Disease (PD), Huntington's Disease (HD), or other neurological disorders like neuropathies (for instance alcoholic neuropathy or neuropathic pain), alcoholism or alcohol withdrawal and spinal cord injury. "Neuropathies" refers to conditions where nerves of the peripheral nervous system are damaged, this include damages of the peripheral nervous system provoked by genetic factors, inflammatory disease, by chemical substance including drugs (vincristine, oxaliplatin, ethyl alcohol), or by a direct physical insult to the nerve. The treatment of neuropathies also includes the treatment of neuropathic pain.

Damages of the peripheral nervous system can be ranked according to the stage of neuronal insult. Invention is suited for treating nerve injuries ranking from neurapraxia (condition where only signalling ability of the nerve is impaired), axonometsis (injury implying damages to the axons, without impairing surrounding connective tissues of the nerves), but also neurotmesis (injury damaging both axon and surrounding tissues).

Alterations in axon or in surrounding tissues as myelin) can be of genetic origin. An example of inherited neuropathies is the so called Charcot Marie Tooth family of diseases. Charcot Marie Tooth diseases are progressive disorders that affect peripheral nerves which are distinguished by the specific gene(s) that is (are) altered, Mutation(s) result in an impairment of axons, which transmit nerve impulses, and/or affect the production myelin sheath by Shwann cells, which is implicated in the speed of the transmission of nervous impulse. There are several types (categorized as a function of clinical features) and subtypes of CMT (corresponding to a genetic classification). CMT types are CMT1, CMT2, CMT3, CMT/4, CMT5, CMT6, CMTDI, CMTRI, CMTX. Related peripheral neuropathies are, for example, HNPP (hereditary neuropathy with liability to pressure palsies), severe demyelinating neuropathies DSS (Dejerine-Sottas syndrome), GIN (congenital hypomyelinating neuropathy). CMT1 (a demyelinating type) and CMT2 (an axonal type) account for around 70% of the CMT patients.

The invention is particularly suited for treating AD and related disorders. In the context of this invention, the term. "AD related disorder" includes senile dementia of AD type (SDAT), Lewis body dementia, vascular dementia, mild cognitive impairment (MCI) and age-associated memory impairment (AAMI).

As used herein, "treatment" includes the therapy, prevention, prophylaxis, retardation or reduction of symptoms provoked by or of the causes of the above diseases or disorders. The term treatment includes in particular the control of disease progression and associated symptoms. The term treatment particularly includes i) a protection against the toxicity caused by Amyloid Beta, or a reduction or retardation of said toxicity, and/or ii) a protection against glutamate excitotoxicity, or a reduction or retardation of said toxicity, in the treated subjects. The term treatment also designates an improvement of cognitive symptom or a protection of neuronal cells. In relation to neuropathies, the term treatment also includes nerve regeneration, which encompasses remyelination, generation of new neurons, glia, axons, myelin or synapses.

Within the context of this invention, the designation of specific compounds is meant to include not only the specifically named molecules, but also any pharmaceutically acceptable salt, hydrate, derivatives (e.g., ester, ether), isomers, racemate, conjugates, or prodrugs thereof, of any purity.

The term "prodrug" as used herein refers to any functional derivatives (or precursors) of a compound of the present invention, which, when administered to a biological system, generates said compound as a result of e.g., spontaneous chemical reaction(s), enzyme catalyzed chemical reaction(s), and/or metabolic chemical reaction(s). Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Prodrugs typically have the structure X-drug wherein X is an inert carrier moiety and drug is the active compound, wherein the prodrug is less active than the drug and the drug is released from the carrier in vivo. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge (24-28). Furthermore, the preparation of prodrugs may be performed by conventional methods known by those skilled in the art. Methods which can be used to synthesize other prodrugs are described in numerous reviews on the subject (25; 29-35). For example, Arbaclofen Placarbil is listed in ChemID plus Advance database (http://chem.sis.nlm.nih.gov/chemidplus/) and Arbaclofen Placarbil is a well known prodrug of Baclofen (36; 43).

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, Homotaurine is a deacetylated derivative of Acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih- .gov/search/) or DrugBank (http://www.drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector (37-38) available online (http://www.ebi.ac.uk/thornton-srv/software/SMSD/). Preferred derivatives should be both structurally and functionally related to a parent compound, i.e., they should also retain at least part of the activity of the parent drug, more preferably they should have a protective activity against Aβ or glutamate toxicity.

The term derivatives also include metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, preferably that has a protective activity against Aβ toxicity or glutamate toxicity. Examples of metabolites include hydroxylated forms of Torasemide resulting from the hepatic metabolism of the drug (Drug bank database (39).

The term "salt" refers to a pharmaceutically acceptable and relatively non-toxic, inorganic or organic acid addition salt of a compound of the present invention. Pharmaceutical salt formation consists in pairing an acidic, basic or zwitterionic, drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as taught by H. Stahl and C. G Wermuth in their handbook (40).

The term "combination" or "combinatorial treatment/therapy" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

As disclosed in the examples, Torasemide, Trimetazidine, Mexiletine, Ifenprodil, Bromocriptine and Moxifloxacin have a strong unexpected effect on biological processes involved in neurological disorders. Furthermore, these compounds also showed in vivo a very efficient ability to correct symptoms of such diseases. These molecules, alone or in combination therapies, therefore represent novel approaches for treating neurological disorders, such as Alzheimer's disease, Multiple Sclerosis, Amyotrophic Lateral Sclerosis, Parkinson's Disease, Huntington's Disease, neuropathies (for instance neuropathic pain or alcoholic neuropathy), alcoholism or alcohol withdrawal, and spinal cord injury. Combinations of these drugs with other selected compounds (see Table 2) are particularly advantageous because they produce a surprising and unexpected synergistic effect at dosages where the drugs alone have essentially no effect. Also, because of their efficacy, the herein disclosed drugs combinations can be used at low dosages, which is a further very substantial advantage.

In this regard, in particular embodiment, the invention relates to a composition for use in the treatment of AD, AD related disorders, MS, PD, ALS, HD, neuropathies (for instance neuropathic pain or alcoholic neuropathy), alcoholism or alcohol withdrawal, or spinal cord injury, comprising at least Torasemide, Trimetazidine, Mexiletine, Ifenprodil, Bromocriptine, or Moxifloxacin, or a salt, prodrug, derivative, or sustained release formulation thereof.

The specific CAS number for each of these compounds is provided in Table 1 below. Table 1 cites also, in a non-limitative way, common salts, racemates, prodrugs, metabolites or derivatives for these compounds used in the compositions of the invention.

TABLE 1

| Drug | CAS Numbers | Class or Tanimoto similarity index |
| --- | --- | --- |
| Mexiletine and related compounds | | |
| Mexiletine | 31828-71-4; 5370-01-4 | |
| 6-Hydroxymethylmexiletine | 53566-98-6 | Metabolite |
| 4-Hydroxymexiletine | 53566-99-7 | Metabolite |
| 3-Hydroxymexiletine (MHM) | 129417-37-4 | Metabolite |
| N-Hydroxymexiletine glucuronide | 151636-18-9 | Metabolite |
| Sulfisoxazole and related compounds | | |
| Sulfisoxazole | 127-69-5; 4299-60-9 | |
| N(4)-Acetylsulfisoxazole | 4206-74-0 | Metabolite |
| Sulfisoxazole acetyl | 80-74-0 | Prodrug |
| Sulfamethoxazole | 723-46-6 | 0.52 |
| Cinacalcet and related compounds | | |
| Cinacalcet | 226256-56-0; 364782-34-3 | |
| Hydrocinnamic acid | 501-52-0 | Metabolite |
| Torasemide and related compounds | | |
| Torasemide | 56211-40-6; 72810-59-4 | |
| Hydroxytorasemide | 99300-68-2; 99300-67-1 | Metabolites |
| Carboxytorasemide | | Metabolite |
| Tolbutamide | 64-77-7 | 0.55 |
| Bromocriptine and related compounds | | |
| Bromocriptine | 25614-03-3; 22260-51-1 | |
| Ifenprodil and related compounds | | |
| Ifenprodil | 23210-56-2; 23210-58-4 | |

The above molecules may be used alone or, preferably, in combination therapies to provide the most efficient clinical benefit. In this regard, in a preferred embodiment, the invention relates to a composition for use in the treatment of a neurological disorder, preferably AD, AD related disorders, MS, PD, ALS, HD, neuropathies (for instance neuropathic pain or alcoholic neuropathy), alcoholism or alcohol withdrawal, or spinal cord injury, comprising any one of the above compounds in combination with at least one distinct compound selected from Sulfisoxazole, Methimazole, Prilocaine, Dyphylline, Quinacrine, Carbenoxolone, Acamprosate, Aminocaproic acid, Baclofen, Cabergoline, Diethylcarbamazine, Cinacalcet, Cinnarizine, Eplerenone, Fenoldopam, Leflunomide, Levosimendan, Sulodexide, Terbinafine, Zonisamide, Etomidate, Phenformin, Trimetazidine, Mexiletine, Ifenprodil, Moxifloxacin, Bromocriptine or Torasemide, or a salt, prodrug, derivative, or sustained release formulation thereof.

The specific CAS number for each of these additional distinct compounds, different from those of Table 1 is provided in Table 2 below:

TABLE 2

| DRUG NAME | CAS NUMBER |
| --- | --- |
| Acamprosate | 77337-76-9; 77337-73-6; 107-35-7; 3687-18-1 |
| Aminocaproic Acid | 60-32-2 |
| Baclofen | 1134-47-0; 66514-99-6; 69308-37-8; 70206-22-3; 63701-56-4; 63701-55-3; 847353-30-4 |
| Cabergoline | 81409-90-7 |
| Carbenoxolone | 5697-56-3 or 7421-40-1 |
| Cinnarizine | 298-57-7 |
| Diethylcarbamazine | 90-89-1 or 1642-54-2 |
| Dyphylline | 479-18-5 |
| Eplerenone | 107724-20-9 |
| Etomidate | 33125-97-2 |
| Fenoldopam | 67227-57-0 or 67227-56-9 |
| Leflunomide | 75706-12-6 |
| Levosimendan | 141505-33-1 |
| Methimazole | 60-56-0 |
| Moxifloxacin | 151096-09-2 or 186826-86-8 or 192927-63-2 or 354812-41-2 |
| Phenformin | 114-86-3 or 834-28-6 |
| Prilocaine | 721-50-6 or 14289-31-7 or 14289-32-8 |
| Quinacrine | 83-89-6 or 69-05-6 or 6151-30-0 |
| Sulodexide | 57821-29-1 |
| Terbinafine | 91161-71-6 |
| Trimetazidine | 5011-34-7 or 13171-25-0 |
| Zonisamide | 68291-97-4 |

Specific examples of prodrugs of Baclofen are given in Hanafi et al, 2011 (41), particularly Baclofen esters and Baclofen ester carbamates which are of particular interest for CNS targeting. Hence such prodrugs are particularly suitable for compositions of this invention. Arbaclofen placarbil as mentioned before is also a well-known prodrug and may thus be used instead of Baclofen in compositions of the invention. Other prodrugs of Baclofen can be found in the following patent applications: WO2010102071, US2009197958, WO2009096985, WO2009061934, WO2008086492, US2009216037, WO2005066122, US2011021571, WO2003077902, and WO2010120370.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO2009033069, WO2009033061, WO2009033054 WO2009052191, WO2009033079, US 2009/0099253, US 2009/0069419, US 2009/0082464, US 2009/0082440, and US 2009/0076147.

In a preferred embodiment, the invention relates to a composition comprising:
at least one first compound selected from Torasemide, Trimetazidine, Mexiletine, Ifenprodil, Bromocriptine and Moxifloxacin salt(s), prodrug(s), derivative(s) of any chemical purity, or sustained release formulation(s) thereof, in combination with
at least one second compound, distinct from said first compound, selected from Sulfisoxazole, Methimazole, Prilocaine, Dyphylline, Quinacrine, Carbenoxolone, Acamprosate, Aminocaproic acid, Baclofen, Cabergoline, Diethylcarbamazine, Cinacalcet, Cinnarizine, Eplerenone, Fenoldopam, Leflunomide, Levosimendan, Sulodexide, Terbinafine, Zonisamide, Etomidate, Phenformin, Trimetazidine, Mexiletine, Bromocriptine, Ifenprodil, Torasemide and Moxifloxacin, salt(s), prodrug(s), derivative(s) of any chemical purity, or sustained release formulation(s) thereof, for use in the treatment of a neurological disorder in a subject in need thereof.

In a particular embodiment, the invention relates to the use of these drugs or compositions for treating AD or a related disorder in a subject in need thereof.

In a particular embodiment, the invention relates to the use of these drugs or compositions for treating MS, PD, ALS, HD, neuropathies (for instance neuropathic pain or alcoholic neuropathy), alcoholism or alcohol withdrawal, or spinal cord injury, in a subject in need thereof.

As disclosed in the examples, composition therapies using one or more of the above-listed drugs lead to an efficient correction of Alzheimer's disease and other neurological diseases. As illustrated in the experimental section, compositions comprising at least Torasemide, Trimetazidine, Mexiletine, Ifenprodil, Bromocriptine, and Moxifloxacin provide substantial therapeutic and biological effect to prevent the toxic effects of amyloid β(Aβ) protein or peptide on human cells. Moreover, in vivo, these compositions lead to an improvement of cognitive symptoms as well as to an inhibition of molecular pathways triggered by Aβ intoxication, within which glutamate excitotoxicity. Hence they represent novel and potent methods for treating such disease.

The experimental section further shows that the above mentioned compositions are also efficient i) in synergistically protecting in vitro neuronal cells from glutamate toxicity, and ii) in conferring clinical benefit in in vivo models for diseases related to glutamate excitotoxicity.

More preferably, drug compositions of the invention may comprise 1, 2, 3, 4 or 5 distinct drugs, even more preferably 2, 3 or 4 distinct drugs for combinatorial treatment of Alzheimer's disease (AD), AD related disorders, MS, PD, ALS, HD, neuropathies (for instance neuropathic pain or alcoholic neuropathy), alcoholism or alcohol withdrawal, or spinal cord injury in a subject in need thereof. In a preferred embodiment, the drugs of the invention are used in combination(s) for combined, separate or sequential administration, in order to provide the most effective effect.

In a particular embodiment, the composition comprises (i) Torasemide and (ii) a compound selected from Bromocriptine, Baclofen, Sulfisoxazole, Eplerenone or Terbinafine, or a salt, prodrug, derivative, or sustained release formulation of said compounds (i) and (ii).

In another particular embodiment, the composition comprises (i) Trimetazidine and (ii) a compound selected from Baclofen, Cinnarizine, Zonisamide, or Moxifloxacin, or a salt, prodrug, derivative, or sustained release formulation of said compounds (i) and (ii).

According to a further particular embodiment, the composition comprises (i) Moxifloxacin and (ii) a compound selected from Baclofen, Cinacalcet, Zonisamide, Sulfisoxazole, or Trimetazidine, or a salt, prodrug, derivative, or sustained release formulation of said compounds (i) and (ii).

In another further particular embodiment, the composition comprises (i) Mexiletine and (ii) a compound selected from Baclofen, Cinacalcet, Ifenprodil, or levosimendan or a salt, prodrug, derivative, or sustained release formulation of said compounds (i) and (ii).

A particular embodiment also relates to a composition comprising (i) Ifenprodil and (ii) a compound selected from Acamprosate, Levosimendan, or Mexiletine or a salt, prodrug, derivative, or sustained release formulation of said compounds (i) and (ii).

Preferred compositions of the invention, for use in the treatment of a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury, comprise one of the following drug combinations, for combined, separate or sequential administration:

Baclofen and Torasemide,
Eplerenone and Torasemide,
Acamprosate and Ifenprodil,
Baclofen and Mexiletine,
Baclofen and Trimetazidine,
Bromocriptine and Sulfisoxazole,
Cinacalcet and Mexiletine,
Cinnarizine and Trimetazidine,
Sulfisoxazole and Torasemide,
Trimetazidine and Zonisamide,
Levosimendan and Mexiletine,
Levosimendan and Ifenprodil,
Levosimendan and Trimetazidine,
Levosimendan and Moxifloxacin,
Terbinafine and Torasemide,
Moxifloxacin and Trimetazidine,
Moxifloxacin and Baclofen,
Moxifloxacin and Cinacalcet,
Moxifloxacin and Zonisamide,
Moxifloxacin and Sulfisoxazole, or
Mexiletine and Ifenprodil.

Examples of preferred compositions according to the invention comprising a combination of at least three compounds, for combined, separate or sequential administration, are provided below:

Baclofen and Trimetazidine and Torasemide,
Baclofen and Cinacalcet and Torasemide,
Baclofen and Acamprosate and Torasemide,
Levosimendan and Baclofen and Trimetazidine,
Levosimendan and Aminocaproic acid and Trimetazidine,
Levosimendan and Terbinafine and Trimetazidine, or
Levosimendan and Sulfisoxazole and Trimetazidine.

Examples of preferred compositions according to the invention comprising a combination of at least four compounds, for combined, separate or sequential administration, are provided below:

Sulfisoxazole and Trimetazidine and Torasemide and Zonisamide,
Sulfisoxazole and Mexiletine and Torasemide and Cinacalcet,
Baclofen and Acamprosate and Torasemide and Diethylcarbamazine, or
Baclofen and Acamprosate and Torasemide and Ifenprodil.

As disclosed in the experimental section the above combination therapies of the invention induce a strong neuroprotective effect against Aβ toxicity and give positive results in behavioural performances and biochemical assays in vivo. The results show that compositions of the invention i) efficiently correct molecular pathways triggered, in vivo, by Aβ aggregates and ii) lead to an improvement of neurophysiological impairments observed in diseased animals as neuron survival or synapse integrity.

Moreover, the results presented show also that the above combinations therapies have an important synergistic neuroprotecting effect against glutamate excitotoxicity (FIGS. 24 and 25, table 8), a pathway which is implicated in various neurological diseases as AD, MS, PD, ALS, HD, neuropathies (for instance neuropathic pain or alcoholic neuropathy), alcoholism or alcohol withdrawal, or spinal cord injury. These therapies give positive results in in vivo or in vitro models for these diseases.

In addition, in vivo results also show that compositions of the invention efficiently restore Brain Blood Barrier integrity, which is known to be impaired in several neurological diseases.

An object of this invention thus also resides in a composition as defined above for treating a neurological disorder such as Alzheimer's disease (AD), AD related disorders, MS, PD, ALS, HD, neuropathies (for instance alcoholic neuropathy or neuropathic pain), alcoholism or alcohol withdrawal, or spinal cord injury.

A further object of this invention resides in the use of a composition as defined above for the manufacture of a medicament for treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury.

The invention further provides a method for treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury, comprising administering to a subject in need thereof an effective amount of a composition as disclosed above.

As indicated previously, the compounds in a combinatorial treatment or composition of the present invention may be formulated together or separately, and administered together, separately or sequentially and/or repeatedly.

In this regard, a particular object of this invention is a method for treating AD, an AD related disorder, MS, PD, ALS, HD, neuropathies (for instance neuropathic pain or alcoholic neuropathy), alcoholism or alcohol withdrawal, or spinal cord injury in a subject, comprising administering simultaneously, separately or sequentially to a subject in need of such a treatment, an effective amount of a composition as disclosed above.

In a preferred embodiment, the invention relates to a method of treating Alzheimer's disease (AD), an AD related disorder, MS, PD, ALS, HD, neuropathies (for instance neuropathic pain or alcoholic neuropathy), alcoholism or alcohol withdrawal, or spinal cord injury in a subject in need thereof, comprising administering to the subject an effective amount of Torasemide, Trimetazidine, Mexiletine, Ifenprodil, Bromocriptine or Moxifloxacin, or salt(s) or prodrug(s) or derivative(s) or sustained release formulation(s) thereof, preferably in a combination as disclosed above.

In another embodiment, this invention relates to a method of treating Alzheimer's disease (AD), an AD related disorder, MS, PD, ALS, HD, neuropathies (for instance neuropathic pain or alcoholic neuropathy), alcoholism or alcohol withdrawal, or spinal cord injury in a subject in need thereof, comprising simultaneously, separately or sequentially administering to the subject at least one first compound selected from the group consisting of Torasemide, Trimetazidine, Mexiletine, Ifenprodil, Bromocriptine and Moxifloxacin salts, prodrugs, derivatives, or any formulation thereof, in combination with at least one second compound distinct from said first compound, selected from, Sulfisoxazole, Methimazole, Prilocaine, Dyphylline, Quinacrine, Carbenoxolone, Acamprosate, Aminocaproic acid, Baclofen, Cabergoline, Diethylcarbamazine, Cinacalcet, Cinnarizine, Eplerenone, Fenoldopam, Leflunomide, Levosimendan, Sulodexide, Terbinafine, Zonisamide, Etomidate, Phenformin, Trimetazidine, Mexiletine, Bromocriptine, Ifenprodil, Torasemide, and Moxifloxacin salts, prodrugs, derivatives, or any formulation thereof.

In a further embodiment, the invention relates to a method of treating Alzheimer's disease (AD), an AD related disorder, MS, PD, ALS, HD, neuropathies (for instance neuropathic pain or alcoholic neuropathy), alcoholism or alcohol withdrawal, or spinal cord injury comprising administering to a subject in need thereof, at least one first compound selected from the group consisting of Torasemide, Trimetazidine, Mexiletine, Ifenprodil, Bromocriptine and Moxifloxacin salts, prodrugs, derivatives, or any formulation thereof, in combination with at least one second compound distinct from said first compound, selected from, Sulfisoxazole, Methimazole, Prilocaine, Dyphylline, Quinacrine, Carbenoxolone, Acamprosate, Aminocaproic acid, Baclofen, Cabergoline, Diethylcarbamazine, Cinacalcet, Cinnarizine, Eplerenone, Fenoldopam, Leflunomide, Levosimendan, Sulodexide, Terbinafine, Zonisamide, Etomidate, Phenformin, Trimetazidine, Mexiletine, Bromocriptine, Ifenprodil, Torasemide, and Moxifloxacin salts, prodrugs, derivatives, or any formulation thereof.

As disclosed in the examples, besides being efficient in protecting neurons from glutamate toxicity, baclofen-torasemide therapy is also particularly efficient in promoting neuronal cell growth, even in the absence of any exposure to a toxic agent or condition. Moreover, in vivo, this combination therapy leads to an improvement of loss of transduction of nervous signal subsequent to nerve injury. Hence baclofen-torasemide combination represents a novel and potent therapy for treating neuropathies, nerve injuries, and spinal cord injury as defined above.

In this regard, in a particular embodiment, the invention relates to a method for treating neuropathies, e.g., peripheral nerves injuries or spinal cord injuries, comprising administering to a subject in need thereof a composition comprising baclofen and torasemide salts, prodrugs, derivatives, or any formulation thereof.

In another particular embodiment, the invention relates to a method for treating neuropathies, e.g., inherited neuropathies as CMT diseases, comprising administering to a subject in need thereof a composition comprising baclofen and torasemide, or salts, prodrugs, derivatives, or any formulation thereof.

In a more particular embodiment, the invention relates to a method for treating CMT1 or CMT2 disease, comprising administering to a subject in need thereof a composition comprising baclofen and torasemide, or salts, prodrugs, derivatives, or any formulation thereof.

A particular object of this invention is also a method for treating neuropathies, e.g., peripheral nerves injuries or spinal cord injuries, comprising administering simultaneously, separately or sequentially and/or repeatedly to a subject in need of such a treatment, an effective amount of a baclofen and torasemide as disclosed above.

Although very effective in vitro and in vivo, depending on the subject or specific condition, the methods and compositions of the invention may be used in further conjunction with additional drugs or treatments beneficial to the treated neurological condition in the subjects. In this regard, in a particular embodiment, the drug(s) or compositions according to the present invention may be further combined with *Ginkgo biloba* extracts. Suitable extracts include, without limitation, *Ginkgo biloba* extracts, improved *Ginkgo biloba* extracts (for example enriched in active ingredients or lessened in contaminant) or any drug containing *Ginkgo biloba* extracts.

*Ginkgo biloba* extracts may be used in a composition comprising at least Torasemide, Trimetazidine, Mexiletine, Bromocriptine, Ifenprodil and Moxifloxacin.

In preferred embodiments, *Ginkgo Biloba* extracts are used in combination with anyone of the following drug combinations:

Acamprosate and Ifenprodil,
Baclofen and Mexiletine,
Baclofen and Torasemide,
Baclofen and Trimetazidine,
Bromocriptine and Sulfisoxazole,
Cinacalcet and Mexiletine,
Cinnarizine and Trimetazidine,
Eplerenone and Torasemide,
Sulfisoxazole and Torasemide,
Trimetazidine and Zonisamide,
Levosimendan and Mexiletine,
Levosimendan and Ifenprodil,
Levosimendan and Trimetazidine,
Levosimendan and Moxifloxacin,
Terbinafine and Torasemide,
Moxifloxacin and Baclofen,
Moxifloxacin and Cinacalcet,
Moxifloxacin and Zonisamide,
Moxifloxacin and Sulfisoxazole,
Mexiletine and Ifenprodil,
Baclofen and Trimetazidine and Torasemide,
Baclofen and Cinacalcet and Torasemide,
Baclofen and Acamprosate and Torasemide,
Sulfisoxazole and Trimetazidine and Torasemide and Zonisamide,
Sulfisoxazole and Mexiletine and Torasemide and Cinacalcet,
Baclofen and Acamprosate and Torasemide and Diethylcarbamazine,
Baclofen and Acamprosate and Torasemide and Ifenprodil,
Levosimendan and Baclofen and Trimetazidine,
Levosimendan and Aminocaproic acid and Trimetazidine,
Levosimendan and Terbinafine and Trimetazidine, or
Levosimendan and Sulfisoxazole and Trimetazidine.

Other therapies used in conjunction with drug(s) or drug(s) combination(s) according to the present invention, may comprise one or more drug(s) that ameliorate symptoms of Alzheimer's disease, an AD related disorder, MS, PD, ALS, HD, neuropathies (for instance neuropathic pain or alcoholic neuropathy), alcoholism or alcohol withdrawal, or spinal cord injury, or drug(s) that could be used for palliative treatment of these disorders.

For instance, combinations of the invention can be used in conjunction with Donepezil (CAS: 120014-06-4), Gabapentine (CAS: 478296-72-9; 60112-96-3), Galantamine (357-70-0), Rivastigmine (123441-03-2) or Memantine (CAS: 19982-08-2).

A further object of this invention relates to the use of a compound or combination of compounds as disclosed above for the manufacture of a medicament for the treatment of the above listed disorders, by combined, separate or sequential administration to a subject in need thereof.

A further object of this invention is a method of preparing a pharmaceutical composition, the method comprising mixing the above compounds in an appropriate excipient or carrier.

The duration of the therapy depends on the stage of the disease or disorder being treated, the combination used, the age and condition of the patient, and how the patient responds to the treatment. The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recover from any as yet unforeseen side-effects. The drugs may also be formulated together such that one administration delivers all drugs.

The administration of each drug of the combination may be by any suitable means that results in a concentration of the drug that, combined with the other component, is able to ameliorate the patient condition or efficiently treat the disease or disorder.

While it is possible for the active ingredients of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained, in any appropriate amount, in any suitable carrier substance (e.g., excipient, vehicle, support), which may represent 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over au extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methyl call lose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Several drugs may be mixed together in the tablet, or may be partitioned. For example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl olylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation or such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n ropyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polyglactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type), and rectal gelatin capsules (solutions or suspensions). In a typical suppository formulation, the active drug(s) are combined with an appropriate pharmaceutically, acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and Liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

Administration is generally repeated. It can be one to several times daily for several days to several years, and may even be for the life of the patient. Chronic or at least periodically repeated long-term administration is indicated in most cases.

Additionally, pharmacogenomic (the effect of genotype on the pharmacokinetic, pharmacodynamic or efficacy profile of a therapeutic) information about a particular patient may affect the dosage used.

Except when responding to especially impairing cases when higher dosages may be required, the preferred dosage of each drug in the combination usually lies within the range of doses not above those usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually no substantial effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ⅒ of therapeutic doses. In particular examples, doses as low as 1/20, 1/30, 1/50, 1/100, or even lower, of therapeutic doses are used.

At such sub-optimal dosages, the compounds alone would be substantially inactive, while the combination(s) according to the invention are fully effective.

A preferred dosage corresponds to amounts from 1%, up to 50% of those usually prescribed for long-term maintenance treatment.

The most preferred dosage may correspond to amounts from 1% up to 10% of those usually prescribed for long-term maintenance treatment.

Specific examples of dosages of drugs for use in the invention are provided below:

Bromocriptine orally from about 0.01 to 10 mg per day, preferably less than 5 mg per day, more preferably less than 2.5 mg per day, even more preferably less than 1 mg per day, such dosages being particularly suitable for oral administration, Ifenprodil orally from about 0.4 to 6 mg per day, preferably less than 3 mg per 2.5 day, more preferably less than 1.5 mg per day, even more preferably less than 0.75 mg per day, such dosages being particularly suitable for oral administration, Mexiletine orally from about 6 to 120 mg per day, preferably less than 60 mg per day, more preferably less than 30 mg per day, even more preferably less than 15 mg per day, such dosages being particularly suitable for oral administration, Moxifloxacin orally from about 4 to 40 mg per day, preferably less than 20 mg per day, more preferably less than 10 mg per day, even more preferably less than 5 mg per day, such dosages being particularly suitable for oral administration, Torasemide orally from about 0.05 to 4 mg per day, preferably less than 2 mg per day, more preferably less than 1 mg per day, even more preferably less than 0.5 mg per day, such dosages being particularly suitable for oral administration, Trimetazidine orally from about 0.4 to (5 mg per day, preferably less than 3 mg per day, more preferably less than 1.5 mg per day, even more preferably less than 0.75 mg per day, such dosages being particularly suitable for oral administration, Acamprosate orally from about 1 to 400 mg per day, Aminocaproic Acid orally from about 0.1 g to 2.4 g per day, Baclofen orally from about 0.15 to 15 mg per day, Diethylcarbamazine orally from about 0.6 to 600 mg per day, Cinacalcet orally from about 0.3 to 36 mg per day, Cinnarizine orally from about 0.6 to 23 mg per day, Eplerenone orally from about 0.25 to 10 mg per day, Leflunomide orally from about 0.1 to 10 mg per day, Levosimendan orally from about 0.04 to 0.8 mg per day, Sulfisoxazole orally from about 20 to 800 mg per day, Sulodexide orally from about 0.05 to 40 mg per day, Terbinafine orally from about 2.5 to 25 mg per day, Zonisamide orally from about 0.5 to 50 mg per day.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

The Care and Husbandry of Animals as Well as the Experimentations are Performed According to the Guidelines of the Committee Far Research and Ethical Issue of the I.A.S.P. (1983).

A) Treatment of Diseases Related to Aβ Toxicity

In this series of experiments, candidate compounds have been tested for their ability to prevent or reduce the toxic effects of human $A\beta_{1\text{-}42}$. $A\beta_{1\text{-}42}$ is the fill length peptide that constitutes aggregates found in biopsies from human patients afflicted with AD, The drugs are first tested individually, followed by assays of their combinatorial action. The effect is determined on various cell types, to further document the activity of the compounds in in vitro models which illustrate different physiological features of AD. In vivo studies are also performed in a mouse model for AD confirming this protective effect by evaluating the effect of the compounds on i) the cognitive performance of animals and ii) on molecular hallmarks (apoptosis induction, oxidative stress induction, inflammation pathway induction) of AD.

I. The Compounds Prevent Toxicity of Human $A\beta_{1\text{-}42}$

I.1. Protection Against the Toxicity of $A\beta_{1\text{-}42}$ in Human Brain Microvascular Endothelial Cell Model Human brain microvascular endothelial cell cultures were used to study the protection afforded by candidate compound(s) on $A\beta_{1\text{-}42}$ toxicity.

Human brain microvascular endothelial cerebral cells (HBMEC, ScienCell Ref: 1000, frozen at passage 10) were rapidly thawed in a waterbath at ±37° C. The supernatant was immediately put in 9 ml Dulbecco's modified Eagle's medium (DMEM; Pan Biotech ref: P04-03600) containing 10% of foetal calf serum (FCS; GIBCO ref 10270-106). Cell suspension was centrifuged at 180×g for 10 min. at +4° C. and the pellets were suspended in CSC serum-free medium (CSC serum free, Cell System, Ref: SF-4Z0-500-R, Batch 51407-4) with 1.6% of Serum free RocketFuel (Cell System, Ref: SF-4Z0-500-R, Batch 54102), 2% of Penicillin 10.000 U/ml and Streptomycin 10 mg/ml (PS; Pan Biotech ref P06-07100 batch 133080808) and were seeded at the density of 20000 cells per well in 96 well lates (matrigel layer biocoat angiogenesis system, BD, Ref 354150, Batch A8662) in a final volume of 100 µl. On matrigel support, endothelial cerebral cells spontaneously started the process of capillary network morphogenesis (33).

Three separate cultures were performed per condition, 6 wells per condition.

Candidate Compounds and Human Amyloid $\beta_{1\text{-}42}$ Treatment

Briefly, $A\beta_{1\text{-}42}$ peptide (Bachem, ref: H1368 batch 1010533) was reconstituted in define culture medium at 20 µM (mother solution) and was slowly shaken at +37° C. for 3 days in dark for aggregation. The control medium was prepared in the same conditions.

After 3 days, this aggregated human amyloid peptide was used on HBMEC at 2.5 µM diluted in control medium (optimal incubation time). The $A\beta_{1\text{-}42}$ peptide was added 2 hours after HBMEC seeding on matrigel for 18 hours incubation.

One hour after HBMEC seeding on matrigel, test compounds and VEGF-165 were solved in culture medium (+0.1% DMSO) and then pre-incubated with HBMEC for 1 hour before the $A\beta_{1\text{-}42}$ application (in a final volume per culture well of 1000). One hour after test compounds or VEGF incubation (two hours after cell seeding on matrigel), 100 µl of $A\beta_{1\text{-}42}$ peptide was added to a final concentration of 2.50 µM diluted in control medium in presence of test compounds or VEGF (in a 200 µl total volume/well), in order to avoid further drug dilutions.

Organization of Cultures Plates

VEGF-165 known to be a pro-angiogenic isoform of VEGF-A, was used for all experiment in this study as reference compound. VEGF-165 is one of the most abundant VEGF isoforms involved in angiogenesis. VEGF was used as reference test compound at 10 nM.

The following conditions were assessed:

Negative Control: medium alone+0.1% DMSO

Intoxication: amyloid-$\beta_{1\text{-}42}$ (2.5 µM) for 18 h

Positive control: VEGF-165 (10 nM) (1 reference compound/culture) 1 hr before the $A\beta_{1\text{-}42}$ (2.5 µM) addition for a 18 h incubation time.

Test compounds. Test compound 1 hr before the $A\beta_{1\text{-}42}$ (2.5 µM) addition for a 18 h incubation time.

Capillary Network Quantification

Per well, 2 pictures with 4× lens were taken using IInCell Analyzer™ 1000 (GE Healthcare) in light transmission. All images were taken in the same conditions. Analysis of the angiogenesis networks was done using Developer software (GE Healthcare). The total length of capillary network was assessed.

Data Processing

Figure 1B:
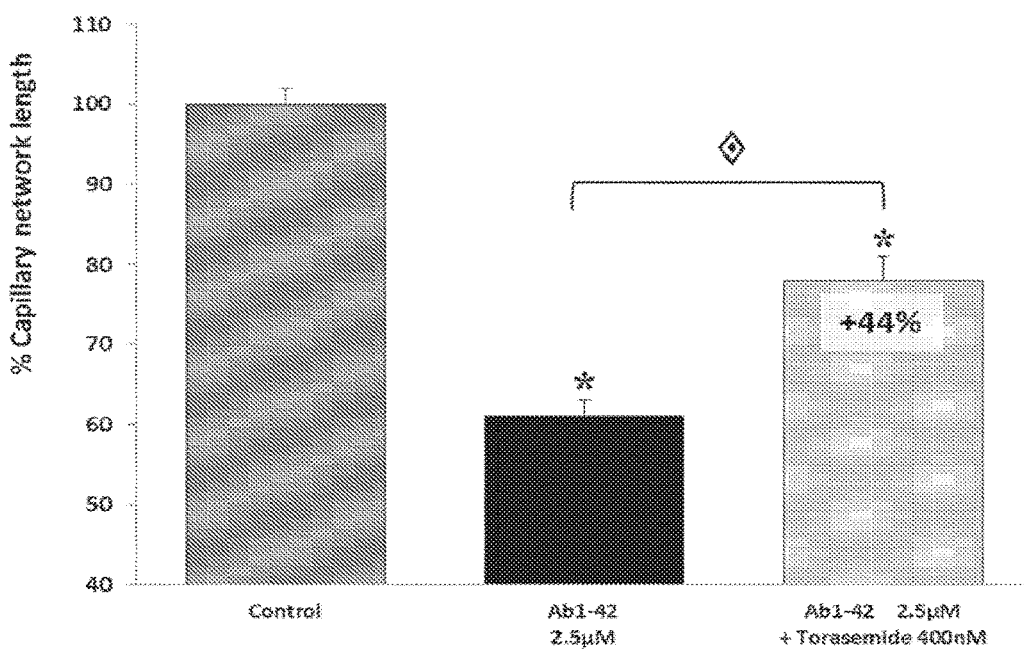
Figure 1C:
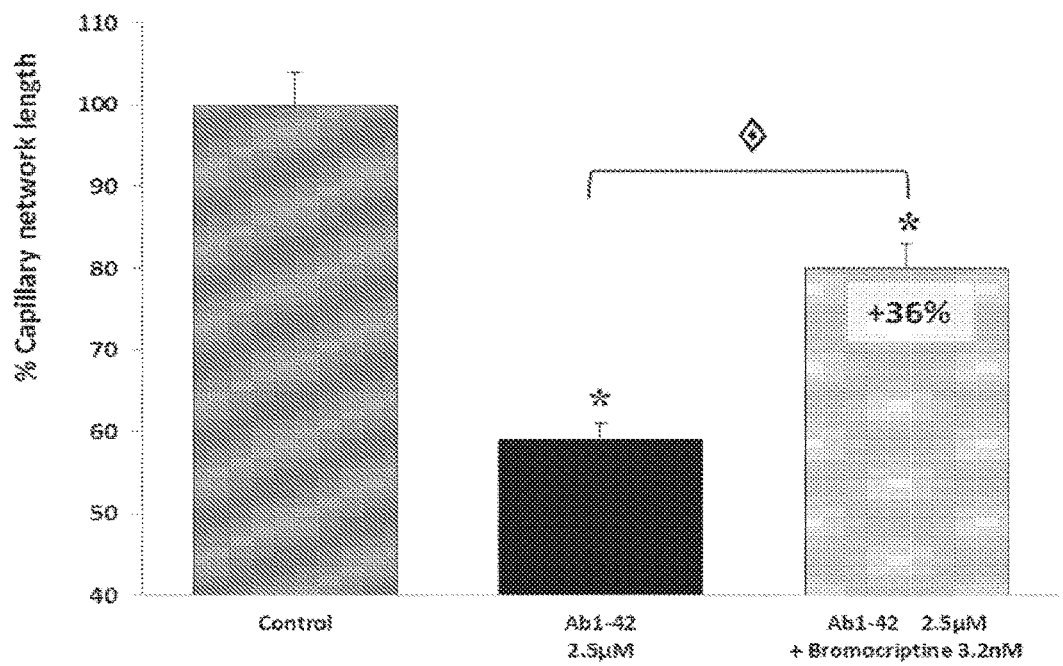
Figure 2A:
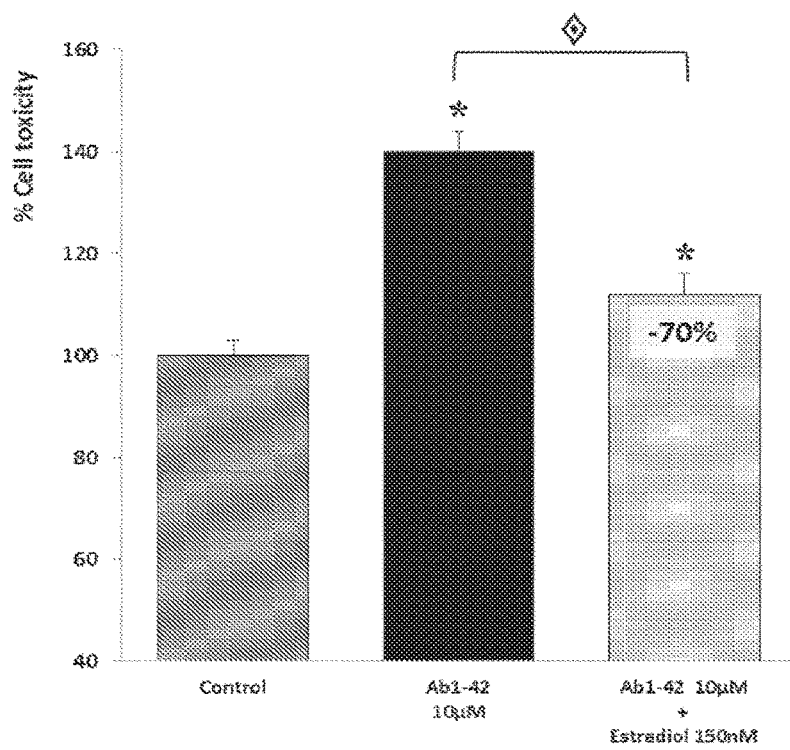
FIGS. 2A-2F: Effect of selected drugs pre-treatment on LDH release in human $A\beta_{1-42}$ toxicity assays on rat primary cortical cells. A) Validation of the experimental model used for drug screening: 1 hr of Estradiol (150 ng/ml) pre-treatment significantly protected the neurons from this amyloid injury (−70%), which is considered as a positive control for neuroprotection. For all experiments, $A\beta_{1-42}$ produces a significant intoxication compared to vehicle-treated neurons. The intoxication is significantly prevented by Bromocriptine (40 nM, −29%) (B), Trimetazidine (40 nM, −94%) (C), Ifenprodil (600 nM, −94%) (D), Mexiletine (3.2 nM, −73%) (E), Moxifloxacin (20 nM, −63%) (F). Note that for other drug concentrations, no or a weaker effect is noticed for upper and lower doses. ◊: $p<0.05$: significantly different from $A\beta_{1-42}$ intoxication.
Figure 2B:
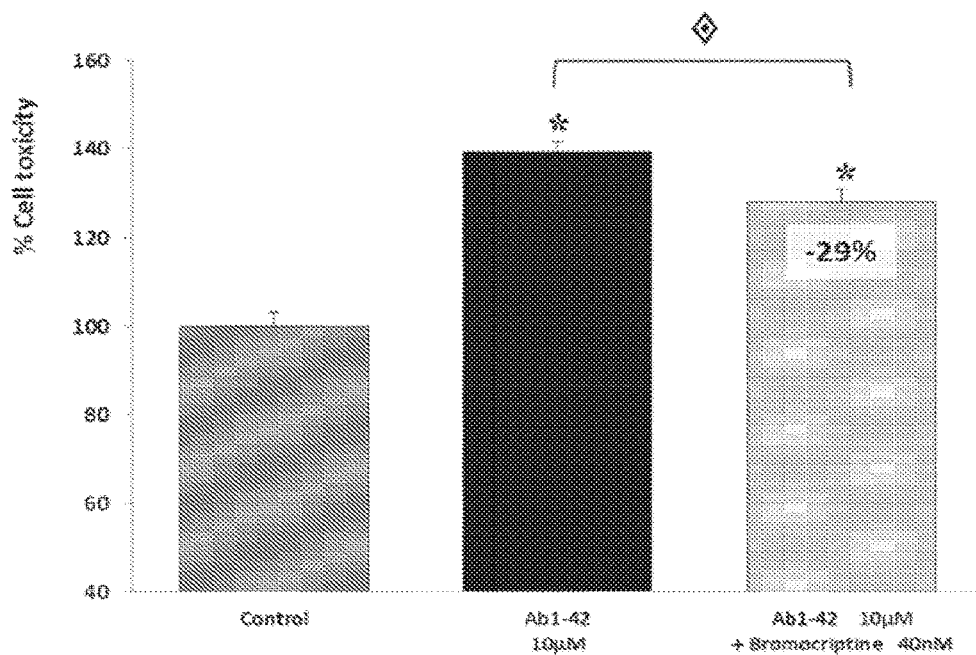
Figure 2C:
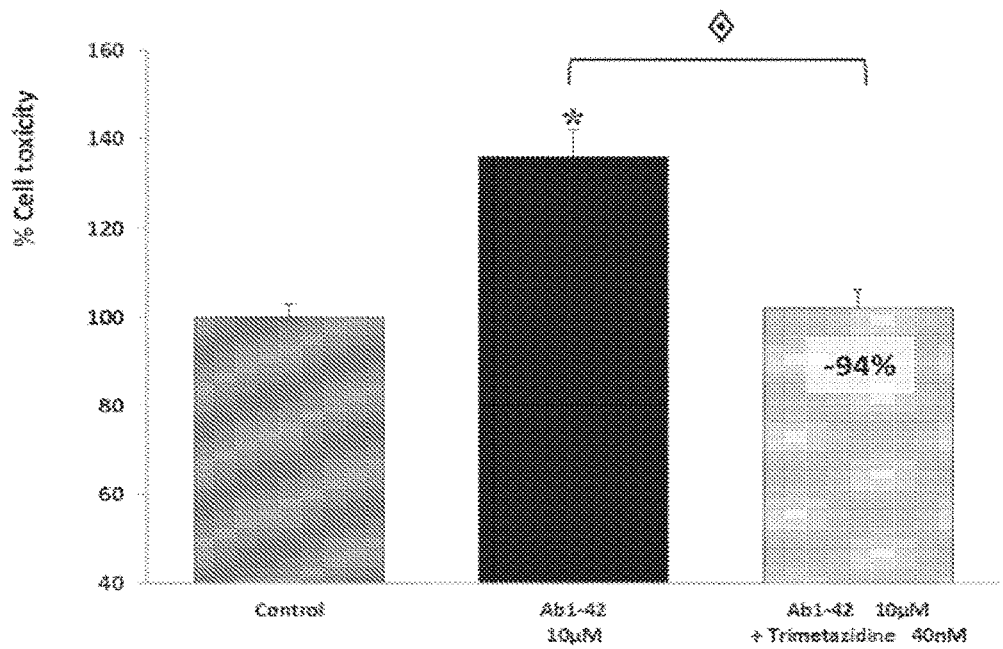
Figure 2D:
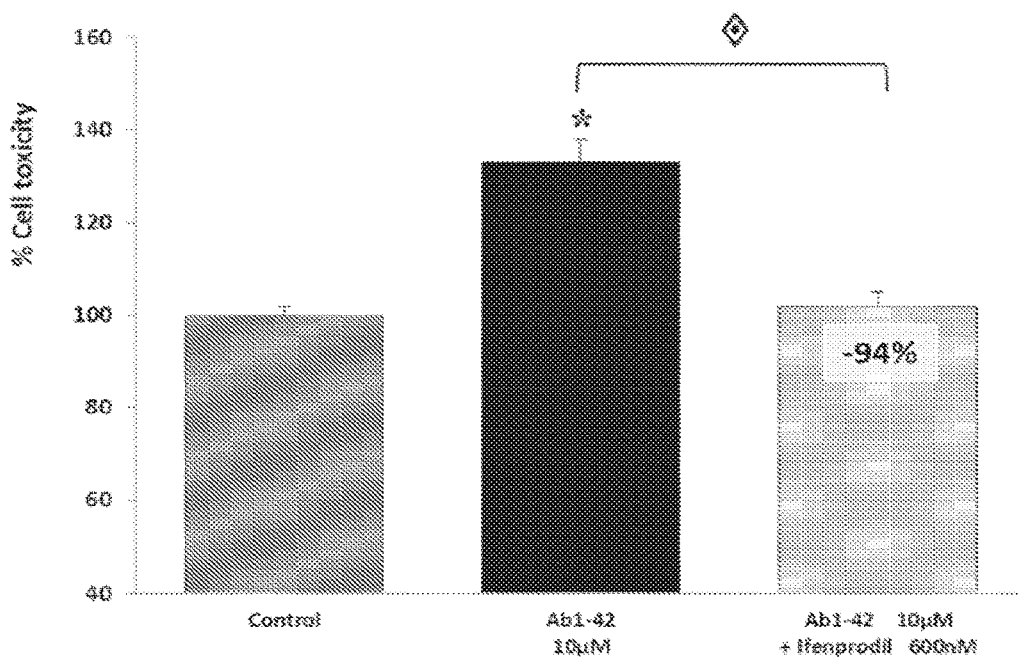
Figure 2E:
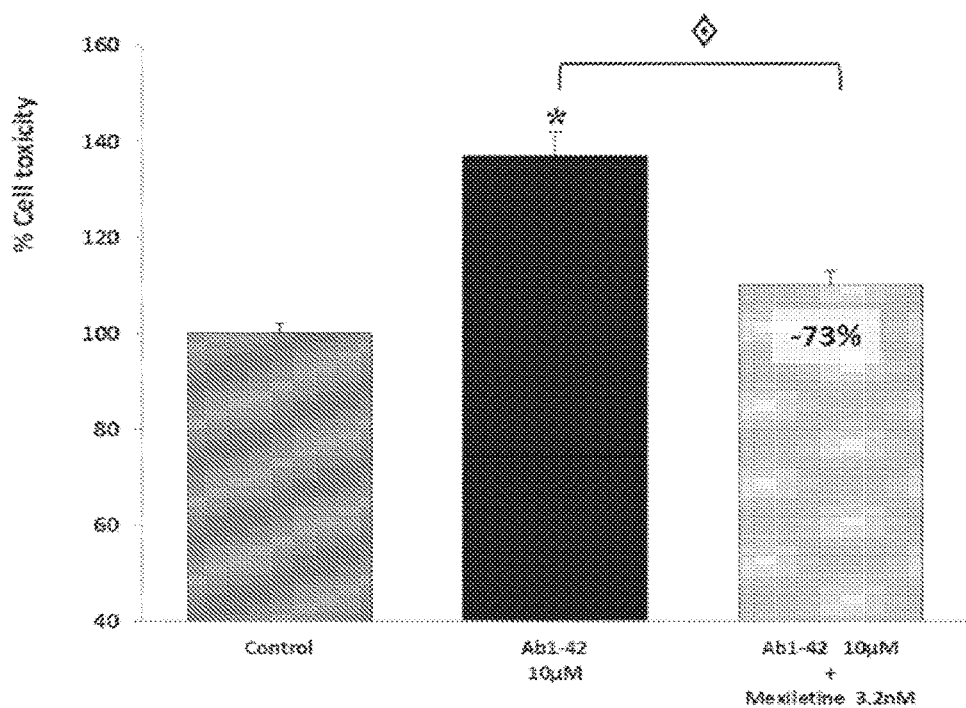
Figure 2F:
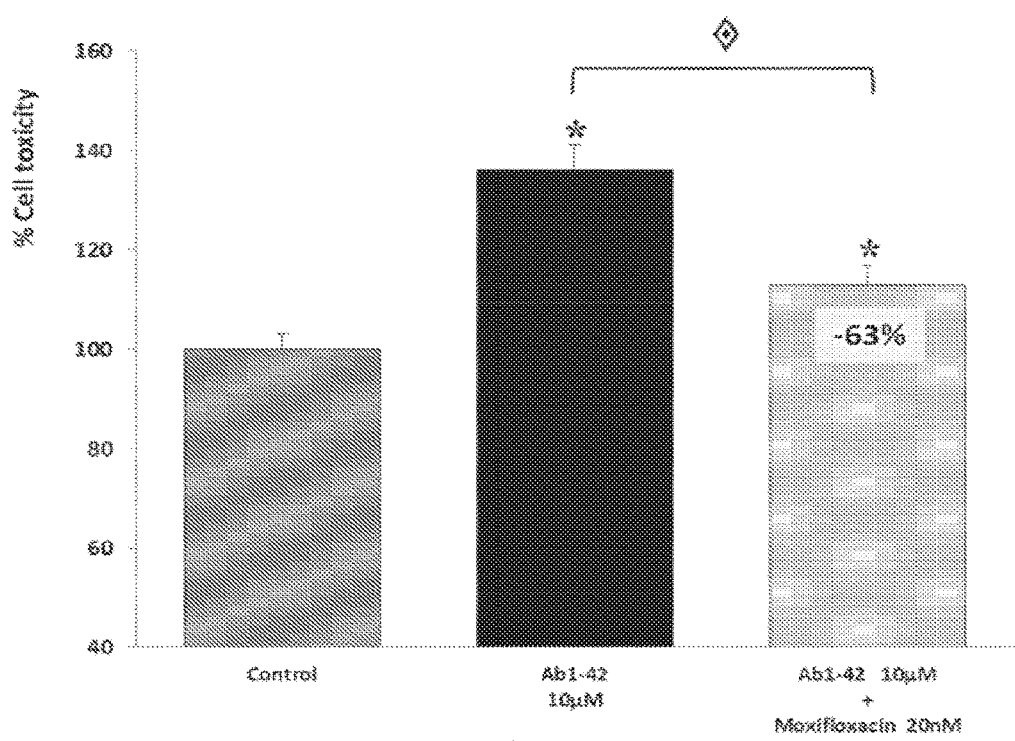
Figures 4A, 4B, 4C:
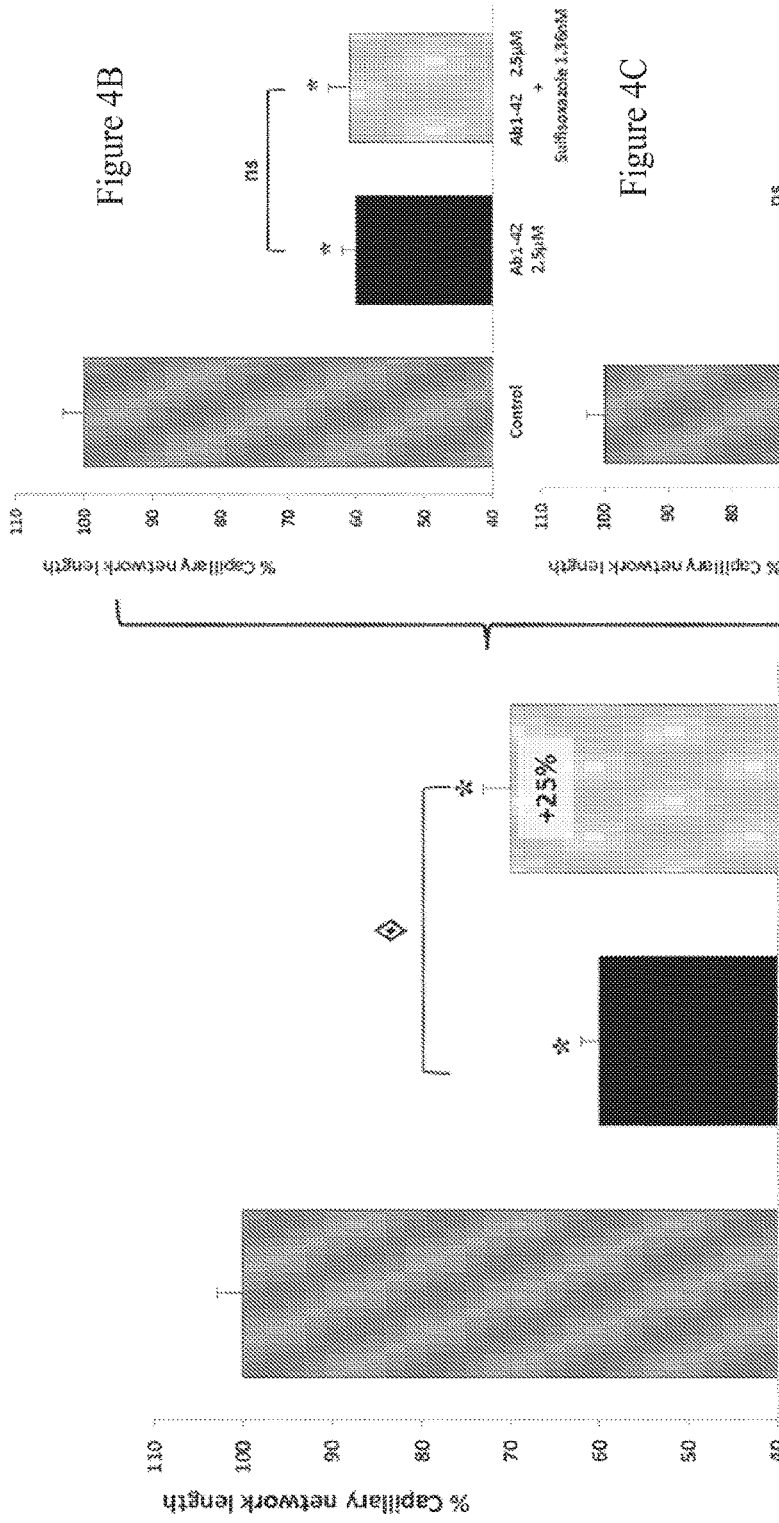
FIGS. 4A-4C: Effect of Sulfisoxazole and Torasemide combination therapy on the total length of capillary network in beta-amyloid intoxicated HBMEC cultures. The aggregated human amyloid peptide ($A\beta_{1-42}$ 2.5 μM) produces a significant intoxication, above 40%, compared to vehicle-treated cells. This intoxication is significantly prevented by the combination of Sulfisoxazole and Torasemide (A) whereas, at those concentrations, Sulfisoxazole (B) and Torasemide (C) alone have no significant effect on intoxication. ◆: $p<0.05$, significantly different from $A\beta_{1-42}$ intoxication.
Figure 5A:
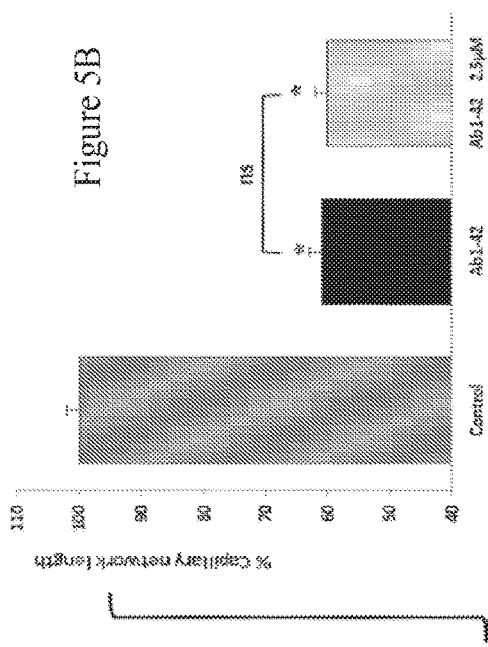
FIGS. 5A-5C: Effect of Eplerenone and Torasemide combination therapy on the total length of capillary network in beta-amyloid intoxicated HBMEC cultures. The aggregated human amyloid peptide ($A\beta_{1-42}$ 2.5 μM) produces a significant intoxication, above 40%, compared to vehicle-treated cells. This intoxication is significantly prevented by the combination of Eplerenone and Torasemide (A) whereas, at those concentrations, Torasemide (B) and Eplerenone (C) alone have no significant effect on intoxication. ◆: $p<0.05$, significantly different from $A\beta_{1-42}$ intoxication.
Figure 5B:
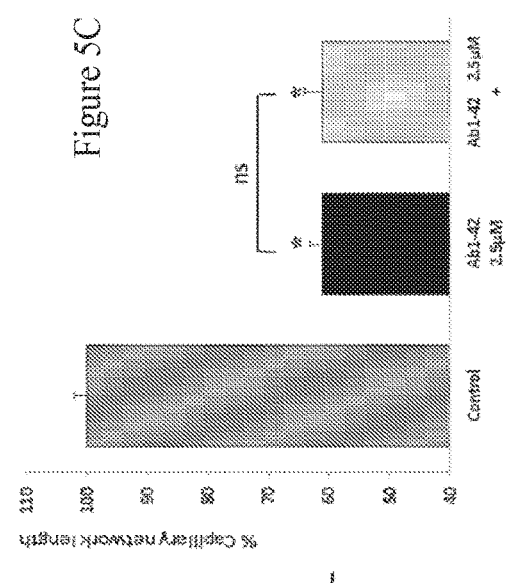
Figure 5C:
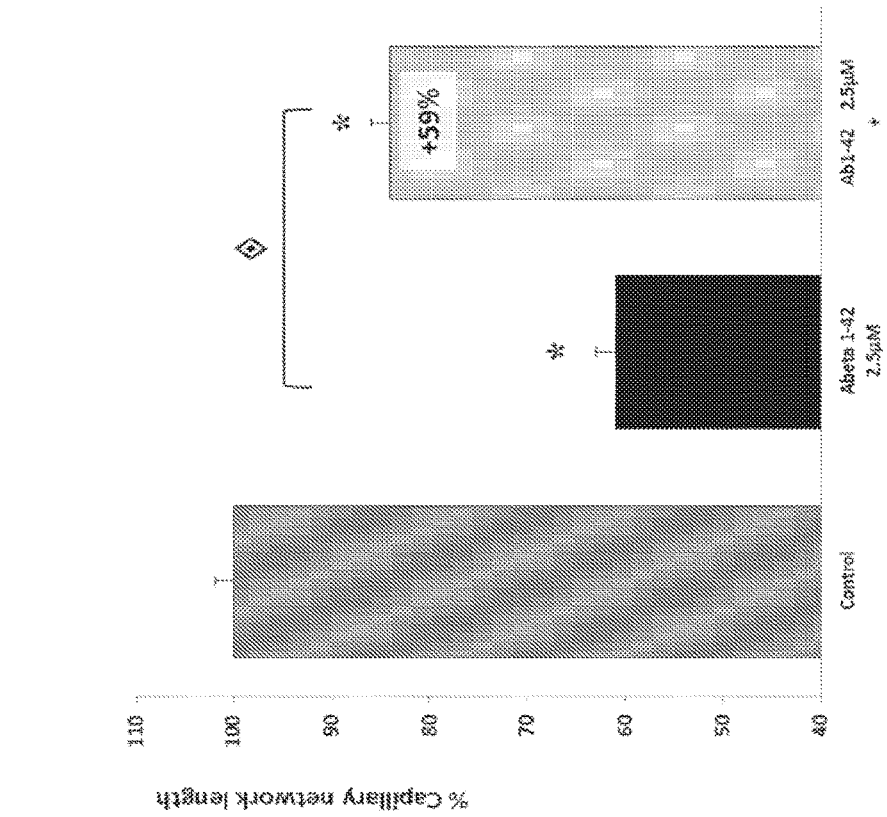
Figure 11B:
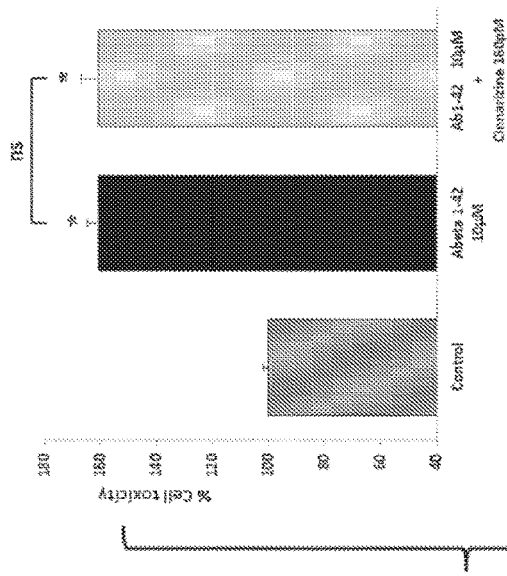
FIGS. 11A-11C: Effect of Cinnarizine and Trimetazidine combination therapy on LDH release in human $A\beta_{1-42}$ toxicity on rat primary cortical cells. The aggregated human amyloid peptide ($A\beta_{1-42}$ 10 μM) produces a significant intoxication compared to vehicle-treated neurons. This intoxication is significantly prevented by the combination of Cinnarizine and Trimetazidine (A) whereas, at those concentrations, Cinnarizine (B) and Trimetazidine (C) alone have no significant effect on intoxication. ◆: $p<0.05$, significantly different from $A\beta_{1-42}$ intoxication.
Figure 11C:
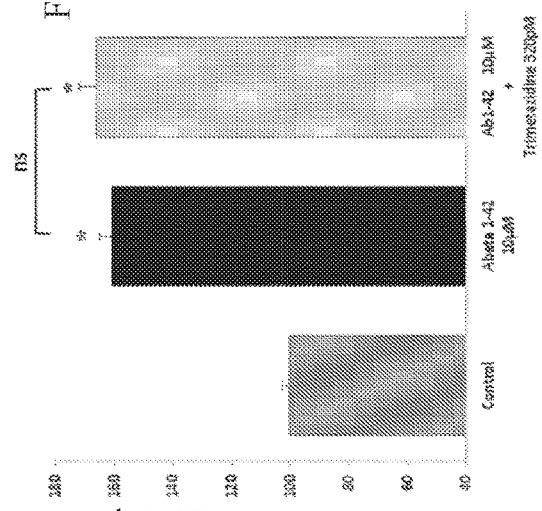
Figure 11A:
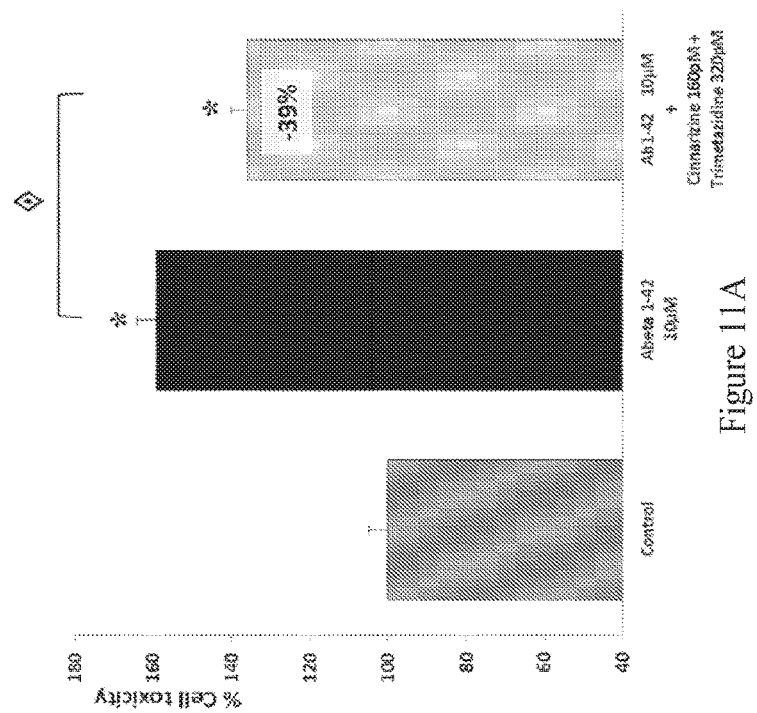
Figure 15:
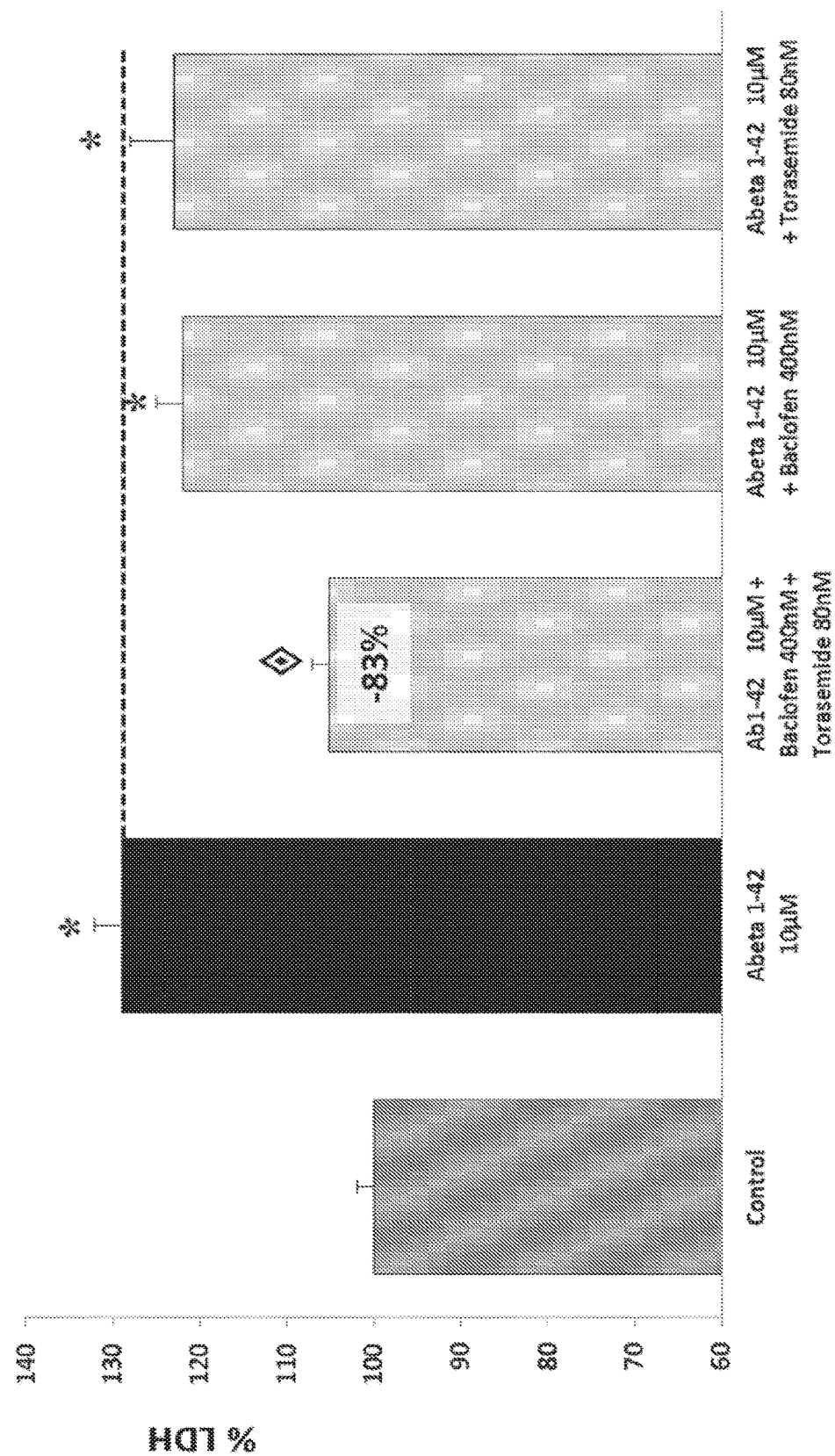
FIG. 15: Effect of Baclofen and Torasemide combination therapy on LDH release in human $A\beta_{1-42}$ toxicity on rat primary cortical cells. The aggregated human amyloid peptide ($A\beta_{1-42}$ 10 μM) produces a significant intoxication compared to vehicle-treated neurons. This intoxication is significantly prevented by the combination of Baclofen and Torasemide whereas, at those concentrations, Baclofen and Torasemide alone have no significant effect on intoxication. ◆: $p<0.05$, significantly different from $A\beta_{1-42}$ intoxication.
Figure 16A:
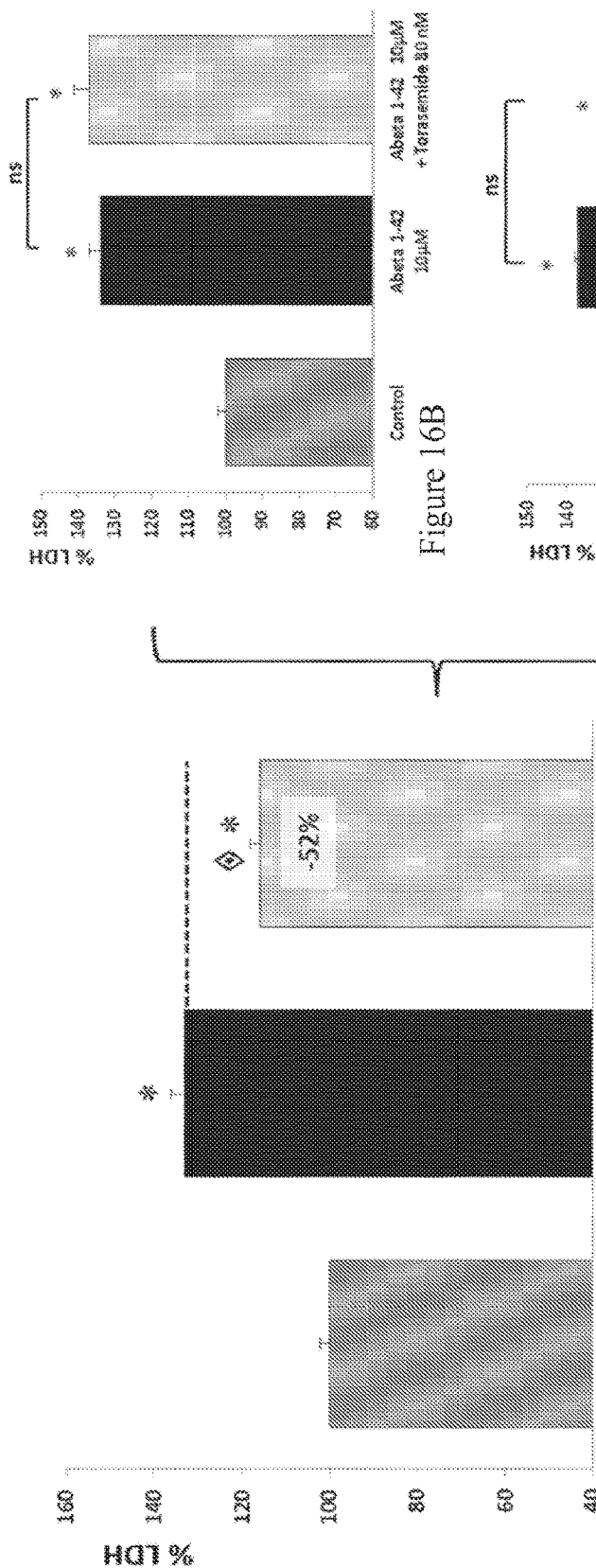
FIGS. 16A-16C: Effect of Torasemide and Sulfisoxazole combination therapy on LDH release in human $A\beta_{1-42}$ toxicity on rat primary cortical cells. The aggregated human amyloid peptide (A$\beta_{1-42}$ 10 µM) produces a significant intoxication compared to vehicle-treated neurons. This intoxication is significantly prevented by the combination of Sulfisoxazole and Torasemide (A) whereas, at those concentrations, Torasemide (B) and Sulfisoxazole (C) alone have no significant effect on intoxication. ◇: $p<0.05$, significantly different from A$\beta_{1-42}$ intoxication.
Figure 16B:
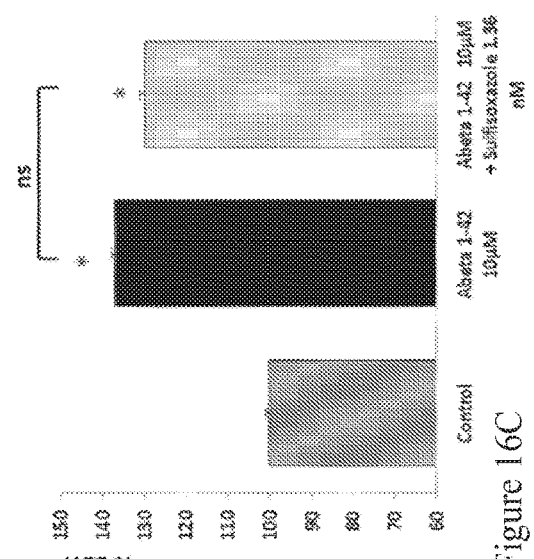
Figure 16C:
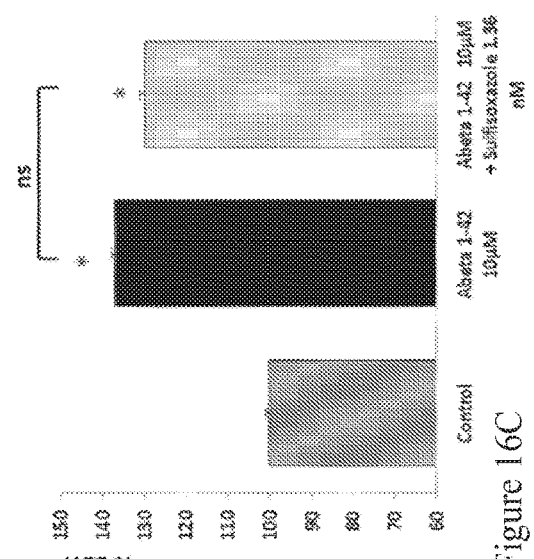
Figure 22:
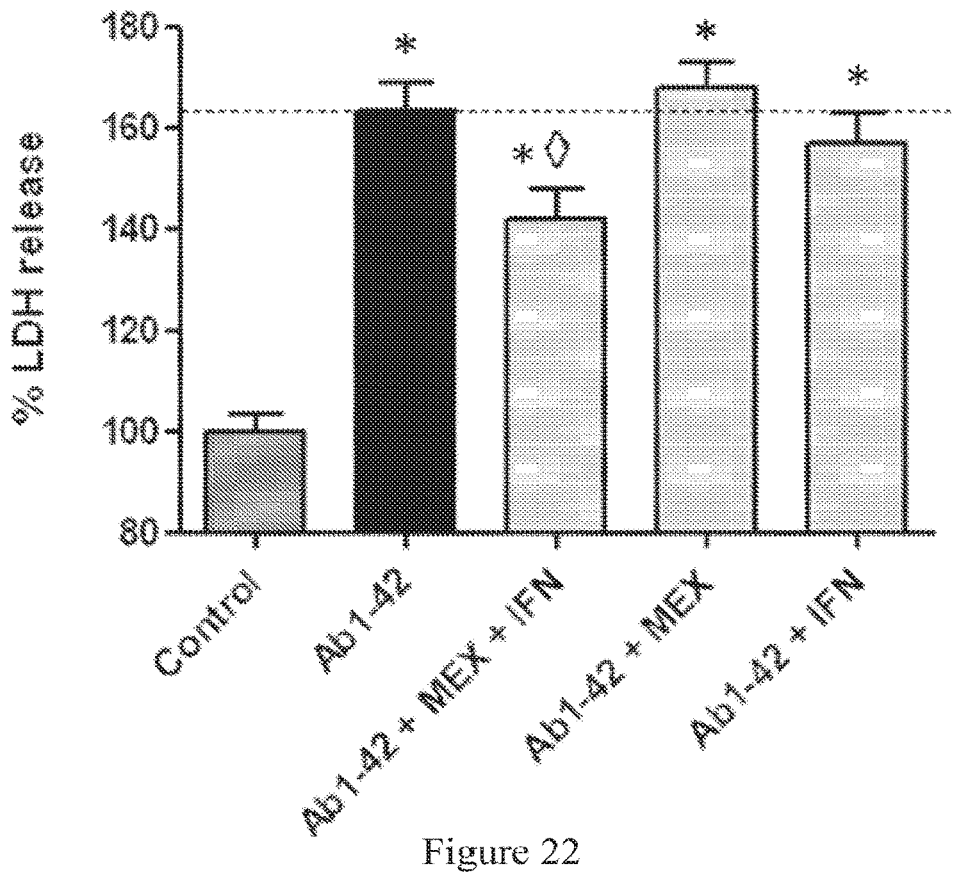
FIG. 22: Effect of Mexiletine (MEX) and Ifenprodil (IFN) combination therapy on LDH release in human A$\beta_{1-42}$, toxicity on rat primary cortical cells. The aggregated human amyloid peptide (A$\beta_{1-42}$ 10 µM) produces a significant intoxication compared to vehicle-treated neurons. This intoxication is significantly prevented by the combination of Mexiletine 25.6 pM and Ifenprodil 24 nM whereas, at those concentrations, Mexiletine and Ifenprodil alone have no significant effect on intoxication. ◇: $p<0.0572$, significantly different from A$\beta_{1-42}$ intoxication.

All values are expressed as mean±s.e. mean of the 3 cultures (n=6 per condition). Statistical analyses were done on the different conditions performing an ANOVA followed by the Dunnett's test when it was allowed (Statview software version 5.0). The values (as %) inserted on the graphs show the amyloid toxicity evolution. Indeed, the amyloid toxicity was taken as the 100% and the test compound effect was calculated as a % of this amyloid toxicity.
Results
Results are shown in FIG. 1. They demonstrate that the drugs tested alone, induce a substantial protective effect against the toxicity caused by Aβ peptide 1-42:
Torasemide, at a low dosage of e.g., 400 nM, induces strong protective effect;
Bromocriptine, at a low dosage of e.g., 3.2 nM, induces strong protective effect.
The results also show that, unexpectedly, upper or lower drug concentrations in comparison to the above mentioned drug concentrations, may worsen or rather have less to no effect on $A\beta_{1-42}$ toxicity in this model.
I.2 Protection Against the Toxicity of $A\beta_{1-42}$ on Primary Cortical Neuron Cells.
Test Compound and Human Amyloid-β1-42 Treatment
Rat cortical neurons were cultured as described by Singer et al. (42). Briefly pregnant female rats of 15 days gestation were killed by cervical dislocation (Rats Wistar) and the fetuses were removed from the uterus. The cortex was removed and placed in ice-cold medium of Leibovitz (L15) containing 2% of Penicillin 10.000 U/ml and Streptomycin 1.0 mg/ml and 1% of bovine serum albumin (BSA). Cortices were dissociated by trypsin for 20 min at 37° C. (0.05%), The reaction was stopped by the addition of Dulbecco's modified Eagle's medium (DMEM) containing DNase1 grade II and 10% of foetal calf serum (FCS). Cells were then mechanically dissociated by 3 serial passages through a 10 ml pipette and centrifuged at 515×g for 10 min at +4° C., The supernatant was discarded and the pellet of cells was re-suspended in a defined culture medium consisting of Neurobasal supplemented with B27 (2%), L-glutamine (0.2 mM), 2% of PS solution and 10 ng/ml of BDNF. Viable cells were counted in a Neubauer cytometer using the trypan blue exclusion test. The cells were seeded at a density of 30000 cells/well in 96 well lates (wells were pre-coated with poly-L-lysine (10 µg/ml)) and were cultured at ±37° C. in a humidified air (95%)/CO2 (5%) atmosphere.
Briefly, $A\beta_{1-42}$ peptide was reconstituted in define culture medium at 40 µM (mother solution) and was slowly shook at 1-37° C. for 3 days in dark for aggregation. The control medium was prepared in the same conditions.
After 3 days, the solution was used on primary cortical neurons as follows:
After 10 days of neuron culture, drug was solved in culture medium (+0.1% DMSO) and then pre-incubated with neurons for 1 hour before the $A\beta_{1-42}$ application (in a final volume per culture well of 100 µl). One hour after drug(s) incubation, 100 µl of $A\beta_{1-42}$ peptide was added to a final concentration of 10 µM diluted in presence of drug(s), in order to avoid further drug(s) dilutions. Cortical neurons were intoxicated for 24 hours. Three separate cultures were performed per condition, 6 wells per condition. BDNF (50 ng/ml) and Estradiol-β (150 nM) were used as positive control and reference compounds respectively.
Organization of Cultures Plates
Estradiol-β at 150 nM was used as a positive control.
Estradiol-β was solved in culture medium and pre-incubated for 1 h before t aggregated amyloid-$\beta_{1-42}$ application.
The following conditions were assessed:
CONTROL PLAQUE: 12 wells/condition
Negative Control: medium alone+0.1% DMSO intoxication: amyloid-$\beta_{1-42}$ (10 UM) for 24 h
Reference compound: Estradiol (150 nM) 1 hr.

Figure 26:
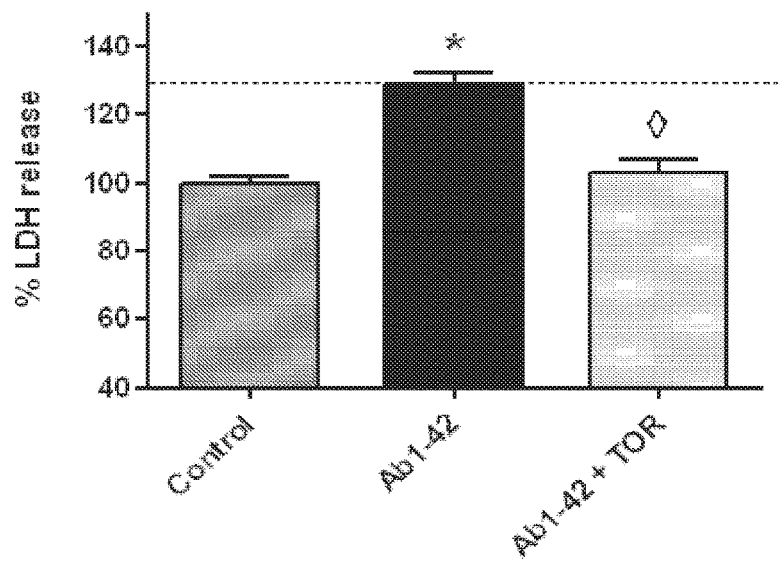
FIG. 26: Effect of Torasemide (TOR) pre-treatment on LDH release in human A$\beta_{1-42}$ toxicity assays on rat primary cortical cells. A$\beta_{1-42}$ produces a significant intoxication compared to vehicle-treated neurons. The intoxication is significantly prevented by Torasemide (200 nM, −90%). ◇: $p<0.0001$: significantly different from A$\beta_{1-42}$ intoxication.
Figure 27:
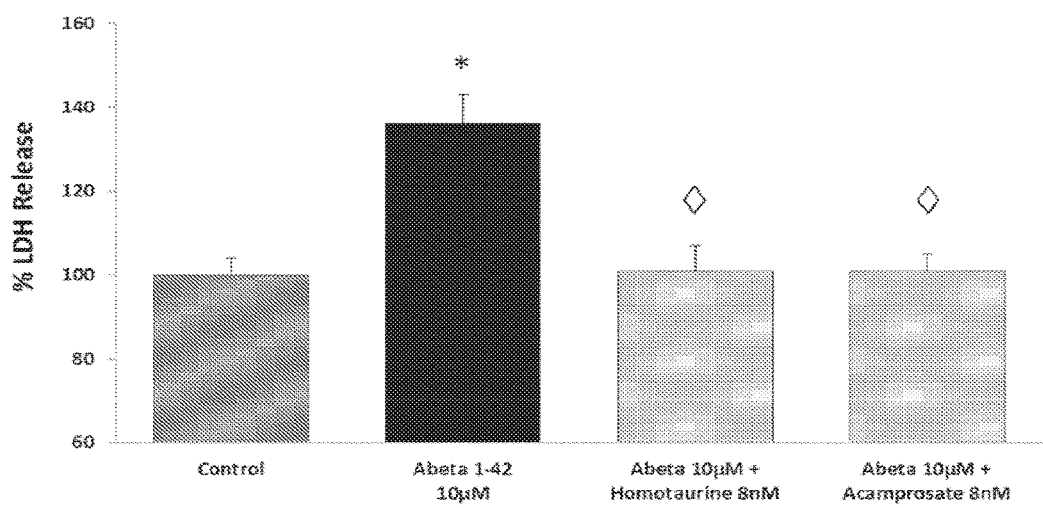
FIG. 27: Comparison of Acamprosate and its derivative Homotaurine pre-treatment on LDH release in human A$\beta_{1-42}$ toxicity assays on rat primary cortical cells. A$\beta_{1-42}$ produces a significant intoxication compared to vehicle-treated neurons. The intoxication is equally significantly prevented by Homotaurine and Acamprosate (99%, 8 nM). ◇: $p<0.0001$: significantly different from A$\beta_{1-42}$ intoxication.

DRUG PLATE: 6 wells/condition
Negative Control: medium alone+0.1% DMSO
Intoxication: amyloid-$\beta_{1-42}$ (10 µM) for 24 h
Drug: Drug—1 hr followed by amyloid-$\beta_{1-42}$ (10 µM) for 24 h Lactate Dehydrogenase (LDH) Activity Assay
24 hours after intoxication, the supernatant was taken off and analyzed with Cytotoxicity Detection Kit (LDH, Roche Applied Science, ref 11644793001, batch: 11800300). This colorimetric assay for the quantification of cell toxicity is based on the measurement of lactate dehydrogenase (LDH) activity released from the cytosol of dying cells into the supernatant.
Data Processing
All values are expressed as mean±s.e. mean of the 3 cultures (n=6 per condition). Statistic analyses were done on the different conditions (ANOVA followed by the Dunnett's test when it was allowed, Statview software version 5.0).
Results
The results obtained for individual selected drugs in the toxicity assays on primary cortical neuron cells are presented in FIGS. 2, 26 and 27. They demonstrate that the drugs tested alone, induce a substantial protective effect against the toxicity caused by Aβ peptide 1-42:
Trimetazidine, at a low dosage of e.g., 40 nM, induces strong protective effect;
Mexiletine, at a dose as low as 3.2 nM, induces a strong protective effect;
Bromocriptine, at a dose as low as 40 nM, induces a strong protective effect;
Ifenprodil, at a dose as low as 600 nM, induces a strong protective effect;
Moxifloxacin, at a dose as low as 20 nM, induces a strong protective effect.
Torasemide, at a dose of 200 nM, induces a strong protective effect.
Homotaurine, at a dose of 8 nM, induces a strong protective effect.
The obtained results also show that, unexpectedly, upper or lower drug concentrations than those indicated above, may worsen or rather have less to no protective effect on $A\beta_{1-42}$ toxicity for neuronal cells.
II. Combined Therapies Prevent Toxicity of Human $A\beta_{1-42}$
II.1 Effect of Combined Therapies on the Toxicity of Human $A\beta_{1-42}$ Peptide on Human HBMEC Cells.
The efficacy of drug combinations of the invention is assessed on human cells. The protocol which is used in these assays is the same as described in section I.1 above.
Results
All of the tested drug combinations give protective effect against toxicity of human $A\beta_{1-42}$ peptide in HBMEC model, as shown in table 3 below and exemplified in FIGS. 3 to 6 and FIGS. 13 and 14. The results clearly show that the intoxication by, aggregated human amyloid peptide ($A\beta_{1-42}$ 2.5 µm) is significantly prevented by combinations of the invention whereas, at those concentrations, drugs alone have no significant effect on intoxication in the experimental conditions described above.

TABLE 3

| DRUG COMBINATION | Protective effect in $A\beta_{1-42}$ intoxicated HBMEC cells |
|---|---|
| Baclofen and Torasemide | + |
| Eplerenone and Torasemide | + |

TABLE 3-continued

| DRUG COMBINATION | Protective effect in Aβ$_{1-42}$ intoxicated HBMEC cells |
|---|---|
| Bromocriptine and Sulfisoxazole | + |
| Sulfisoxazole and Torasemide | + |
| Terbinafine and Torasemide | + |
| Mexiletine and Cinacalcet | + |
| Baclofen and Trimetazidine and Torasemide | + |
| Baclofen and Cinacalcet and Torasemide | + |
| Baclofen and Acamprosate and Torasemide | + |
| Sulfisoxazole and Trimetazidine and Torasemide and Zonisamide | + |
| Sulfisoxazole and Mexiletine and Torasemide and Cinacalcet | + |
| Baclofen and Acamprosate and Torasemide and Diethylcarbamazine | + |
| Baclofen and Acamprosate and Torasemide and Ifenprodil | + |
| Levosimendan and Baclofen and Trimetazidine | + |
| Levosimendan and Aminocaproic acid and Trimetazidine | + |
| Levosimendan and Terbinafine and Trimetazidine | + |
| Levosimendan and Sulfisoxazole and Trimetazidine | + |

As exemplified in FIGS. 3 to 6, 13 and 14, the following drug combinations give particularly interesting protective effects against toxicity of human Aβ$_{1-42}$ peptide in intoxicated HBMEC cells:
  Baclofen and Torasemide,
  Sulfisoxazole and Torasemide,
  Torasemide and Eplerenone,
  Sulfisoxazole and Bromocriptine.
  Terbinafine and Torasemide, or
  Cinacalcet and Mexiletine.

II.2 Effect of Combined Therapies on the Toxicity of Human Aβ$_{1-42}$ Peptide on Primary Cortical Neuron Cells.

The efficacy of drug combinations of the invention is assessed on primary cortical neuron cells. The protocol which is used in these assays is the same as described in section I.2 above.

Results

All of the tested drug combinations give protective effect against toxicity of human Aβ$_{1-42}$ peptide in primary cortical neuron cells, as shown in Table 4 below and exemplified in FIGS. 7 to 12 and 16 to 22. The results clearly show that the intoxication by aggregated human amyloid peptide (Aβ$_{1-42}$ 10 µM) is significantly prevented by combinations of the invention whereas, at those concentrations, drugs alone have no significant effect on intoxication in the experimental conditions described above.

TABLE 4

| DRUG COMBINATIONS | Protective effect in Aβ$_{1-42}$ intoxicated primary cortical neuron cells |
|---|---|
| Acamprosate and Ifenprodil | + |
| Baclofen and Mexiletine | + |
| Baclofen and Trimetazidine | + |
| Baclofen and Torasemide | + |
| Cinacalcet and Mexiletine | + |
| Cinnarizine and Trimetazidine | + |
| Trimetazidine and Zonisamide | + |
| Levosimendan and Mexiletine | + |
| Levosimendan and Ifenprodil | + |
| Levosimendan and Trimetazidine | + |
| Levosimendan and Moxifloxacin | + |
| Mexiletine and Ifenprodil | + |
| Moxifloxacin and Baclofen | + |

TABLE 4-continued

| DRUG COMBINATIONS | Protective effect in Aβ$_{1-42}$ intoxicated primary cortical neuron cells |
|---|---|
| Moxifloxacin and Cinacalcet | + |
| Moxifloxacin and Trimetazidine | + |
| Moxifloxacin and Sulfisoxazole | + |
| Moxifloxacin and Zonisamide | + |
| Torasemide and Sulfisoxazole | + |
| Baclofen and Trimetazidine and Torasemide | + |
| Baclofen and Cinacalcet and Torasemide | + |
| Baclofen and Acamprosate and Torasemide | + |
| Sulfisoxazole and Trimetazidine and Torasemide and Zonisamide | + |
| Sulfisoxazole and Mexiletine and Torasemide and Cinacalcet | + |
| Baclofen and Acamprosate and Torasemide and Diethylcarbamazine | + |
| Baclofen and Acamprosate and Torasemide and Ifenprodil | + |
| Levosimendan and Baclofen and Trimetazidine | + |
| Levosimendan and Aminocaproic acid and Trimetazidine | + |
| Levosimendan and Terbinafine and Trimetazidine | + |
| Levosimendan and Sulfisoxazole and Trimetazidine | + |

As exemplified in FIGS. 7 to 12 and 15 to 22, the following drug combinations give particularly interesting protective effects against toxicity of human Aβ$_{1-42}$ peptide in intoxicated primary cortical neuron cells:
  Acamprosate and Ifenprodil,
  Baclofen and Mexiletine,
  Baclofen and Torasemide,
  Baclofen and Trimetazidine,
  Cinacalcet and Mexiletine,
  Cinnarizine and Trimetazidine,
  Trimetazidine and Zonisamide,
  Mexiletine and Ifenprodil,
  Moxifloxacin and Baclofen,
  Moxifloxacin and Cinacalcet,
  Moxifloxacin and Trimetazidine,
  Moxifloxacin and Sulfisoxazole,
  Moxifloxacin and Zonisamide, or
  Torasemide and Sulfisoxazole.

II.4. Protection of Neurite Growth Against Aβ$_{1-42}$ Toxicity.

Test Compounds and Aβ1-42 Treatment

Primary rat cortical neurons are cultured as described previously.

After 10 days of culture, cells are incubated with drugs. After 1 hour, cells are intoxicated by 2.5 µM of beta-amyloid (1-42; Bachem) in defined medium without BDNF but together with drugs. Cortical neurons are intoxicated for 24 hours. BDNF (10 ng/ml) is used as a positive (neuroprotective) control. Three independent cultures were performed per condition, 6 wells per condition.

Neurites Length

After 24 hours of intoxication, the supernatant is taken off and the cortical neurons are fixed by a cold solution of ethanol (95%) and acetic acid (5%) for 5 min, After permeabilization with 0.1% of saponin, cells are blocked for 2 h with PBS containing 1% foetal calf serum. Then, cells are incubated with monoclonal antibody anti microtubule-associated rotein 2 (MAP-2; Sigma). This antibody is revealed with Alexa Fluor 488 goat anti-mouse IgG (Molecular probe). Nuclei of neurons were labeled by a fluorescent marker (Hoechst solution, SIGMA).

Figure 23:
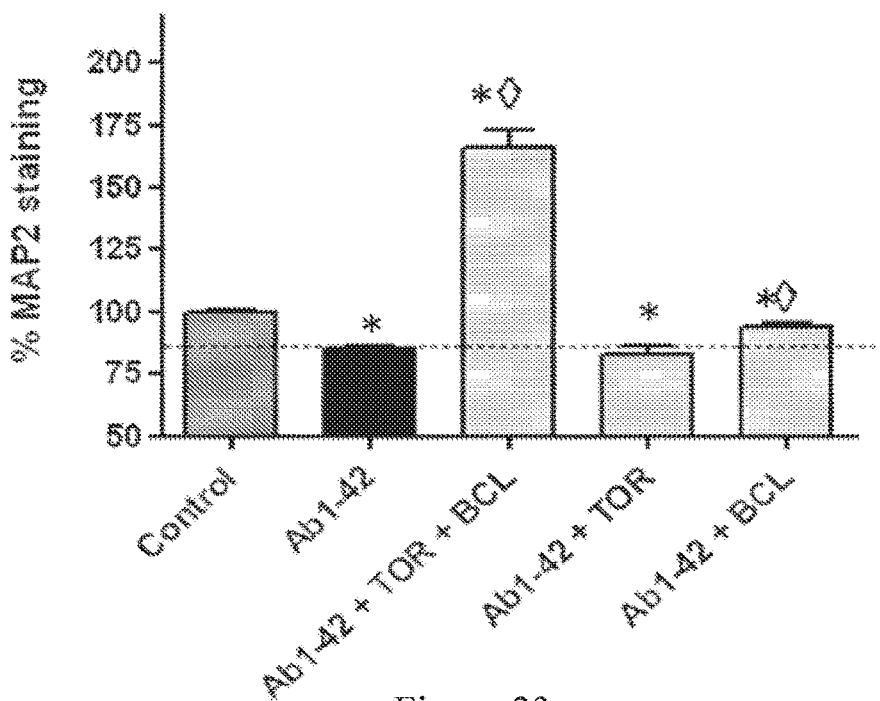
FIG. 23: Effect of Baclofen (BCL) and Torasemide (TOR) combination therapy on the total length of neurites network in beta-amyloid intoxicated cortical neurons. The human amyloid peptide (A$\beta_{1-42}$ 2.5 µM) produces a significant intoxication, above 15%, compared to vehicle-treated cells. This intoxication is significantly prevented by the combination of Torasemide and Baclofen; furthermore this combination allows an enhancement of neurite growth. ◇: $p<0.05$, significantly different from A$\beta_{1-42}$ intoxication.

Per well, 10 pictures are taken using InCell Analyzer™ 1000 (GE Healthcare) with 20× magnification. All pictures are taken in the same conditions. Analysis of the neurite network is done using Developer software (GE Healthcare) in order to assess the total length of neurite network.
Results The combination of Baclofen and Torasemide induces a significant protective effect against the toxicity of human $A\beta_{1-42}$ peptide (improvement of 531% of neurites network) in primary cortical neuron cells as shown in FIG. 23. The results clearly show that the intoxication by human amyloid peptide ($A\beta_{1-42}$ 2.5 μM) is significantly prevented by the combination and that, moreover, the combination enhances neurite network in comparison with control.

Hence, this combination allows an effective protection of cortical neuron cells and of cell neuronal networks against the toxicity of human $A\beta_{1-42}$ peptide. Moreover, such an augmentation of neurites network confirms the efficacy of such drugs in neurological disorders like spinal cord injury.

III. The Compounds Prevent Toxicity of Human $A\beta_{25-35}$ In Vivo

Animals

Male Swiss mice are used throughout the study. Animals are housed in plastic cages, with free access to laboratory chow and water, except during behavioural experiments, and kept in a regulated environment, under a 12 h light/dark cycle (light on at 8:00 a.m.). Behavioral experiments are carried out in a soundproof and air-regulated experimental room, to which mice have been habituated at least 30 min before each experiment.

Amyloid Peptide Preparation and Infection

The $A\beta_{25\;35}$ peptide and scrambled $A\beta_{25\;35}$ peptide have been dissolved in sterile bidistilled water, and stored at –20° C. until use. Light microscopic observation indicated that incubating the $A\beta_{25-35}$ peptide, but not the scrambled $A\beta_{25-35}$ peptide, led the presence of two types of insoluble precipitates, birefringent fibril-like structures and amorphous globular aggregates. The ii-amyloid peptides are then administered intracerebroventricularly (i.c.v.). In brief, each mouse is anaesthetized lightly with ether, and a gauge stainless-steel needle is inserted unilaterally 1 mm to the right of the midline point equidistant from each eye, at an equal distance between the eyes and the ears and perpendicular to the plane of the skull. Peptides or vehicle are delivered gradually within approximately 3 s. Mice exhibit normal behaviour within 1 min after injection. The administration site is checked by injecting Indian ink in preliminary experiments. Neither insertion of the needle, nor injection of the vehicle have had a significant influence on survival, behavioral responses or cognitive functions.

Drug(s) Treatment

On day –1, i.e. 24 h before the $A\beta_{25-35}$ peptide injection, drugs, drugs combination or the vehicle solution are administered per os by gavage twice daily (at 8:00 am and 6:00 pm).

On day 0 (at 10:00 am), mice are injected i.c.v. with Aβ25-35 peptide or scrambled Aβ 25-35 peptide (control) in a final volume of 3 μl (3 mM).

Between day 0 and day 7, drugs, drugs combination or the vehicle solution are administered per os by gavage once or twice daily (at 8:00 am and 6:00 pm). One animal group receives donepezil (reference compound—1 mg/kg/day) per os by gavage in a single injection (at 8:00 am). Drugs are solubilized in water and freshly prepared just before each gavage administration.

On day 7, all animals are tested for the spontaneous alternation performance in the Y-maze test, an index of spatial working memory.

On day 7 and 8, the contextual long-term memory of the animals is assessed using the step-down type passive avoidance procedure.

On day 8, animals are sacrificed. Their brain is dissected and kept at –80° C. for further analysis.

Positive results are observed in behavioral performances and biochemical assays performed 7 days after $A\beta_{25-35}$ peptide icy injection, notably for the combinations listed in table 5.

TABLE 5

| DRUG COMBINATIONS | Results in biochemical and/or behavioral assays |
|---|---|
| Baclofen and Torasemide | + |
| Mexiletine and Cinacalcet | + |
| Sulfisoxazole and Torasemide | + |
| Baclofen and Trimetazidine and Torasemide | + |
| Baclofen and Cinacalcet and Torasemide | + |
| Baclofen and Acamprosate and Torasemide | + |
| Sulfisoxazole and Trimetazidine and Torasemide and Zonisamide | + |
| Sulfisoxazole and Mexiletine and Torasemide and Cinacalcet | + |
| Baclofen and Acamprosate and Torasemide and Diethylcarbamazine | + |
| Baclofen and Acamprosate and Torasemide and Ifenprodil | + |
| Levosimendan and Baclofen and Trimetazidine | + |
| Levosimendan and Aminocaproic acid and Trimetazidine | + |
| Levosimendan and Terbinafine and Trimetazidine | + |
| Levosimendan and Sulfisoxazole and Trimetazidine | + |

IV Compounds Enhanced Behavioral and Cognitive Performances of Intoxicated Animals Animals are intoxicated as in the above section.

Spontaneous Alternation Performances—Y Maze Test

On day 7, all animals are tested for spontaneous alternation performance in the Y-maze, an index of spatial working memory. The Y-maze is made of grey polyvinylchloride. Each arm is 40 cm long, 13 cm high, 3 cm wide at the bottom, 10 cm wide at the top, and converging at an equal angle. Each mouse is placed at the end of one arm and allowed to move freely through the maze during an 8 min session. The series of arm entries, including possible returns into the same arm, are checked visually. An alternation is defined as entries into all three arms on consecutive occasions. The number of maximum alternations is therefore the total number of arm entries minus two and the percentage of alternation is calculated as (actual alternations/maximum alternations)×100. Parameters include the percentage of alternation (memory index) and total number of arm entries (exploration index). Animals that show an extreme behavior (Alternation percentage <25% or >85% or number of arm entries <10) are discarded. Usually, it accounts for 0-5% of the animals. This test incidentally serves to analyze at the behavioral level the impact and the amnesic effect induced in mice by the Aβ25-35 injection.

Passive Avoidance Test

The apparatus is a two-compartment (15×20×15 cm high) box with one illuminated with white polyvinylchloride walls and the other darkened with black polyvinylchloride walls and a grid floor. A guillotine door separates each compartment. A 60 W lamp positioned 40 cm above the apparatus lights up the white compartment during the experiment. Scrambled footshocks (0.3 mA for 3 s) could be delivered to the grid floor using a shock generator scrambler (Lafayette Instruments, Lafayette, USA). The guillotine door is initially closed during the training session. Each mouse is placed into the white compartment. After 5 s, the door raises. When the mouse enters the darkened compartment and places all its paws on the grid floor, the door closes and the footshock is delivered for 3 s. The step-through latency, that is, the latency spent to enter the darkened compartment, and the number of vocalizations is recorded. The retention test is carried out 24 h after training. Each mouse is placed again into the white compartment. After 5 s the doors is raised, the step-through latency and the escape latency, i.e. the time spent to return into the white compartment, are recorded up to 300 s.

Positive results are observed for each for the tested combinations listed in Table 6.

TABLE 6

| Drug Combination | Y MAZE test | Passive avoidance | |
|---|---|---|---|
| | | Escape latency | Step through latency |
| Baclofen-Torasemide | + | + | + |
| Baclofen-Acamprosate-Torasemide | + | + | + |
| Mexiletine and Cinacalcet | + | + | + |
| Sulfisoxazole and Torasemide | + | + | + |

V Compounds of the Invention Improve Neurophysiological Concern of Neurological Diseases Combinations therapies are tested in the in vivo model of Aβ intoxication. Their effects on several parameters which are affected in neurological diseases are assessed:
  Caspases 3 and 9 expression level, considered as an indicator of apoptosis,
  Lipid peroxidation, considered as a marker for oxidative stress level,
  GFAP expression assay, considered as a marker of the level of brain inflammation,
  Brain Blood Barrier integrity,
  Overall synapse integrity (synaptophysin ELISA).

Brain Blood Barrier Integrity

Experimental design about animal intoxication by AP is the same that in part III.

The potential protective effect of the combination therapies on the blood brain barrier (BBB) integrity is analyzed in mice injected intracerebroventricularly (i.c.v.) with oligomeric amyloid-β25-35 peptide (Aβ25-35) or scrambled Aβ25-35 control peptide (Sc.Aβ), 7 days after injection.

On day 7 after the $A\beta_{25-35}$ injection, animals are tested to determine the BBB integrity by using the EB (Evans Blue) method. EB dye is known to bind to serum albumin after peripheral injection and has been used as a tracer for serum albumin.

EB dye (2% in saline, 4 ml/kg) is injected intraperitoneal (i.p.) 3 h prior to the transcardiac perfusion. Mice are then anesthetized with i.p. 200 µl of pre-mix ketamine 80 mg/kg, xylazine 10 mg/kg, the chest is opened. Mice are perfused transcardially with 250 ml of saline for approximately 15 min until the fluid from the right atrium becomes colourless. After decapitation, the brain is removed and dissected out into three regions: cerebral cortex (left+right), hippocampus (left+right), diencephalon. Then, each brain region is weighed for quantitative measurement of EB-albumin extravasation.

Samples are homogenized in phosphate-buffered saline solution and mixed by vortexing after addition of 60% trichloroacetic acid to precipitate the protein. Samples are cooled at 4° C., and then centrifuged 30 min at 10,000 g, 4° C. The supernatant is measured at 610 nm for absorbance of EB using a spectrophotometer.

EB is quantified both as
  µg/mg of brain tissue by using a standard curve, obtained by known concentration of EB-albumin.
  µg/mg of protein.

As mentioned in table 7, combination therapies of the invention are efficient in maintaining BBB integrity when compared with non-treated intoxicated animals.

Overall Synapse Integrity (Synaptophysin ELISA)

Synaptophysin has been chosen as a marker of synapse integrity and is assayed using a commercial ELISA kit (USCN, Ref. E90425Mu). Samples are prepared from hippocampus tissues and homogenized in an extraction buffer specific to as described by manufacturer and reference literature.

Tissues are rinsed in ice-cold PBS (0.02 mol/l, pH 7.0-7.2) to remove excess blood thoroughly and weighed before nitrogen freezing and −80° C. storage. Tissues are cut into small pieces and homogenized in 1 ml ice-cold phosphate buffer saline (PBS) solution with a glass homogenizer. The resulting suspension is sonicated with an ultrasonic cell disrupter or subjected to two freeze-thawing cycles to further break the cell membranes. Then, homogenates are centrifugated for 5 min at 5,000 g and the supernatant is assayed immediately.

All samples are assayed in triplicates.

Quantification of proteins is performed with the Pierce BCA (bicinchoninic acid) protein assay kit (Pierce, Ref. #23327) to evaluate extraction performance and allow normalization.

The total protein concentrations are then calculated from standard curve dilutions and serve to normalize ELISA results.

Results (Table 7) show that combination therapies are efficient in maintaining an overall Synaptophysin level in brain of treated animals when compared with the non-treated intoxicated animals.

Oxidative Stress Assay

Mice are sacrificed by decapitation and both hippocampi are rapidly removed, weighted and kept in liquid nitrogen until assayed. After thawing, hippocampus are homogenized in cold methanol (1/10 w/v), centrifuged at 1,000 g during 5 min and the supernatant placed in eppendorf tube. The reaction volume of each homogenate are added to FeSO4 1 mM, H2SO4 0.25 M, xylenol orange 1 mM and incubated for 30 min at room temperature. After reading the absorbance at 580 nm (A580 1), 10 µl of cumene hydroperoxyde 1 mM (CHP) is added to the sample and incubated for 30 min at room temperature, to determine the maximal oxidation level. The absorbance is measured at 580 nm (A580 2). The level of lipid peroxidation is determined as CHP equivalents (CHPE) according to: CHPE=A580 1/A580 2×[CHP] and expressed as CHP equivalents per weight of tissue and as percentage of control group data.

Results (Table 7) show that combination therapies are efficient in reducing the overall oxidative stress induced by Aβ in brain of treated animals when compared with the non-treated intoxicated animals.

Caspase Pathway Induction Assay and GFAP Expression Assay

Mice are sacrificed by decapitation and both hippocampi are rapidly removed, rinsed in ice-cold PBS (0.02 mol/l, pH 7.0-7.2) to remove excess blood thoroughly and weighted and kept in liquid nitrogen until assayed. Tissues are cut into small pieces and homogenized in 1 ml ice-cold PBS with a glass homogenizer. The resulting suspension is sonicated with ultrasonic cell disrupter or subjected to two freeze-thawing cycles to further break the cell membranes. Then, homogenates are centrifugated at 5,000 g during 5 min and the supernatant is assayed immediately.

Experiments are conducted with commercial assay: Caspase-3 (USCN—E90626Mu), Caspase-9 (USCN—E90627Mu), GFAP (USCN—E90068). Quantification of proteins is performed with the Pierce BCA (bicinchoninic acid) protein assay kit (Pierce, Ref. #23227) to evaluate extraction performance and allow normalization.

Results (Table 7) show that combination therapies have a positive effect on markers of apoptosis and inflammation in brain of treated animals when compared with the non-treated intoxicated animals.

TABLE 7

| Drug Combination | Caspase pathway | Oxydative stress | GFAP expression | BBB integrity | Overall Synapse integrity |
|---|---|---|---|---|---|
| Baclofen-Torasemide | + | + | + | + | + |
| Baclofen-Acamprosate-Torasemide | + | + | + | + | + |
| Mexiletine and Cinacalcet | + | + | + | + | + |
| Sulfisoxazole and Torasemide | + | + | + | + | + |

B) Prevention of Glutamate Toxicity on Neuronal Cells

In this further set of experiment, candidate compounds have been tested for their ability to prevent or reduce the toxic effects of glutamate toxicity on neuronal cells. Glutamate toxicity is involved in the pathogenesis of neurological diseases or disorder such as Multiple Sclerosis, Alzheimer's Disease, Amyotrophic Lateral Sclerosis, Parkinson's Disease, Huntington's Disease, neuropathies, alcoholism or alcohol withdrawal, or spinal cord injury. The drugs are first tested individually, followed by assays of their combinatorial action.

Methods

The efficacy of drug combinations of the invention is assessed on primary cortical neuron cells. The protocol which is used in these assays is the same as described in section A.I.2 above.

Glutamate Toxicity Assays

The neuroprotective effect of compounds is assessed by quantification of the neurite network (Neurofilament immunostaining (NE)) which specifically reveals the glutamatergic neurons.

After 12 days of neuron culture, drugs of the candidate combinations are solved in culture medium (+0% DMSO). Candidate combinations are then pre-incubated with neurons for 1 hour before the Glutamate injury. One hour after incubation with, Glutamate is added for 20 min, to a final concentration of 40 µM, in presence of candidate combinations, in order to avoid further drug dilutions. At the end of the incubation, medium is changed with medium with candidate combination but without glutamate. The culture is fixed 24 hours after glutamate injury. MK801 (Dizocilpine-hydrogen maleate, 77086-22-7-20 µM) is used as a positive control.

After permeabilization with saponin (Sigma), cells are blocked for 2 h with PBS containing 10% goat serum, then the cells are incubated with mouse monoclonal primary antibody against Neurofilament antibody (NF, Sigma). This antibody is revealed with Alexa Fluor 488 goat anti-mouse IgG.

Nuclei of cells are labeled by a fluorescent marker (Hoechst solution, SIGMA), and neurite network quantified. Six wells per condition are used to assess neuronal survival in 3 different cultures.

Results

All of the tested drug combinations give a protective effect against glutamate toxicity for cortical neuronal cells. Results are shown in Table 8 below.

Figure 24:
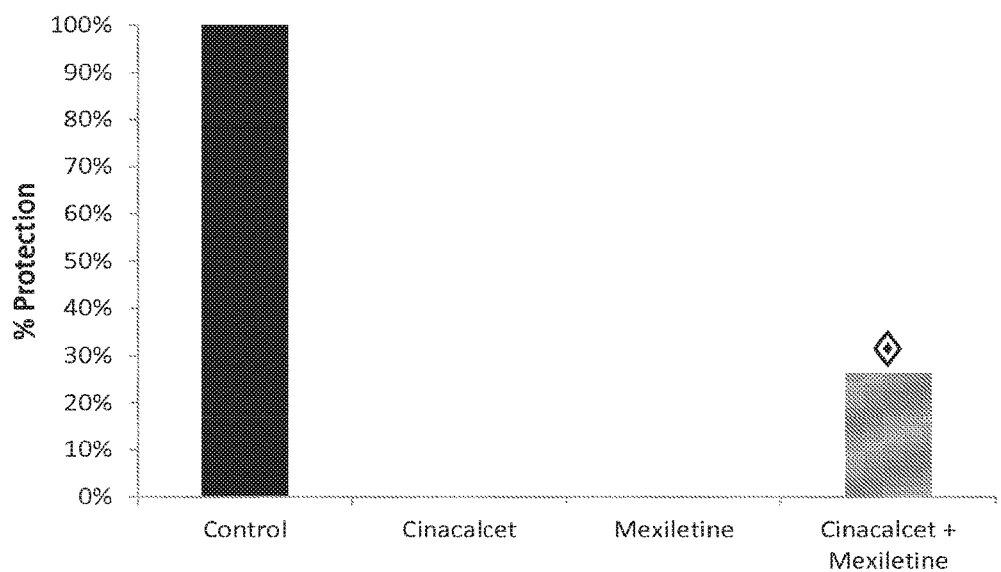
FIG. 24: Effect of Cinacalcet and Mexiletine combination therapy against glutamate toxicity on neuronal cortical cells. The glutamate intoxication is significantly prevented by the combination of Cinacalcet (64 pM) and Mexiletine (25.6 pM) whereas, at those concentrations, Cinacalcet and Mexiletine alone have no significant effect on intoxication. ◇: $p<0.001$, significantly different from glutamate intoxication; (ANOVA+Dunnett Post-Hoc test).
Figure 25:
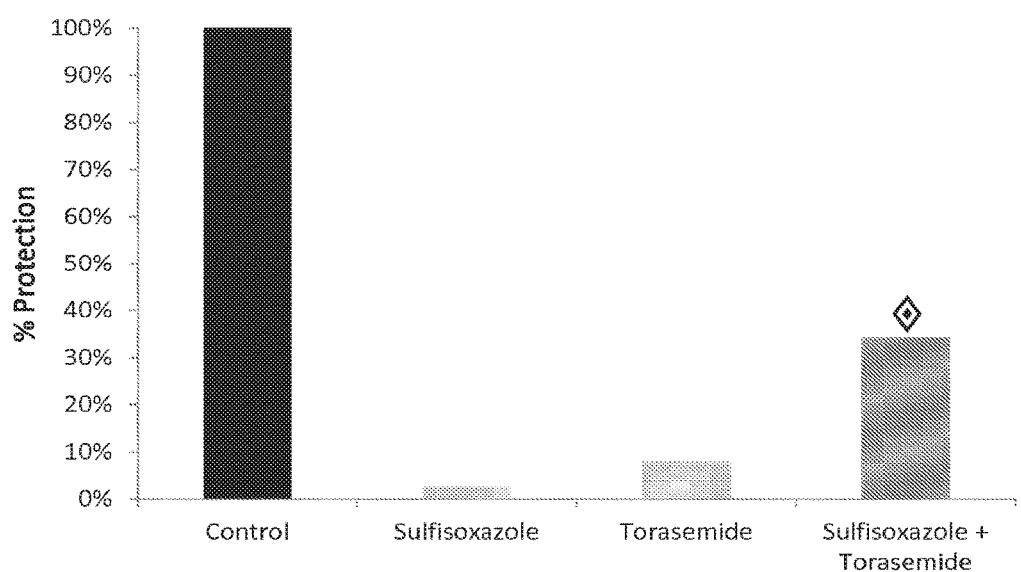
FIG. 25: Effect of Sulfisoxazole and Torasemide combination therapy against glutamate toxicity on neuronal cortical cells. The glutamate intoxication is significantly prevented by the combination of Sulfisoxazole (6.8 nM) and Torasemide (400 nM) whereas, at those concentrations, Sulfisoxazole and Torasemide alone have no significant effect on intoxication. ◇: $p<0.001$; significantly different from glutamate intoxication; (ANOVA+Dunnett Post-Hoc test).

As exemplified in FIGS. 24 and 25, combinations of the invention strongly protect neurons from glutamate toxicity under experimental conditions described above. It is noteworthy that an effective protection is noticed using drug concentrations at which drugs used alone have no significant or lower protective effect.

TABLE 8

| Drug Combination | Neuroprotective effect against glutamate toxicity |
|---|---|
| Baclofen-Torasemide | + |
| Baclofen-Acamprosate-Torasemide | + |
| Mexiletine and Cinacalcet | + |
| Sulfisoxazole and Torasemide | + |

C) Improvement of Other Disorders Related to Glutamate Excitoxicity Using Combinations of the Invention The above mentioned in vitro protective effect against glutamate toxicity of drugs and drug combinations of the invention combined with the protective effects exemplified herein in several AD models, prompted the inventors to test these drugs and combinations in some models of other diseases in the pathogenesis of which glutamate toxicity is also involved, as MS, ALS and neuropathic pain.

I) Protective Effect of Combinations in an In Vivo Model of Multiple Sclerosis.

A model in which myelin-oligodendrocyte glycoprotein-immunized (MOG-immunized) mice develop chronic progressive EAE is used to demonstrate the beneficial effect of compositions of the invention in multiple sclerosis treatment.

Animals and Chemicals

C57L/6J female mice (8 weeks old) are purchased from Janvier (France); after two weeks of habituation, female mice (10 weeks old) develop chronic paralysis after immunization with MOG (Myelin Oligodendrocyte Glycoprotein) peptide. The experimental encephalomyelitis is induced with the Hooke Kit $MOG_{35-55}$/CFA Emulsion PTX (Pertussis toxin) for EAE Induction (EK-0110, EK-0115; Hooke laboratories). The control kit is CK-0115 (Hooke laboratories).

Experimental Procedure

The experimental encephalomyelitis is induced by following procedure:

The day 0, two subcutaneous injections of 0.1 Ml each are performed; one on upper back of the mouse and one in lower back. Each injection contains 100 µg of $MOG_{15-55}$ peptide (MEVGWYRSPFSRVVHLYRNGK, SEQ ID NO: 1), 200 µg of inactivated *Mycobacterium tuberculosis* *H*37Ra and is emulsified in Complete Freund's adjuvant (CFA) (Hooke laboratories). The emulsion provides antigen needed to expand and differentiate MOG-specific autoimmune T cells.

Two intraperitoneal injections of 500 ng of Pertussis toxin in PBS (Hooke kit) are performed 2 hours (Day 0) and 24 hours (Day 1) after the MUG injection. Pertussis toxin enhances EAE development by providing additional adjuvant.

Mice develop EAE 8 days after immunization and stay chronically paralyzed for the duration of the experiment. After the immunization, mice are daily observed for clinical symptoms in a blind procedure. Animals are kept in a conventional pathogen-free facility and all experiments are carried out in accordance with guidelines prescribed by, and are approved by, the standing local committee of bioethics.

Experimental Groups and Drug Treatment

Groups of female mice as disclosed are homogenized by weight before the immunization:
- Control group: vehicle injection in the same conditions of EAE mice (from Day −1 to Day 28, placebo is given daily)
- EAE group: MOG injection (day 0)+Pertussis toxin injections (Day 0 and 1)—from Day −1 to Day 28, placebo is given orally daily
- EAE+positive control: MUG injection (Day 0)+Pertussis toxin injections (Day 0 and 1)—from Day −1 to Day 28, dexamethazone is given orally daily.
- EAE+treatment group: MOG injection (Day 0)+Pertussis toxin injections (Day 0 and 1). The treatments start one Day before immunization and last until Day 28.

The clinical scores are measured at Days 0-5-8-9-12-14-16-19-21-23-26-28.

Statistica software (Statsoft Inc.) is utilized throughout for statistical analysis. ANOVA analysis and Student's t test are employed to analyse clinical disease score. P<0.05 is considered significant.

Delays of disease occurrence, clinical score and delay of death, have been compared between each group to the reference 'immu' group with Kaplan-Meier curves and a Cox model (R package 'survival'). Resulting p-values are unilateral and test the hypothesis to be better than the reference 'immu' group.

The total clinical score is composed of the tail score, the hind limb score, the fore limb score and the bladder score described as below:

| Tail score: | |
|---|---|
| Score = 0 | A normal mouse holds its tail erect when moving. |
| Score = 1 | If the extremity of the tail is flaccid with a tendency to fall. |
| Score = 2 | If the tail is completely flaccid and drags on the table. |

| Hind limbs score: | |
|---|---|
| Score = 0 | A normal mouse has an energetic walk and doesn't drag his paws |
| Score = 1 | Either one of the following tests is positive:<br>A - Flip test: while holding the tail between thumb and index finger, flip the animal on his back and observe the time it takes to right itself. A healthy mouse will turn itself immediately. A delay suggests hind-limb weakness.<br>B - Place the mouse on the wire cage top and observe as it crosses from one side to the other. If one or both limbs frequently slip between the bars we consider that there is a partial paralysis. |
| Score = 2 | Both previous tests are positive. |
| Score = 3 | One or both hind limbs show signs of paralysis but some movements are preserved; for example: the animal can grasp and hold on to the underside of the wire cage top for a short moment before letting go. |
| Score = 4 | When both hind legs are paralyzed and the mouse drags them when moving. |

| Fore limbs score: | |
|---|---|
| Score = 0 | A normal mouse uses its front paws actively for grasping and walking and holds its head erect. |
| Score = 1 | Walking is possible but difficult due to a weakness in one or both of the paws, for example, the front paws are considered weak when the mouse has difficulty grasping the underside of the wire top cage. Another sign of weakness is head drooping. |
| Score = 2 | When one forelimb is paralyzed (impossibility to grasp and the mouse turns around the paralyzed limb). At this time the head has also lost much of its muscle tone. |
| Score = 3 | Mouse cannot move, and food and water are unattainable. |

| Bladder score: | |
|---|---|
| Score = 0 | A normal mouse has full control of its bladder. |
| Score = 1 | A mouse is considered incontinent when its lower body is soaked with urine. |

The global score for each animal is determined by the addition of all the above mentioned categories. The maximum score for live animals is 10.

Results-Combinations Therapies are Efficient in a MS Model

A significant improvement of global clinical score is observed in "EAE+ treatment group" mice, notably for the combinations listed in Table 9.

TABLE 9

| Drug Combination | Improvement of the global clinical score in EAE animals |
|---|---|
| Baclofen-Torasemide | + |
| Baclofen-Acamprosate-Torasemide | + |
| Mexiletine and Cinacalcet | + |
| Sulfisoxazole and Torasemide | + |

II. Protective Effect of Combinations in Models of ALS.

Combination therapies according to the present invention are tested in vitro, in a coculture model, and in vivo, in a mouse model of ALS. Protocols and results are presented in this section.

II.1 Protective Effect Against Glutamate Toxicity in Primary Cultures of Nerve-muscle Co-culture Primary Cocultures of Nerve- and Muscle Cells Human muscle is prepared according to a previously described method from portions of biopsie of healthy patient (44). Muscle cells are established from dissociated cells (10000 cells per wells), plated in gelatin-coated 0.1% on 48 wells plate and grown in a proliferating medium consisting of mix of MEM medium and M199 medium.

Immediately after satellite cells fusion, whole transverse slices of 13-day-old rat Wistar embryos spinal cords with dorsal root ganglia (DRG) attached are placed on the muscle monolayer 1 explant per well (in center area). DRG are necessary to achieve a good ratio of innervations, innervated cultures are maintained in mix medium, After 24 h in the usual co-culture neuritis are observed growing out of the spinal cord explants. They make contacts with myotubes and induce the first contractions after 8 days. Quickly thereafter, innervated muscle fibres located in proximity to the spinal cord explants, are virtually continuously contracting. Innervated fibres are morphologically, and spatially distinct from the non-innervated ones and could easily be distinguished from them.

One co-culture is done (6 wells per conditions).

Glutamate Injury

On day 27, co-cultures are incubated with candidate compounds or Riluzole one hour before glutamate intoxication (60 µM) for 20 min. Then, co-cultures are washed and candidate compounds or Riluzole are added for an additional 48 h. After this incubation time, unfixed cocultures are incubated with α-bungarotoxin coupled with Alexa 488 at concentration 500 nmol/L for 15 min at room temperature. Then, cocultures fixed by PFA for 20 min at room temperature. After permeabilization with 0.1% of saponin, co-cultures are incubated with anti-neurofilament antibody (NF).

These antibodies are detected with Alexa Fluor 568 goat anti-mouse IgG (Molecular probe). Nuclei of neurons are labeled by a fluorescent marker (Hoechst solution).

Endpoints are (1) Total neurite length, (2) Number of motor units, (3) Total motor unit area, which are indicative of motorneurone survival and functionality. For each condition, 2×10 pictures per well are taken using InCell Analyzer™ 1000 (GE Healthcare) with 20× magnification. All the images are taken in the same conditions.

Results

Drugs of the invention effectively protect motorneurones and motor units in the coculture model. Moreover an improvement of the protection is noticed when drugs are used in combination for the drug combinations listed in table 10.

TABLE 10

| Drug Combination | Protective effect against glutamate intoxication in muscle/nerve co-cultures |
|---|---|
| Baclofen-Torasemide | + |
| Baclofen-Acamprosate-Torasemide | + |
| Mexiletine and Cinacalcet | + |
| Sulfisoxazole and Torasemide | + |

II.2 Combinations Therapies are Efficient in ALS Mouse Model

Experiments are performed on male mice, Transgenic male mice B6SJL-Tg(SOD1)2Gur/J mice and their control (respectively SN2726 and SN2297 from Jackson Laboratories, Ben Harbor, USA and distributed by Charles River in France) are chosen in this set of experiments to mimic ALS.

Diseased mice express the SOD1-G93A transgene, designed with a mutant human SOD1 gene (a single amino acid substitution of glycine to alanine at codon 93) driven by its endogenous human SOD1 promoter. Control mice express the control human SOD1 gene.

Drug Administration

Mice are dosed with candidate drug treatment diluted in vehicle from 60th day after birth till death, Diluted solutions of drug candidates are prepared with water at room temperature just before the beginning of the administration.

In drinking water:

Riluzole is added in drinking water at a final concentration of 6 mg/ml (adjusted to each group mean body weight) in 5% cyclodextrin. As a mouse drinks about 5 ml/day, the estimated administrated dose is 30 mg/kg/day which is a dose that was shown to increase the survival of mice.

Cyclodextrine is used as vehicle at the final concentration of 5%, diluted in water at room temperature from stock solution (cyclodextrin 20%).

Oral administration (per os):

Drug combinations are administrated per os, daily.

Cyclodextrine is used as vehicle at the final concentration of 5%, diluted in water at room temperature from stock solution (cyclodextrin 20%).

Clinical Observation

The clinical observation of each mouse is performed daily, from the first day of treatment (60 days of age) until the death (or sacrifice). Clinical observation consists in studying behavioural tests: onset of paralysis, "loss of splay", "loss of righting reflex", and general gait observation:

Onset of paralysis: The observation consists of paralysis observation of each limb. Onset of paralysis corresponds to the day of the first signs of paralysis.

The loss of splay test consists of tremors or shaking notification and the position of hind limb (hanging or splaying out) when the mouse is suspended by the tail.

The loss of righting reflex test evaluates the ability of the mouse to right itself within 30 sec of being turned on either side. The righting reflex is lost when the mouse is unable to right itself. The loss of righting reflex determines the end stage of disease: the mouse unable to right itself is euthanized.

Results-Combinations Therapies are Efficient in ALS In Vivo Model

An improvement of the disease is observed for the diseased animals treated with the drugs and drug combinations of the invention. Notably, drugs combinations listed in Table 11 efficiently improve clinical score of these animals during the different stage of the disease.

TABLE 11

| Drug Combination | Effect on clinical score in diseased animals |
|---|---|
| Baclofen-Torasemide | + |
| Baclofen-Acamprosate-Torasemide | + |
| Mexiletine and Cinacalcet | + |
| Sulfisoxazole and Torasemide | + |

III) Protective Effect of Combinations of the Invention in Oxaliplatin Induced Neuropathy as an In Vivo Model for Neuropathic Pain.

Combinatorial therapies of the present invention are tested in vivo, in suitable models of peripheral neuropathy, i.e., acute model of oxaliplatin-induced neuropathy and chronic model of oxaliplatin-induced neuropathy. The animals, protocols and results are presented in this section.

Animal Husbandry

Sprague-Dawley rats (CERJ, France), weighing 150-175 g at the beginning of the experimental of the Oxaliplatin treatment ($D_0$) are used. Animals are housed in a limited access animal facility in a temperature (19.5° C.-24.5° C.) and relative humidity, (45%-65%) controlled room with a 12 h-light/dark cycle, with ad libitum access to standard pelleted laboratory chow and water throughout the study. Animals are housed 4 or 5 per cage and a one week-acclimation period is observed before any testing.

Experimental Design

Four following groups of rats are used in all experiments:

Control Groups:

Group 1: Vehicle of Oxaliplatin (distilled water), i.p./Vehicle of candidate combination(s) (Distilled water), p.o. daily.

Group 2: Oxaliplatin (distilled water), i.p./Vehicle of candidate combination(s) (Distilled water), p.o. daily.

Group 3: Oxaliplatin 3 mg/kg i.p./single drug in Distilled water, p.o. daily×9.

Tested Composition Groups:

Group 4: Oxaliplatin 3 mg/kg i.p./candidate combination(s) in Distilled water, p.o. daily×9.

Group 5: Oxaliplatin 3 mg/kg i.p./Gabapentin (100 mg/kg) in Distilled water, p.o. on testing days (i.e. $D_1$ & $D_8$);

Vehicle and test items are delivered daily from D−1 to D7 (the day before the last testing day) whereas Gabapentin is administered on testing days (120 minutes before the test).

All treatments are administered in a coded and random order when it is possible. Doses are expressed in terms of free active substance.

Neuropathy Induction

Acute neuropathy is induced by a single intraperitoneal injection of oxaliplatin (3 mg/kg).

Chronic peripheral neuropathy is induced by repeated intraperitoneal injections of oxaliplatin (3 mg/kg, i.p.) on days 0, 2, 4 and 7 (CD=12 mg/kg, i.p.). Chronic neuropathy in humans is cumulative as well and is most commonly seen in patients who have received total doses of oxaliplatin > or =540 mg/m$^2$ which corresponds to ~15 mg/kg as cumulative dose in rats (Cersosimo R. J. 2005).

The oxaliplatin-induced painful neuropathy in rat reproduces the pain symptoms in oxaliplatin-treated patients:

The thermal hyperalgesia is the earliest symptom. It can be measured with the acetone test or with the tail-immersion test;

The mechanical hyperalgesia appears later. It can be quantified with the Von Frey test or the paw pressure test.

Animal Dosing and Testing

All drug combinations are administered from the day before the first intraperitoneal injection of oxaliplatin 3 mg/kg (D−1) and pursued daily orally until D7. During the testing days (i.e. D1 and D7), the drug combinations are administered after the test. Animals from the reference-treated group (gabapentin) are dosed only during the testing days.

Acetone Test

Cold allodynia is assessed using the acetone test by measuring the responses to thermal non-nociceptive stimulation on D1 (around 24 h after the first injection of oxaliplatin 3 mg/kg (acute effect of oxaliplatin), and D8 (chronic effect of oxaliplatin). In the acetone test, latency of hindpaw withdrawal is measured after application of a drop of acetone to the plantar surface of both hindpaws (reaction time) and the intensity of the response is scored (cold score). Reaction time to the cooling effect of acetone is measured within 20 sec (cut-off) after acetone application. Responses to acetone are also graded to the following 4oint scale: 0 (no response); 1 (quick withdrawal, flick of the paw); 2 (prolonged withdrawal or marked flicking of the paw); 3 (repeated flicking of the paw with licking or biting).

For each experimental group, results are expressed as:

The reaction time defined as the time expressed in sec required to elicit paw reaction (mean of 6 measures for each rat together ±SEM).

The cumulative cold score defined as the sum of the 6 scores for each rat together ±SEM. The minimum score being 0 (no response to any of the 6 trials) and the maximum possible score being 18 (repeated flicking and licking or biting of paws on each of the six trials).

Statistical Analyses

Student test, unilateral, type 3 is performed. The significance level is set as p<0.05; all the groups are compared to the diseased-L vehicle group (oxaliplatin treated group). Means and standard error mean are shown on the figures.

Results

Oxaliplatin induced a significant decrease in reaction time of paw withdrawal after acetone application (diseased group+vehicle) during the time course. This decrease is progressive and significant from day 1 (acute model of oxaliplatin-induced neuropathy) to day 8 (chronic model) as compared to the vehicle group.

Anti-allodynic Effect in Acute Model of Oxaliplatin-induced Neuropathy

The drug combinations tested in acute model of oxaliplatin-induced neuropathy, are assessed with acetone test. Table 12 presents drug combinations (Group 4) which induce a significant decrease in the cumulative cold score and a significant increase of reaction time as compared to the oxaliplatin-vehicle treated group (Group 2). In conclusion, these drug combinations protect animals from acute neuropathy induced by oxaliplatin.

TABLE 12

| Drug combinations tested in acute model of neuropathy (Group 4) | Variation of the cold score compared to Group 2 | Reaction time compared to Group 2 | Anti-allodynic effect |
| --- | --- | --- | --- |
| Baclofen-Torasemide | decrease | increase | + |
| Baclofen-Acamprosate-Torasemide | decrease | increase | + |
| Mexiletine and Cinacalcet | decrease | increase | + |
| Sulfisoxazole and Torasemide | decrease | increase | + |

+ = anti-allodynic effect obtained in Group 4 of rats, following analysis of the cumulative cold scores and analysis of the reaction time in acetone tests, in acute oxaliplatin-induced model.

Anti-allodynic Effect in Chronic Model of Oxaliplatin-induced Neuropathy

The drug combinations used in chronic model of oxaliplatin-induced neuropathy are assessed with acetone test.

Table 13 presents drug combinations, for which, the reaction time and the cold score in acetone test measured in the Group 4 (animals treated with drug combinations and oxaliplatin) are respectively significantly increased and decreased after the treatment in chronic model of neuropathy compared to the oxaliplatin-vehicle treated group (Group 2). In conclusion, these drug combinations protect animals from chronic neuropathy induced by oxaliplatin.

TABLE 13

| Drug combinations tested in Chronic model of neuropathy (Group 4) | Variation of the cold score compared to Group 2 | Reaction time compared to Group 2 | Anti-allodynic effect |
| --- | --- | --- | --- |
| Baclofen-Torasemide | decrease | increase | + |
| Baclofen-Acamprosate-Torasemide | decrease | increase | + |
| Mexiletine and Cinacalcet | decrease | increase | + |
| Sulfisoxazole and Torasemide | decrease | increase | + |

+ = anti-allodynic effect obtained in Group 4 of rats, following analysis of the cumulative cold scores and analysis of the reaction time in acetone tests, in chronic oxaliplatin-induced model.

Figure 28:
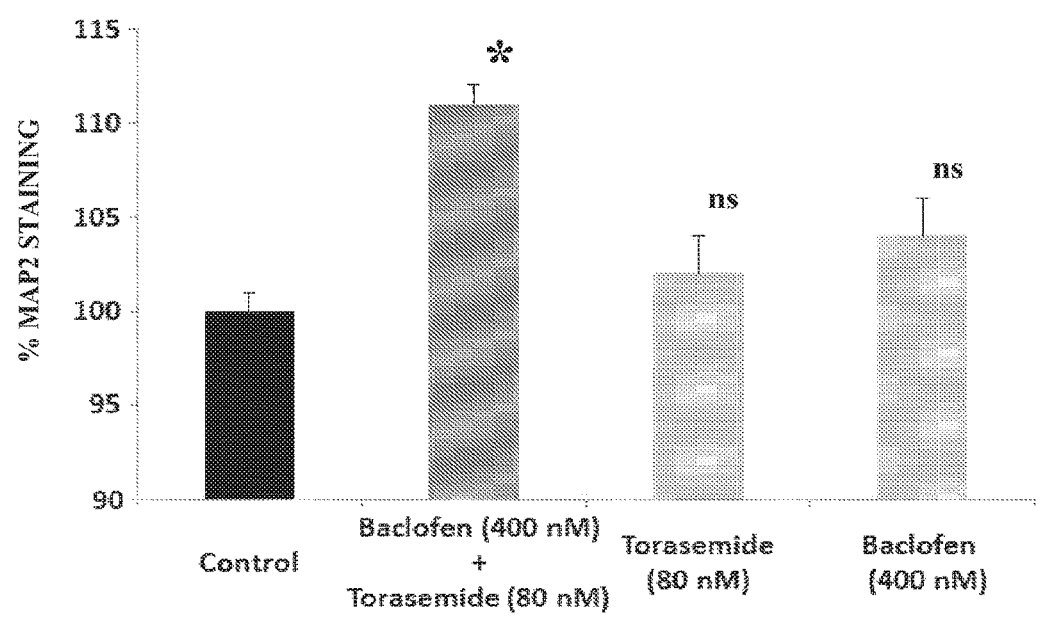
FIG. 28: Effect of Baclofen (BCL) and Torasemide (TOR) combination on the total length of neurites network of cortical neurons cultured in absence of toxic. An increase of neurite network length is observed when Baclofen (400 nM) and Torasemide (80 nM) combination is added in the culture medium; furthermore this combination allows an enhancement of neurite growth whereas, at those concentrations, Baclofen and Torasemide alone have no significant (ns) effect on neurite network length. * $p<0.005$, significantly different from control.

IV) Baclofen-Torasemide Based Compositions Promote Nerve Regeneration in Non Intoxicated Cells Neurotrophic Effects of Baclofen Torasemide Combination In Vitro Neurite Length Assay Neurite growth evaluation within 10 days old cultures of rat cortical cells was performed using MAP-2 antibodies as mentioned in section A) 11.4, with the exception that cells have not been exposed to any toxic. 10 days old cell cultures were incubated with the drugs for 1 day before the assay.
Results As shown in FIG. 28, baclofen-torasemide combination exhibits a significant neurotrophic effect (+11%) whereas individual drugs, when used alone, do not have any substantial neurotrophic effect. Indeed, a significant increase in total neurite length within neuronal network (MAP2-2 labelling) is observed upon exposure to baclofen-torasemide combination (400 nM and 80 nM respectively). Noteworthy, neither combination nor drugs alone have an effect on the number of neurones, thereby stressing that this increase in neurite network is related to an extension of existing neurites and to the promotion of de novo neuronal cell extensions.

These results confirm that baclofen-torasemide combination is efficient in supporting axon extension and thus is efficient in treating spinal cord injury and others nerves injuries. It confirms also that the combination is efficient in treating inherited neuropathies comprising either an axonal, demyelinating, or both axonal and demyelinating component. Indeed, it should be considered that demyelination causes a destabilisation of the axon which results in axonal degeneration observed even in the neuropathies considered to be mainly of the demyelinating form.

Baclofen-torasemide Based Compositions are Efficient in Promoting Nerve Regeneration In Vivo Sciatic nerve crush is widely accepted as a valid model for peripheral nerve injury and for the assessment of nerve regeneration. In this model, nerve damage results in rapid disruption of nerve function as evidenced by the measure of the evoked muscle action potential (CMAPs) generated through the stimulation of the injured sciatic nerve.

Nerve injury is characterized by a lower nerve conduction of the signal that results by an increased latency in generation of CMAP and by an impaired strength of action potential resulting in a decreased amplitude and duration.

Usually, first signs of recovery of nerve function occur within 2 weeks, and, by week 4 post-lesioning, a significant remyelination of the regenerated axons is observed in the sciatic nerve by histology (45).

Nerve Crush

Mice were anesthetized using isoflurane (2.5 to 3% in air). The right thigh was then shaved and the sciatic nerve exposed at mid-thigh level and crushed at 5 mm proximal to the bifurcation of the sciatic nerve. The nerve were crushed for 10 s twice with a microforceps (Holtex, reference P35311) with a 90" rotation between each crush. For sham operated animals, sciatic nerves were exposed but not crushed. Finally, the skin incision was secured with wound clips. The day of the crush is considered as day 0.

Dosage Schedule

The day of the crush, first administration of compounds was performed 30 min after the crush.

Compounds are then after administered twice daily, from the day after the crush and during 42 days. Within a single day, drug administrations were spaced by at least 6 hours.

On test days (days 7 and 30) mice were administered 1 h30 before the test. The volume of administration was 10 ml/kg, in 0.25% DMSO/sterile water.

|  | Dose 1 (bid) | Dose 2 (bid) | Dose 3 (bid) |
| --- | --- | --- | --- |
| Baclofen (+/−) | 3 mg/kg | 3 mg/kg | 3 mg/kg |
| Torasemide | 25 µg/kg | 100 µg/kg | 400 µg/kg |

Electromyography Measures

Electrophysiological recordings were performed using a Keypoint electromyography (EMG) (Medtronic, France) on Day 7 and Day 30. Mice were anaesthetized by 2.5-3% isoflurane in air. Subcutaneous monopolar needle electrodes were used for both stimulation and recording. Supramaximal (12.8 ma) square waves pulses of 0.2 ins duration were used to stimulate the sciatic nerve. The right sciatic nerve (ipsilateral) was stimulated with single pulse applied at the sciatic notch. CMAP was recorded by needle electrodes placed at the gastrocnemius muscle. The onset (latency) of CMAP signal expressed in milliseconds is used to estimate the nerve conduction velocity. Latency thus reflects the degree of myelinisation of the axons. The amplitude of the action (µV) potential was also determined, it reflects the level of denervation and of reinervation of muscles. Amplitude of CHAP is currently given as proportional to the number of regenerated motor axons. Duration of the evoked muscle potential was also determined. Amplitude and duration of the evoked muscle potential are more related to muscle reinervation. Latency and Amplitude are more generally recognized as the most important endpoints when dealing with nerve regeneration. Data were analyzed with a bilateral, type 3, Student t-test; significant level is set at $p<0.05$.

Results

Baclofen-torasemide combinations are efficient, at all the tested doses, in significantly improving time latency of signal when compared with vehicle treated animals, and this as soon a the seventh day from the nerve injury (FIG. 29, A). A significant difference is still observed at the $30^{th}$ day from the nerve crush, when usually a beginning for a spontaneous recovery is observed.

A statistically significant improvement in the amplitude of the signal is also observed for the Dose 3 on the $30^{th}$ day from the nerve crush (FIG. 29, B). Such an improvement is also observed, but to a lesser extent, for doses 1 and 2. Similar results are observed when measuring the duration of the signal.

Altogether, these in vivo results show the efficiency of baclofen-torasemide combination in promoting nerve regeneration through remyelinisation and muscle reinervation. Hence in vim experimental data confirm the neurotrophic effects of baclofen-torasemide observed in vitro and their usefulness in correcting neuropathies where nerves of the peripheral nervous system are damaged (i.e. neuropathies as defined in the specification) but also spinal cord injury.

REFERENCES

1. Crook R. et al. (1998). A variant of Alzheimer's disease with spastic paraparesis and unusual plaques due to deletion of exon 9 of presenilin 1. *Nat Med.* 4(4): 452-5.
2. Houlden H., Baker M., et al. (2000). Variant Alzheimer's disease with spastic paraparesis and cotton wool plaques is caused by PS-1 mutations that lead to exceptionally high amyloid-beta concentrations. *Ann Neurol.* 48(5): 806-8.
3. Kwok J. B., Taddei K., et al. (1997). Two novel presenilin-1 mutations in early-onset Alzheimer's disease pedigrees and preliminary evidence for association of presenilin-1 mutations with a novel phenotype. *Neuroreport.* 8(6): 1537-42.
4. Verkkoniemi A., Kalimo H., et al. (2001). Variant Alzheimer disease with spastic paraparesis: neuropathological phenotype. *J Neuropathol Exp Neural.* 60(5): 483-92.
5. Citron M. (2004). Strategies for disease modification in Alzheimer's disease. *Nat Rev Neurosci.* 5(9): 677-85.

6. Suh. Y. H. and Checler F. (2002). Amyloid precursor protein, presenilins, and alpha-synuclein: molecular pathogenesis and pharmacological applications in Alzheimer's disease, *Pharmacol Rev,* 54(3): 469-5.25.

7. Glenner G. G., Wong et al. (1984). The amyloid deposits in Alzheimer's disease: their nature and pathogenesis. *Appl Pathol.* 2(6): 357-69.

8. Ballatore C., Lee V. M., et al. (2007). Tan-mediated neurodegeneration in Alzheimer's disease and related disorders. *Nat Rev Neurosci.* 8(9): 663-72.

9. Bell K. F. and Claudio Cuello A. (2006). Altered synaptic function in Alzheimer's disease. *Eur J Pharmacol.* 545(1): 11-21.

10. Hardy J. A. and Higgins G. A. (1992). Alzheimer's disease: the amyloid cascade hypothesis. *Science.* 256 (5054): 184-5.

11. Brook H. and Brook E. (1991). Neuropathological staging of Alzheimer-related changes. *Acta Neuropathol.* 82(4): 239-59.

12. Golde T. E. (2005). The Abeta hypothesis: leading us to rationally-designed therapeutic strategies for the treatment or prevention of Alzheimer disease. *Brain Pathol.* 15(1): 84-7.

13. Hardy J. and Selkoe D. J. (2002). The amyloid hypothesis of Alzheimer's disease: progress and problems on the road to therapeutics. *Science.* 297(5580): 353-6.

14. Selkoe D. J. (2000). The genetics and molecular pathology of Alzheimer's disease: roles of amyloid and the presenilins. *Neural Clin.* 18(4): 903-22.

15, Zlokovic B. V., The Blood Brain Barrier In Health And Chronic Neurodegenerative Disorders. *Neuron review.* 2008, 57, 178-201.

16. Budd Haeberlein, S. I. and S. A. Lipton, *Excitotoxicity in neurodegenerative disease*, in *Encyclopedia of neuroscience,* L. R. Squire, Editor. 2009, Elsevier. p. 77-86.

17. Hughes, J. R., Alcohol withdrawal seizures. *Epilepsy Behav,* 2009. 15(2): p. 92-7.

18. Kim, A. H., G. A. Kerchner, and C. D W, *Blocking Excitotoxicity*, in *CNS Neuroprotection,* F. W. Marcoux and D. W. Choi, Editors. 2002, Springer: New York. p. 3-36.

19. Hama A, Sagen J., Antinociceptive effect of riluzole in rats with neuropathic spinal cord injury pain. J Neurotrauma. 2011 January; 28(1):127-34.

20. Lees, K. R., et al., *Glycine antagonist (gavestinel) in neuroprotection (GAIN International) in patients with acute stroke: a randomised controlled trial. GAIN international Investigators.* Lancet, 2000. 355(9219): p. 1949-54.

21, Malgouris, C., et al., *Riluzole, a novel antiglutamate prevents memory loss and hippocampal neuronal damage in ischemic gerbils.* J Neurosci, 1989. 9(11): p. 3720-7.

22. Wahl, F., et al., *Effect of riluzole on focal cerebral ischemia in rats.* Eur Pharmacol; 1993. 230 (2): p. 209-14.

23. Wahl, F., et al., *Riluzole reduces brain lesions and improves neurological function in rats after a traumatic brain injury.* Brain Res, 1997. 756(1-2): p. 247-55, 24. Ettmayer, P., Amidon, G, L., Clement, B. & Testa, B. Lessons learned from marketed and investigational prodrugs. *J. Med. Chem.* 47, 2393-2104 (2004).

25. Beaumont, K., Webster, R., Gardner, I. & Dack, K. Design of ester prodrugs to enhance oral absorption of poorly permeable compounds: challenges to the discovery scientist. *Curr. Drug Metab.* 4, 461-485 (2003).

26, Heimbach, T. et al. Enzyme-mediated precipitation of parent drugs from their phosphate prodrugs. *Int. J Pharm.* 261, 81-92 (2003).

27, Yang, C. Y., Dantzig, A. H. & Pidgeon, C. Intestinal peptide transport systems and oral drug availability. *Pharm. Res.* 16, 1331-1343 (1999).

28. Steffansen, B. et al. Intestinal solute carriers: an overview of trends and strategies for improving oral drug absorption. *Eur. J. Pharm. Sci.* 21; 3-16 (2004).

29. Stella, V. et al. Prodrugs: Challenges and Rewards (AAPS, New York, 2007)

30. Wermuth, C G. The Practice of Medicinal Chemistry. (Hardbound, 2003). Part VI; Chap 33: Designing prodrugs and bioprecursors.

31. Pezron, I, et al. Prodrug strategies in nasal drug delivery. *Expert Opin. Ther. Pat.,* Vol. 12, No. 3, 331-340 (2002).

32. Stella, V. J. Prodrugs as therapeutics. *Expert Opin. Ther. Pat.* 14, 280 (2004).

33. Stella, V. J. & Nti-Addae, K. W. Prodrug strategies to overcome poor water solubility. *Adv. Drug Deliv. Rev.* 59, 677-694 (2007).

34. Higuchi, T.; Stella, V. eds. Prodrugs As Novel Drug Delivery Systems. *ACS Symposium Series.* American Chemical Society: Washington, D.C. (1975). 31.

35. Roche, E. B. Design of Biopharmaceutical Properties through Prodrugs and Analogs. *American Pharmaceutical Association: Washington,* D.C. (1977).

36. Lal, R., et al., Arbaclofen placarbil, a novel R-baclofen prodrug: improved absorption, distribution, metabolism, and elimination properties compared with R-baclofen. J Pharmacol Exp Ther, 2009, 330(3): p. 911-21.

37. Andrew R. Leach, Valerie J. Gillet. An Introduction to Chemoinformatics. Springer 2007.

38. S. Asad Rahman, M. Bashton, G. L. Holliday, R. Schrader and J. M. Thornton: Small Molecule Subgraph. Detector (SMSD) Toolkit, Journal of Cheminformatics 2009, 1:12 doi:10.1186/1758-2946-1-12

39. Wishart D S, Knox C, Guo A C, Cheng D, Shrivastava S, Tzur D, Gautan B, Hassanali M. *DrugBank: a knowledgebase for drugs, drug actions and drug targets,* Nucleic Acids Res. 36, Issuesuppl 1. D901-D906 (2008).

40. Stahl H., Wermuth. C. G. (Eds.) Handbook of *Pharmaceutical Salts*: Properties, Selection, and Use. Wiley-VCR, 2 edition (Mar. 29, 2011).

41. Hanati R, Mosad S, Abouzid K, Niess R, Spahn-Langguth H. *Baclofen ester and carbamate prodrug candidates; a simultaneous chromatographic assay, resolution optimized with DryLab.* J Pharm Biomed Anal, 2011. 56(3): p. 569-76.

42. Singer C., Figueroa-Masot X., Batchelor R., and Dorsa D. *Mitogen-activated protein kinase pathway mediates estrogen neuroprotection after glutamate toxicity in primary cortical neurons.* J. Neuroscience, 1999. 19(7):2455-2463.

43. Feng Xu, Ge Peng, Thu Phan, Usha Dilip, Jian Lu Chen, Tania Chernov-Rogan, Xuexiang Zhang, Kent Cirindstaff, Thamil Annamalai, Kerry Koller, Mark A. Gallop, David J. Wustrow, Discovery of a novel potent GABAB receptor agonist; Bioorg Med. Chem Lett. 2011 Nov. 1; 21(21):6582-5.)

44. Braun S, Croizatb B, Lagrangec M C, Wartera J M, Poindron P. *Neurotrophins increase motoneurons' ability to innervate skeletal muscle fibers in rat spinal cord-human muscle cocultures.* Volume 136, Issues 1-2, March 1996, Pages 17-23.

45. Bordet T, Buisson B, Michaud M, Drouot C, Galéa P, Delaage P, Akentieva N P, Evers A S, Covey D E, Ostuni M. A, Lacapeère J J, Massaad C, Schumacher M, Steidl E M, Maux D, Delaage M, Henderson C E, Pruss R M. *Identification and characterization of cholest-4-en-3-one, oxime (TRO19622), a novel drug candidate for amyotrophic lateral sclerosis.* J Pharmacol Exp Ther. 2007 August; 322(2): 709-20.

The invention claimed is:

1. A method of treating a subject having Parkinson's disease, comprising administering to said subject an effective amount of torasemide and baclofen, or prodrugs, or salts, or sustained release formulations thereof, with the proviso that said method does not comprise the administration of acamprosate.

2. The method of claim 1, further comprising administering to said subject a compound selected from the group consisting of mexiletine, sulfisoxazole, cinacalcet and tadalafil, or prodrugs, or salts, or sustained release formulations thereof.

3. The method of claim 1, wherein the compounds are administered with a pharmaceutically acceptable carrier or excipient.

4. The method of claim 1, wherein the compounds are administered repeatedly to the subject.

5. The method of claim 1, wherein the compounds are administered orally.

6. The method of claim 1, wherein torasemide is administered in a dosage from about 0.05 to 4 mg per day.

7. The method of claim 1, wherein baclofen is administered in a dosage from about 0.15 to 15 mg per day.

* * * * *